(12) United States Patent
Gomtsyan et al.

(10) Patent No.: US 8,232,309 B2
(45) Date of Patent: Jul. 31, 2012

(54) PRODRUGS OF COMPOUNDS THAT INHIBIT TRPV1 RECEPTOR

(75) Inventors: Arthur R. Gomtsyan, Vernon Hills, IL (US); Erol K. Bayburt, Gurnee, IL (US); John R. Koenig, Chicago, IL (US); Kennan C. Marsh, Lake Forest, IL (US); Robert G. Schmidt, Jr., Waukegan, IL (US); Chih-Hung Lee, Vernon Hills, IL (US); Weili Wang, Buffalo Grove, IL (US); Jerome F. Daanen, Racine, WI (US); Brian S. Brown, Evanston, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 11/588,713

(22) Filed: Oct. 27, 2006

(65) Prior Publication Data

US 2007/0099954 A1   May 3, 2007

Related U.S. Application Data

(60) Provisional application No. 60/730,991, filed on Oct. 28, 2005.

(51) Int. Cl.
*A61K 31/416* (2006.01)
*C07D 231/56* (2006.01)

(52) U.S. Cl. .................... 514/406; 548/362.5
(58) Field of Classification Search ............. 548/362.5
See application file for complete search history.

(56) References Cited

U.S. PATENT DOCUMENTS

| 7,015,233 B2 * | 3/2006 | Gomtsyan et al. ............ 514/322 |
| 2004/0254188 A1 | 12/2004 | Gomtsyan et al. |
| 2005/0043351 A1 * | 2/2005 | Gomtsyan et al. ............ 514/310 |
| 2006/0128689 A1 | 6/2006 | Gomtsyan et al. |

FOREIGN PATENT DOCUMENTS

WO 2004/111009 12/2004

OTHER PUBLICATIONS

Cancer and Metastasis Reviews (1998), 17 (1), 91-106.*
Science (1999), vol. 286 531-537.*
Cancer [online], [retrieved on Jul. 6, 2007]. Retrieved from the Internet, URL; http://www.nlm.nih.gov/medlineplus/cancer.html>.*
Cancer [online], [retrieved on Jul. 6, 2007]. Retrieved from the Internet, URL; http://en.wikipedia.org/wiki/Cancer>.*
Vippagunta, et al. Advanced Drug Delivery Reviews 48 (2001) 3-26.*
Rheumatoid arthritis [online] retrieved on Aug. 14, 2010. (URL: <http://www.medicinenet.com/rheumatoid_arthritis/article.htm>).*
Interstitial cystitis [online] retrieved on Aug. 14, 2010. (URL: <http://health.google.com/health/ref/Interstitial+cystitis>).*
Caterina, M.J., et al., "The Vanilloid Receptor: A Molecular Gateway to the Pain Pathway", Annu. Rev. Neurosci., vol. 24, pp. 487-517, 2001.
Caterina, M.J., et al., "The capsaicin receptor: a heat-activated ion channel in the pain pathway", Nature, vol. 389, pp. 816-824, 1997.
Caterina, M.J., et al., "Impaired Nociception and Pain Sensation in Mice Lacking the Capsaicin Receptor", Science, vol. 288, pp. 306-313, 2000.
Davis, J., et al., "Vanilloid receptor-1 is essential for inflammatory thermal hyperalgesia", Nature, vol. 405, pp. 183-187.
Fowler, C., "Intravesical Treatment of Overactive Bladder", Urology, vol. 55, pp. 60-64, 2000.
Higuchi, T., "Pro-drugs as Novel Delivery Systems", American Chemical Society Symposium Series, vol. 14, 1975.
Nolano, M., et al., "Topical capsaicin in humans: parallel loss of epidermal nerve fibers and pain sensation", Pain, vol. 81, pp. 135-145, 1999.
Honore, et al., Pharmacol. Exp. Ther. 2005, 314(1), pp. 410-421.
Drizin, et al., Bioorg. Med. Chem. 2006, 14, pp. 4740-4749.

* cited by examiner

*Primary Examiner* — Shawquia Young
(74) *Attorney, Agent, or Firm* — Lisa V. Mueller; Michael Best & Friedrich LLP

(57) ABSTRACT

Compounds of formula (I)

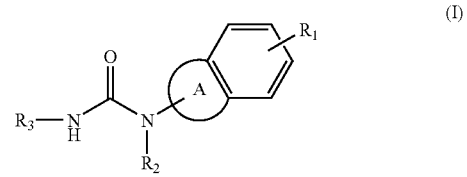

wherein A, $R_1$, $R_2$, and $R_3$ are defined in the specification, and which are useful as therapeutic compounds particularly for treating disorders or conditions associated with inflammation, pain, bladder overactivity, urinary incontinence, and other disorders caused by or exacerbated by TRPV1.

22 Claims, No Drawings

PRODRUGS OF COMPOUNDS THAT INHIBIT TRPV1 RECEPTOR

This application claims priority to the provisional application Ser. No. 60/730,991 filed on Oct. 28, 2005.

FIELD OF INVENTION

The present invention relates to prodrugs of urea containing compounds, pharmaceutically acceptable salts and pharmaceutical compositions thereof, which are useful for treating pain, bladder overactivity, urinary incontinence, and other disorders caused by or exacerbated by vanilloid receptor activity. The compounds of the present invention have better physicochemical properties permitting more active drug to be available.

BACKGROUND OF THE INVENTION

Nociceptors are primary sensory afferent (C and Aδ fibers) neurons that are activated by a wide variety of noxious stimuli including chemical, mechanical, thermal, and proton (pH <6) modalities. The lipophillic vanilloid, capsaicin, activates primary sensory fibers via a specific cell surface capsaicin receptor, cloned as TRPV1. The intradermal administration of capsaicin is characterized by an initial burning or hot sensation followed by a prolonged period of analgesia. The analgesic component of TRPV1 receptor activation is thought to be mediated by a capsaicin-induced desensitization of the primary sensory afferent terminal. Thus, the long lasting antinociceptive effects of capsaicin have prompted the clinical use of capsaicin analogs as analgesic agents. Further, capsazepine, a capsaicin receptor antagonist can reduce inflammation-induced hyperalgesia in animal models. TRPV1 receptors are also localized on sensory afferents, which innervate the bladder. Capsaicin or resiniferatoxin has been shown to ameliorate incontinence symptoms upon injection into the bladder.

The TRPV1 receptor has been called a "polymodal detector" of noxious stimuli since it can be activated in several ways. The receptor channel is activated by capsaicin and other vanilloids and thus is classified as a ligand-gated ion channel. TRPV1 receptor activation by capsaicin can be blocked by the competitive TRPV1 receptor antagonist, capsazepine. The channel can also be activated by protons and heat. Under mildly acidic conditions (pH 6-7), the affinity of capsaicin for the receptor is increased, whereas at pH <6, direct activation of the channel occurs. In addition, when membrane temperature reaches 43° C., the channel is opened. Thus heat can directly gate the channel in the absence of ligand. The capsaicin analog, capsazepine, which is a competitive antagonist of capsaicin, blocks activation of the channel in response to capsaicin, acid, or heat.

The channel is a nonspecific cation conductor. Both extracellular sodium and calcium enter through the channel pore, resulting in cell membrane depolarization. This depolarization increases neuronal excitability, leading to action potential firing and transmission of a noxious nerve impulse to the spinal cord. In addition, depolarization of the peripheral terminal can lead to release of inflammatory peptides such as, but not limited to, substance P and CGRP, leading to enhanced peripheral sensitization of tissue.

Recently, two groups have reported the generation of a "knock-out" mouse lacking the TRPV1 receptor (TRPV1 (−/−)). Electrophysiological studies of sensory neurons (dorsal root ganglia) from these animals revealed a marked absence of responses evoked by noxious stimuli including capsaicin, heat, and reduced pH. These animals did not display any overt signs of behavioral impairment and showed no differences in responses to acute non-noxious thermal and mechanical stimulation relative to wild-type mice. The TRPV1 (−/−) mice also did not show reduced sensitivity to nerve injury-induced mechanical or thermal nociception. However, the TRPV1 knock-out mice were insensitive to the noxious effects of intradermal capsaicin, exposure to intense heat (50-55° C.), and failed to develop thermal hyperalgesia following the intradermal administration of carrageenan.

The compounds of the present invention are novel TRPV1 antagonists and have utility in for treating pain, bladder overactivity, urinary incontinence, and other disorders associated with pain that are caused by or exacerbated by vanilloid receptor activity.

SUMMARY OF THE PRESENT INVENTION

The present invention discloses prodrugs of urea containing compounds, pharmaceutically acceptable salts and pharmaceutical compositions thereof. More particularly, the present invention is directed to compounds of formula (I),

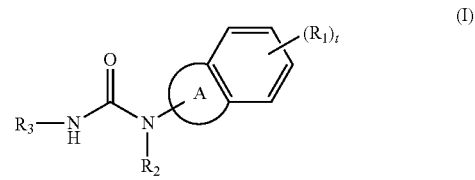

or a pharmaceutically acceptable salt, prodrug, salt of a prodrug or a combination thereof, wherein A is

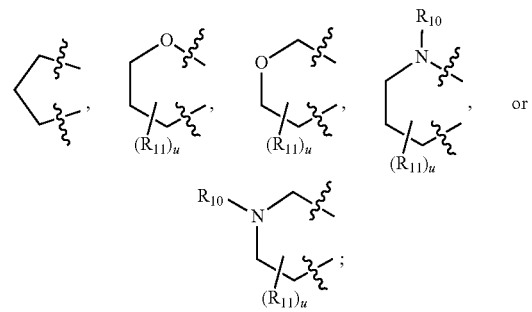

$R_1$ is alkyl, cycloalkyl, alkenyl; halogen or haloalkyl;

$R_2$ is hydrogen or heterocyclealkyl wherein the heterocycle moiety of the heterocyclealkyl is unsubstituted or substituted with 1, 2, 3 or 4 substituents selected from the group consisting of alkyl, -alkyl-$OR_B$, and -alkyl-$N(R_B)_2$;

$R_3$ is

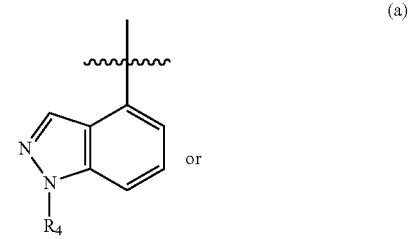

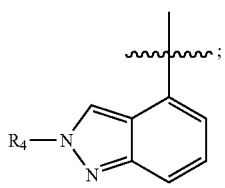

wherein
- $R_4$ is —C(O)—O—(CH$_2$)$_m$R$_5$, —C(O)(CH$_2$)$_n$—R$_6$, —(CH$_2$)$_r$—R$_7$, —C(O)R$_8$, or —CH$_2$C(H)(OH)R$_9$ when $R_2$ is hydrogen; or
- $R_4$ is hydrogen when $R_2$ is heterocyclealkyl; wherein the heterocycle moiety of the heterocyclealkyl is unsubstituted or substituted with 1, 2, 3 or 4 substituents selected from the group consisting of alkyl, -alkyl-OR$_B$, and -alkyl-N(R$_B$)$_2$;
- m is 1, 2, or 3;
- n is 1, 2 or 3;
- r is 1, 2 or 3;
- t is 0, 1, 2, 3 or 4;
- u is 0, 1, 2 or 3;
- $R_5$ is alkyl, —O—P(O)(OR$_A$)(OR$_A$), —P(O)(OR$_A$)(OR$_A$), —OR$_A$, —OC(O)(R$_A$), heterocycle, —C(O)OR$_A$, —C(O)N(R$_B$)$_2$, —C(O)(R$_A$), —NR$_A$R$_B$, or —N(R$_B$)C(O)OR$_A$,
- $R_6$ is alkyl, —OC(O)(R$_A$), —OR$_A$, —C(O)OR$_A$, —NR$_A$R$_B$, —OP(O)(OR$_A$)(OR$_A$), or —P(O)(OR$_A$)(OR$_A$);
- $R_7$ is alkoxy, heterocycle, —OC(O)(R$_A$), —OC(O)(hydroxyalkyl), —OP(O)(OR$_A$)(OR$_A$), or —P(O)(OR$_A$)(OR$_A$),
- $R_8$ is heterocycle or N(R$_{8a}$)(R$_{8b}$) wherein R$_{8a}$ and R$_{8b}$ are independently hydrogen or alkyl;
- $R_9$ is alkoxyalkyl, —C(O)OR$_A$, -alkyl-N(R$_B$)C(O)OR$_A$, or heterocyclealkyl;
- $R_{10}$ is alkyl;
- each occurence of $R_{11}$ are independently hydrogen, alkyl or aryl, or two $R_{11}$ groups that are attached to a single carbon atom together form a cycloalkyl ring;
- $R_A$ is hydrogen, alkyl, alkoxyalkyl, aryl or arylalkyl;
- $R_B$ is hydrogen or alkyl;
- the heterocycle and the heterocycle moiety of the heterocyclealkyl, represented by $R_5$, $R_7$, $R_8$, and $R_9$, are each independently substituted with 0, 1, 2 or 3 substituents independently selected from the group consisting of alkyl, haloalkyl, alkoxy, haloalkoxy, —C(O)OH, -alkyl-C(O)OH, and —N(Z$_A$)(Z$_B$);
- $Z_A$ and $Z_B$ are each independently hydrogen, alkyl, —C(O)alkyl, formyl, aryl, or arylalkyl; and
- the aryl and the aryl moiety of the arylalkyl, represented by $R_A$, $Z_A$ and $Z_B$ are each independently substituted with 0, 1, 2 or 3 substituents selected from the group consisting of alkyl, haloalkyl, alkoxy and haloalkoxy.

The compounds of the present invention are useful for treating pain, bladder overactivity, urinary incontinence, and other disorders caused by or exacerbated by vanilloid receptor activity.

Also described are pharmaceutical compositions comprising a therapeutically effective amount of one or more compounds of formula (I), or a therapeutically acceptable salt, solvate, or combination thereof, and a pharmaceutically acceptable carrier.

One particular embodiment of the present invention describes a method of treating a disease or preventing disorders that may be ameliorated by inhibiting vanilloid receptor subtype 1 activity in a mammal comprising administering a therapeutically effective amount of one or more compounds of formula (I) or a pharmaceutically acceptable salt thereof.

The compounds of formula (I) may be used in the manufacture of a medicament for the treatment or prevention of a disease or disorder that may be ameliorated by inhibiting vanilloid receptor subtype 1 activity.

Furthermore, the disclosed compounds of formula (I) are useful in treating a disease or a disorder, wherein the disease or disorder is associated with pain, inflammation, urinary incontinence and bladder dysfunction.

The disclosed methods of treating or preventing disease or disorder associated with pain wherein the pain is neuropathic pain, inflammatory pain, or both, which method comprises administering a therapeutically effective amount of a compound of formula (I) or a pharmaceutically acceptable salt thereof.

There is also disclosed methods of treating or preventing a disease or disorder associated with bladder overactivity or urinary incontinence, or both, which method comprises administering a therapeutically effective amount of a compound of formula (I) according to claim 1 or a pharmaceutically acceptable salt thereof.

DETAILED DESCRIPTION OF THE INVENTION

Compounds of the invention have the formula (I) as described above. In general, the compounds of formula (I) can include, but are not limited to, compounds in which A is

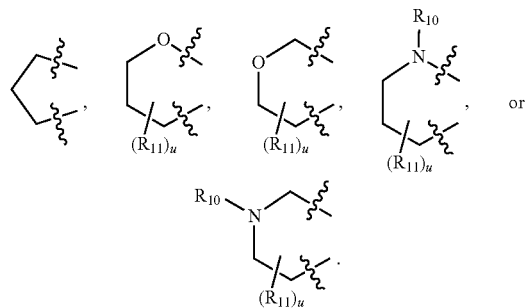

More particularly, compounds of formula (I) contain A which is

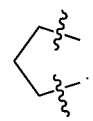

In another series of embodiments, compounds of formula (I) contain A which is

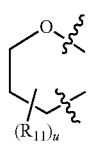

In a further series of embodiments, compounds of formula (I) contain A which is

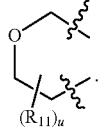

In yet another series of embodiments, compounds of formula (I) contain A which is

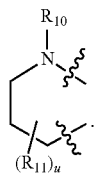

Lastly in yet another series of embodiments, compounds of formula (I) contain A which is

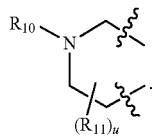

For each substructure as defined by ring A, there exist the following embodiments which further define the scope of the compounds of the present invention. These further embodiments are contemplated to apply to each series of compounds of the present invention defined under ring A.

In one embodiment there is described compounds of formula (I) wherein $R_1$ is alkyl, cycloalkyl, halogen or haloalkyl, $R_2$ is hydrogen or heterocyclealkyl, $R_3$ is selected from the groups (a)

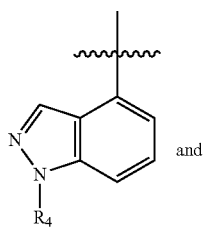

and (b)

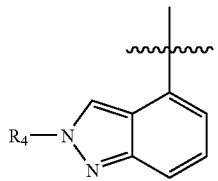

and $R_4$ is selected form the group consisting of —C(O)—O—$(CH_2)_m R_5$, —C(O)$(CH_2)_n$—$R_6$, —$(CH_2)_r$—$R_7$, —C(O)$R_8$, or —$CH_2C(H)(OH)R_9$ when $R_2$ is hydrogen.

Compounds of the invention include those wherein $R_1$ is alkyl, cycloalkyl, halogen or haloalkyl, preferably alkyl, $R_2$ is hydrogen, $R_3$ is (a)

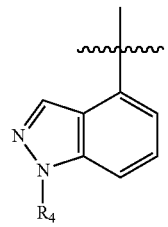

and $R_4$ is —$(CH_2)_r$—$R_7$, in which $R_7$ selected from the group consisting of heterocycle, —OC(O)($R_A$), —OC(O)(hydroxyalkyl), and —P(O)(O$R_A$)(O$R_A$). Preferred compounds include those in which $R_7$ is —OC(O)($R_A$), and $R_A$ is hydrogen or those in which $R_7$ is —OC(O)(hydroxyalkyl).

Other compounds of the present invention include those wherein $R_1$ is alkyl, cycloalkyl, halogen or haloalkyl, preferably alkyl, $R_2$ is hydrogen, $R_3$ is (a)

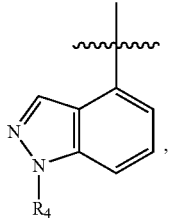

and $R_4$ is —C(O)$(CH_2)_n$—$R_6$, wherein $R_6$ is selected from the group consisting of is —OC(O)($R_A$), —O$R_A$, —C(O)O$R_A$, —N$R_A R_B$, —OP(O)(O$R_A$)(O$R_A$) or —P(O)(O$R_A$)(O$R_A$). Examples of compounds of the present invention are those in which $R_A$ is hydrogen, alkyl, aryl or arylalkyl.

Other compounds of the present invention include those wherein $R_1$ is alkyl, cycloalkyl, halogen or haloalkyl, preferably alkyl, $R_2$ is hydrogen, $R_3$ is (a)

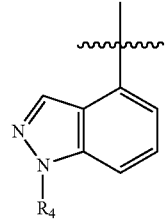

and $R_4$ is —$CH_2C(H)(OH)R_9$, wherein $R_9$ is selected from the group consisting of alkoxyalkyl, —C(O)O$R_A$, -alkyl-N($R_B$)C(O)O$R_A$, and heterocyclealkyl. Examples of compounds of the present invention are those in which $R_9$ is alkoxyalkyl, —C(O)O$R_A$, and heterocyclealkyl, and $R_A$ is hydrogen, alkyl, aryl or arylalkyl.

Other compounds included in the present invention are those in which $R_1$ is alkyl, cycloalkyl, halogen or haloalkyl, preferably alkyl, $R_2$ is hydrogen, $R_3$ is

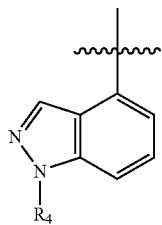

(a)

and $R_4$ is —C(O)$R_8$, wherein $R_8$ is heterocycle or N($R_{8a}$)($R_{8b}$). Examples of compounds of the present invention are those in which $R_8$ is heterocycle.

Other compounds included in the present invention are those in which $R_1$ is alkyl, cycloalkyl, halogen or haloalkyl, preferably alkyl, $R_2$ is heterocyclealkyl, $R_3$ is

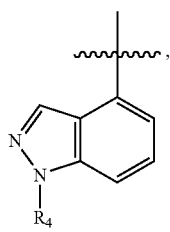

(a)

and $R_4$ is hydrogen. Examples of the present invention comprise compounds in which the heterocycle moiety of the heterocyclealkyl is unsubstituted. However, compounds in which the heterocycle moiety of the heterocyclealkyl is substituted with 1, 2, 3 or 4 substituents selected from the group consisting of alkyl, -alkyl-O$R_B$, and -alkyl-N($R_B$)$_2$, are also comprised in the present invention.

Other compounds included in the present invention are those in which $R_1$ is alkyl, cycloalkyl, halogen or haloalkyl, $R_2$ is heterocyclealkyl, $R_3$ is

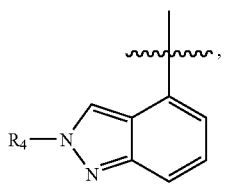

(b)

and $R_4$ is hydrogen.

Compounds of the present invention include those wherein $R_1$ is alkyl, cycloalkyl, halogen or haloalkyl, preferably alkyl, $R_2$ is hydrogen, $R_3$ is

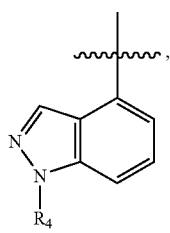

(a)

and $R_4$ is —C(O)—O—(CH$_2$)$_m$$R_5$, wherein $R_5$ is selected from the group consisting of —O—P(O)(O$R_A$)(O$R_A$), —P(O)(O$R_A$)(O$R_A$), —O$R_A$, —OC(O)($R_A$), heterocycle, —C(O)O$R_A$, —C(O)N($R_B$)$_2$, —C(O)($R_A$), and —N($R_B$)C(O)O$R_A$. Examples of these compounds include those in which $R_5$ is —O—P(O)(O$R_A$)(O$R_A$), and $R_A$ is independently selected from the group consisting of hydrogen, alkyl, aryl or arylalkyl. Other examples include those compounds in which $R_5$ is —P(O)(O$R_A$)(O$R_A$), and $R_A$ is independently selected from the group consisting of hydrogen, alkyl, aryl or arylalkyl. Examples of compounds include those in which $R_5$ is O$R_A$ and $R_A$ is independently selected from the group consisting of hydrogen, alkyl, aryl or arylalkyl. Other examples include those in which $R_5$ is heterocycle. Examples include compounds in which $R_5$ is OC(O)($R_A$), and $R_A$ is independently selected from the group consisting of hydrogen, alkyl, aryl or arylalkyl. Other examples include those compounds in which $R_5$ is —C(O)O$R_A$, and $R_A$ is independently selected from the group consisting of hydrogen, alkyl, aryl or arylalkyl. Other compounds included in the examples of the present invention are those in which $R_5$ is —C(O)N($R_B$)$_2$, and $R_B$ is selected between hydrogen and alkyl. Other compounds included in the examples of the present invention are those in which $R_5$ is —N($R_B$)C(O)O$R_A$ wherein $R_B$ is selected between hydrogen and alkyl, and $R_A$ is independently selected from the group consisting of hydrogen, alkyl, aryl or arylalkyl.

Other compounds of the present invention are those in which $R_1$ is alkyl, cycloalkyl, halogen or haloalkyl, preferably alkyl, $R_2$ is hydrogen, $R_3$ is

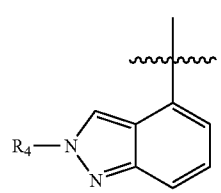

(b)

and $R_4$ is —C(O)$R_8$, in which $R_8$ is heterocycle or N($R_{8a}$)($R_{8b}$) wherein $R_{8a}$ and $R_{8b}$ are independently hydrogen or alkyl. Examples of the present invention include compounds in which $R_8$ is heterocycle.

Other compounds of the present invention are those in which $R_1$ is alkyl, cycloalkyl, halogen or haloalkyl, preferably alkyl, $R_2$ is hydrogen, $R_3$ is

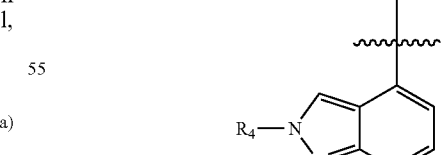

(b)

and $R_4$ is —CH$_2$C(H)(OH)$R_9$, wherein $R_9$ is selected from the group consisting of alkoxyalkyl, —C(O)O$R_A$, -alkyl-N($R_B$)C(O)O$R_A$, and heterocyclealkyl. Examples of the present invention include compounds in which $R_9$ is alkoxyalkyl. Other examples include compounds in which $R_9$ is —C(O)O$R_A$ and $R_4$ is alkyl. Other examples include compounds in which $R_9$ is heterocyclealkyl.

Other compounds of the present invention include compounds in which $R_1$ is alkyl, cycloalkyl, halogen or haloalkyl, preferably alkyl, $R_2$ is hydrogen, $R_3$ is

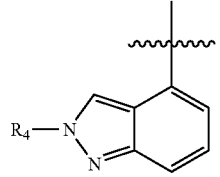

(b)

and $R_4$ is —C(O)—O—(CH$_2$)$_m$R$_5$. Other compounds included in the invention are those in which, $R_1$ is alkyl, cycloalkyl, halogen or haloalkyl, preferably alkyl, $R_2$ is hydrogen, $R_3$ is

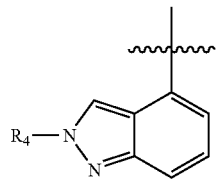

(b)

and $R_4$ is —C(O)(CH$_2$)$_n$—R$_6$. Other compounds included in the invention are those in which, $R_1$ is alkyl, cycloalkyl, halogen or haloalkyl, preferably alkyl, $R_2$ is hydrogen, $R_3$ is

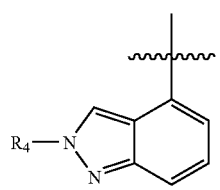

(b)

and $R_4$ is and —(CH$_2$)$_r$—R$_7$. Other compounds included in the present invention have $R_1$ is alkyl or alkenyl, preferably alkyl, $R_2$ is heterocyclealkyl, $R_3$ is

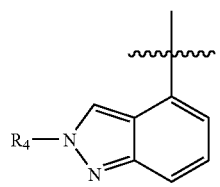

(b)

and $R_4$ is hydrogen.

Furthermore, compounds of formula (II) are considered within the scope of the present invention,

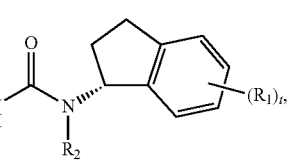

(II)

wherein $R_1$, $R_2$, $R_3$ and t are defined in compounds of formula (I).

Other compounds of the present invention include compounds of formula (III)

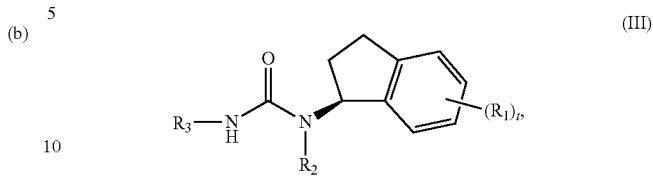

(III)

wherein $R_1$, $R_2$, $R_3$ and t are defined in compounds of formula (I).

Other compounds of the present invention include compounds of formula (IV)

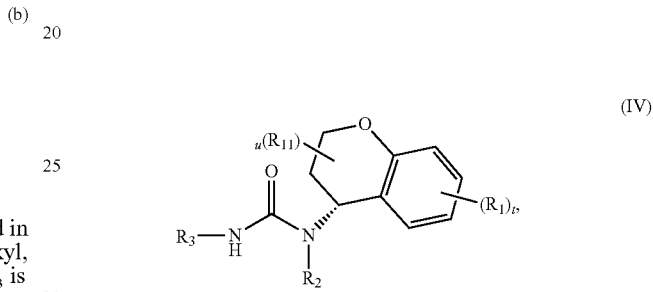

(IV)

wherein $R_1$, $R_2$, $R_3$ and t are defined in compounds of formula (I).

Other compounds of the present invention include compounds of formula (V)

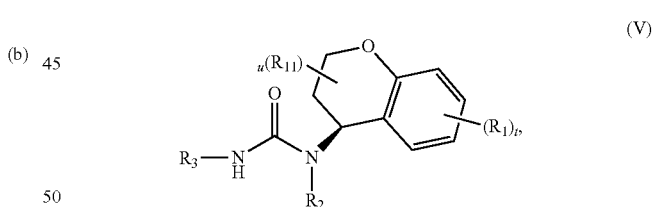

(V)

wherein $R_1$, $R_2$, $R_3$ and t are defined in compounds of formula (I).

The following compounds are contemplated to be within the scope of the present invention:

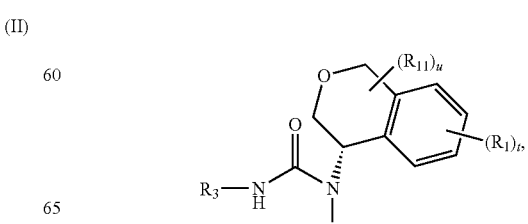

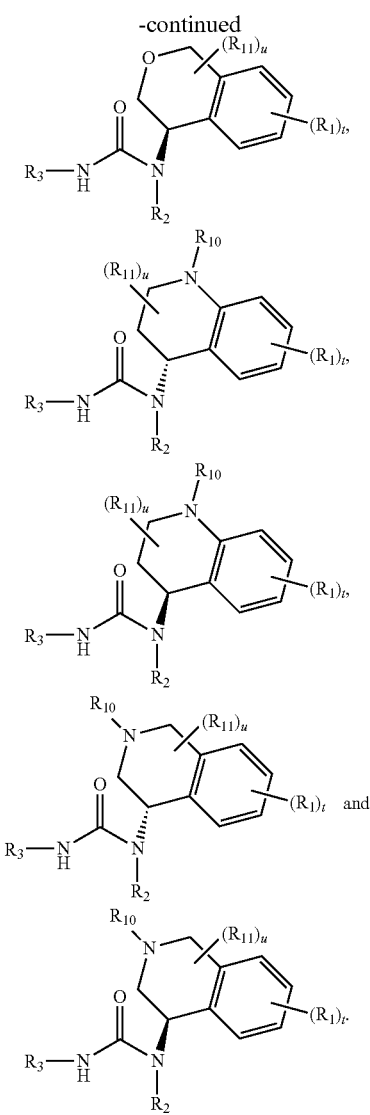

It is contemplated that any of the embodiments described above may be combined and the scope of the compounds of the present invention defined under formula (I) is described by any such combinations.

Compounds and compositions of the invention are useful for modulating the effects of vanilloid receptor activity, and more particularly the receptor type TRPV1. In particular, the compounds and compositions of the invention can be used for treating and preventing disorders modulated by TRPV1. Typically, such disorders can be ameliorated by selectively modulating the TRPV1 receptor in a mammal, preferably by administering a compound or composition of the invention, either alone or in combination with another active agent, for example, as part of a therapeutic regimen. The compounds of the invention, including but not limited to those specified in the examples, possess an affinity for TRPV1's. As TRPV1 ligands, the compounds of the invention can be useful for the treatment and prevention of a number of diseases or conditions mediated by the TRPV1 activity.

For example, TRPV1 have been shown to play a significant role in the release of inflammatory peptides such as, but not limited to, substance P and CGRP, leading to enhanced peripheral sensitization of tissue. As such, TRPV1 ligands are suitable for the treatment of disorders associated with pain and inflammation. Further, capsazepine, a capsaicin receptor antagonist can reduce inflammation-induced hyperalgesia in animal models.

TRPV1 receptors are also localized on sensory afferents, which innervate the bladder. Capsaicin or resiniferatoxin has been shown to ameliorate incontinence symptoms upon injection into the bladder. Therefore, TRPV1 ligands are suitable for the treatment of disorders associated with urinary incontinence and bladder dysfunction.

Definition of Terms.

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. The phenyl and the bicyclic aryl groups of the present invention are unsubstituted or substituted. The bicyclic aryl is attached to the parent molecular moiety through any carbon atom contained within the bicyclic aryl. Representative examples of the aryl groups include, but are not limited to, dihydroindenyl, indenyl, naphthyl, dihydronaphthalenyl, 1,3-benzodioxolyl, 2,3-dihydro-1,4-benzodioxin-6-yl, and 5,6,7,8-tetrahydronaphthalenyl.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "halo" or "halogen" as used herein, means —Cl, —Br, —I or —F.

The term "haloalkoxy" as used herein, means an alkoxy group as defined herein, wherein one to six hydrogen atoms are replaced by halogens. Representative examples of haloalkoxy include, but are not limited to, chloromethoxy, 2-fluoroethoxy, trifluoromethoxy, 2-chloro-3-fluoropentyloxy, and pentafluoroethoxy.

The term "haloalkyl" as used herein, means an alkyl group as defined herein, wherein one to six hydrogen atoms are replaced by halogens. Representative examples of haloalkyl include, but are not limited to, chloromethyl, 2-fluoroethyl trifluoromethyl, pentafluoroethyl, and 2-chloro-3-fluoropentyl.

The term "heterocycle" or "heterocyclic" as used herein, means a monocyclic three-, four-, five-, six-, seven- or eight-membered ring containing at least one heteroatom independently selected from the group consisting of O, N, and S. The three- or four-membered ring contains zero or one double bond, and one heteroatom selected from the group consisting of O, N and S. The five-membered ring contains zero or one double bond and one, two or three heteroatoms selected from the group consisting of O, N and S. The six-membered ring contains zero, one or two double bonds and one, two or three heteroatoms selected from the group consisting of O, N and S. The seven-membered ring contains zero, one, two, or three double bonds and one, two or three heteroatoms selected from the group consisting of O, N and S. The monocyclic heterocycle is unsubstituted or substituted and is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolan-4-yl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl.

The term "heterocyclealkyl" as used herein, means a heterocycle group, as defined herein, appended to the parent moiety through an alkyl group, as defined herein. Examples of heterocyclealkyl of the present invention include, but not limited to, 2-morpholin-4-yl-ethyl and 2-piperidin-1-yl-ethyl.

The term "hydroxy" as used herein, means an —OH group.

The term "hydroxyalkyl" as used herein, means at least one hydroxy group, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "oxo" as used herein, means =O.

Compounds of the present invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30. The present invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the present invention may be prepared synthetically from commercially available starting materials that contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) direct separation of the mixture of optical enantiomers on chiral chromatographic columns, or fractional recrystalization of salt of the compounds of the present invention with chrial carboxylic acids followed by neutralization to obtain the pure steroisomer of the compound of the present invention.

The compounds and processes of the present invention will be better understood by reference to the following Examples, which are intended as an illustration of and not a limitation upon the scope of the invention. Further, all citations herein are incorporated by reference.

Compounds of the invention were named by ACD/ChemSketch version 5.01 (developed by Advanced Chemistry Development, Inc., Toronto, ON, Canada) or were given names consistent with ACD nomenclature. Alternatively, compounds were assigned names using ChemDraw Ultra 9.0 (or higher version) (Cambridgesoft). The practice of assigning names to chemical compounds from structures, and of assigning chemical structures from given chemical names is well known to those of ordinary skill in the art.

Preparation of Compounds of the Present Invention

The compounds of this invention can be prepared by a variety of synthetic procedures. Representative procedures are shown in, but are not limited to, Schemes 1-11.

Scheme 1

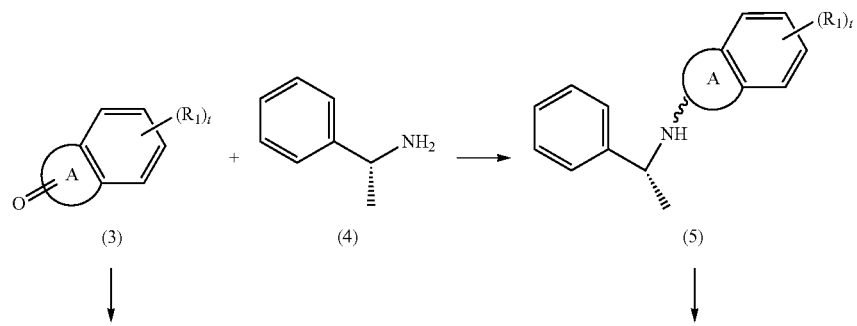

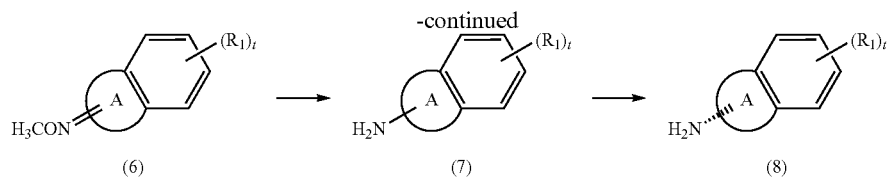

As outlined in Scheme 1, ketone containing compounds of formula (3) may be converted into compounds of formula (8) which are used in the synthesis of compounds of formula (1). Compounds of formula (3) when heated in the presence of a compound of formula (4) or similar chiral amine containing compound in toluene under Dean-Stark conditions with or without a catalytic amount of acid, followed by treatment with reducing conditions such as but not limited to sodium borohydride in ethanol will provide a compounds of formula (5). Compounds of formula (5) when treated with an atmosphere of hydrogen in the presence of a palladium catalyst such as palladium on carbon in solvents such as but not limited to methanol or ethanol with our without a catalytic amount of an acid such as acetic acid will provide compounds of formula (8) wherein $R_1$ is as defined in formula (1).

Alternatively, compounds of formula (3) when treated with an hydroxylamine or O-substituted hydroxylamines such as, but not limited to methoxyamine, in the presence of a solvent such as, but not limited to, pyridine or mixtures of ethanol and pyridine at a temperature from about room temperature to about 50° C. will provide oximes of formula (6). Oximes of formula (6) can be reduced in the presence of an atmosphere of hydrogen gas from about 40 to about 60 psi and a catalyst such as, but not limited to palladium on carbon at a temperature from about 50° C. to about 70° C. to provide compounds of formula (7). Compounds of formula (7) made through this method exist as a mixture of enantiomers that may be resolved by fractional crystallization when converted to salt with chiral carboxylic acid. Chiral carboxylic acids useful in forming salts with compounds of formula (7) include chiral amino acids such as, but not limited to, N-acetyl-(D)-leucine and N-tert-butyloxycarbonyl phenylalanine. The fractional crystallization of compounds of formula (7) with chiral carboxylic acids will provide after neutralization the individual isomers of (R) or the (S) form of the amine of formula (8).

Scheme 2

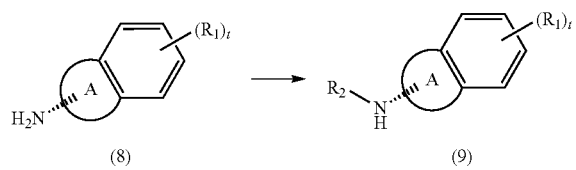

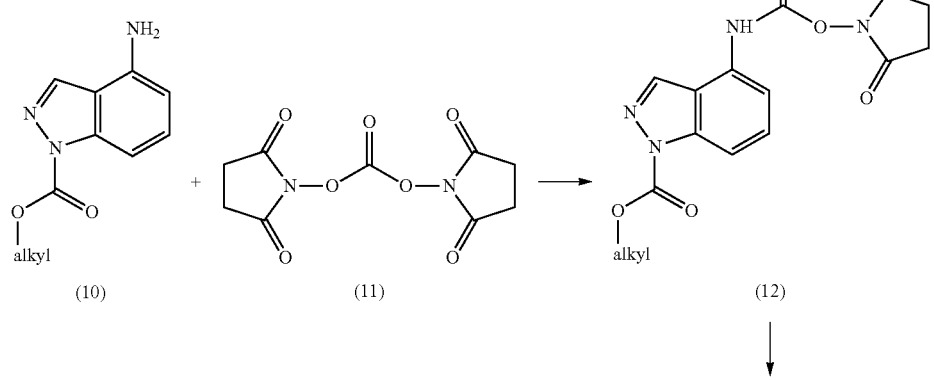

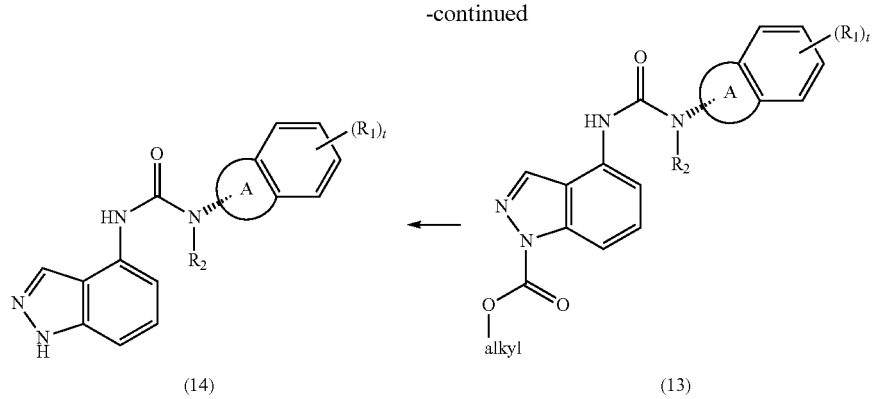

(14) (13)

Ureas of general formula (14) wherein $R_1$ and $R_2$ are as defined in formula (I) can be prepared as described in Scheme 2. Indazoles of general formula (10), prepared using the procedures as described in Example 56C, when treated with a compound of formula (11), in solvents such as but not limited to acetonitrile will provide a compound of formula (12). Compounds of formula (12) when treated with compounds of formula (9) in the presence of a base such as but not limited to diisopropylethylamine will provide ureas of formula (13). Typical solvents include but are not limited to acetonitrile or N,N-dimethylformamide. Ureas of general formula (13) when treated with sodium hydroxide or potassium hydroxide will provide indazoles of general formula (14). Typical solvents include but are not limited to methanol, ethanol and mixtures of solvents such as N,N-dimethylformamide and methanol. Compounds of formula (13) and of formula (14) described in Scheme 2 are drawn to represent chiral compounds which are the product of using the chiral compound of formula (9).

Alternatively, the use of racemic compounds of formula (7) in this synthetic pathway will produce racemic mixtures of compounds of formula (13) and racemic mixtures of compounds of formula (14).

Alternatively, compounds of formula (10) can be treated with phosgene or triphosgene and 4-dimethylaminopyridine in a solvent such as, but not limited to, dichloromethane, followed by treatment with amines of general formula (9) in a solvent such as, but not limited to, toluene or tetrahydrofuran or a combination thereof to provide ureas of general formula (13) wherein $R_2$ is hydrogen or heterocyclealkyl.

It is also known to one skilled in the art that compounds of formula (10) can be treated with trichloroacetyl chloride and a base such as, but not limited to, triethylamine in a solvent such as dichloromethane to provide trichloroacetamides, which in turn can be treated with amines of formula (9) and a non-nucleophilic base such as, but not limited to, 1,8-diazabicyclo[5.4.0]undec-7-ene in a solvent such as, but not limited to, acetonitrile, to provide ureas of general formula (13) wherein $R_2$ is hydrogen or heterocyclealkyl.

Compounds of formula (9) wherein $R_2$ is heterocyclealkyl can be obtained from amines of formula (8) by treatment with halides of formula $R_2X$ wherein X is Cl, Br or I, in the presence of a base such as but not limited to sodium carbonate or potassium carbonate, optioanally in the presence of catalytic amount of tetrabutylammonium iodide. The reaction is generally performed in solvents such as but not limited to N,N-dimethylformamide, methanol, ethanol, and mixtures thereof.

Compounds of formula (13) wherein $R_2$ is heterocyclealkyl can also be prepared from compounds of formula (13) wherein $R_2$ is hydrogen employing the reaction conditions for the transformation of compounds of formula (8) to compounds of formula (9).

Scheme 3

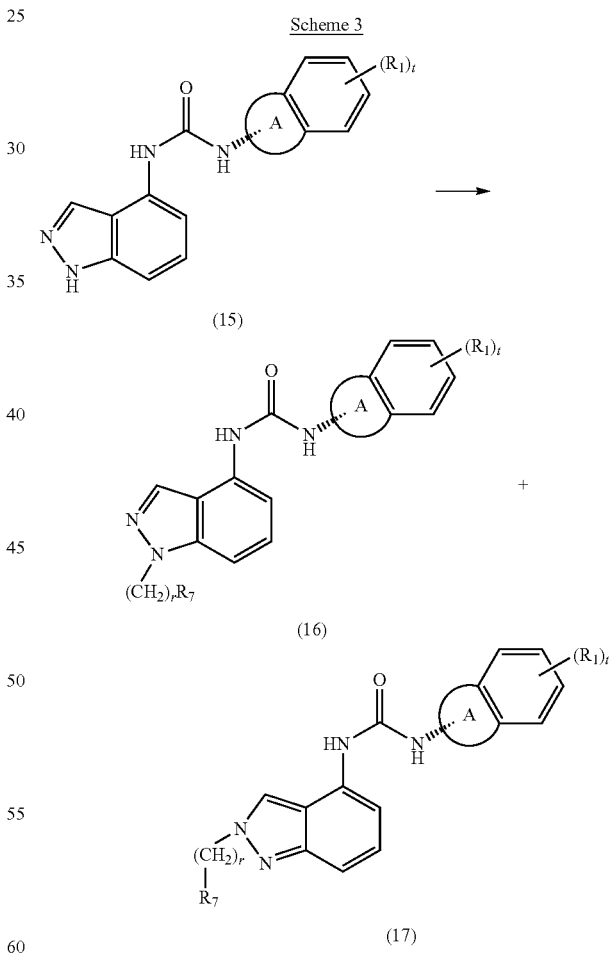

Compounds of formula (16) and (17) wherein r, $R_1$ and $R_7$ are as defined in formula (1) can be obtained from compounds of formula (15) by treatment with halides of formula $R_7(CH_2)_rX$, wherein X is Cl, Br or I, in the presence of a base such as but not limited to potassium carbonate, sodium carbonate or sodium hydride, and optionally in the presence of tetrabutyl ammonium iodide. The reaction is generally conducted in a solvent such as, but not limited to N,N-dimethylformamide, and at a temperature from about room temperature to about 100° C. The two regioisomers obtained can be separated using purification techniques such as but not limited to column chromatography on silica gel.

The compounds of formula (15), (16) and (17) are drawn to represent chiral compounds in this Scheme are for clarity purposes only. The same synthetic strategy may be carried out with the racemic compound of formula (15), which will produce the racemic mixtures of compounds of formula (16) and of formula (17). Similarly, the following schemes also are depicting using a chiral starting material but alternatively when carried out using a racemic mixture of a starting material or the opposite enantiomer will produce a racemic mixture of products or the opposite enantiomeric product, respectively.

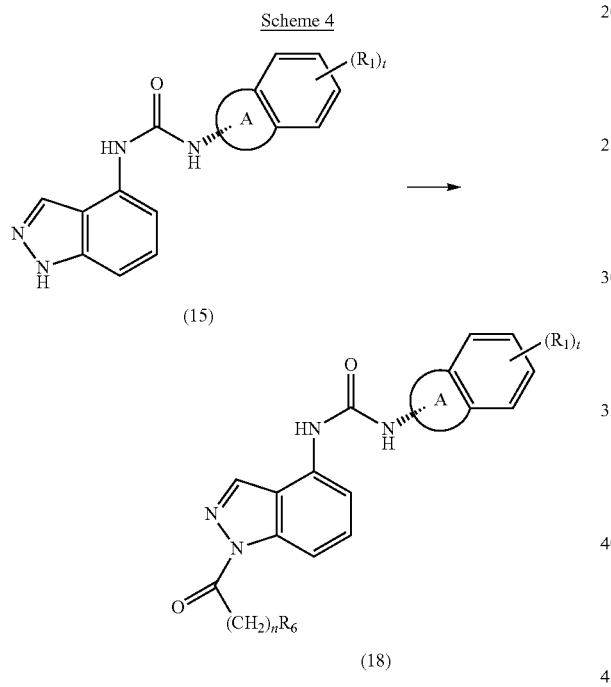

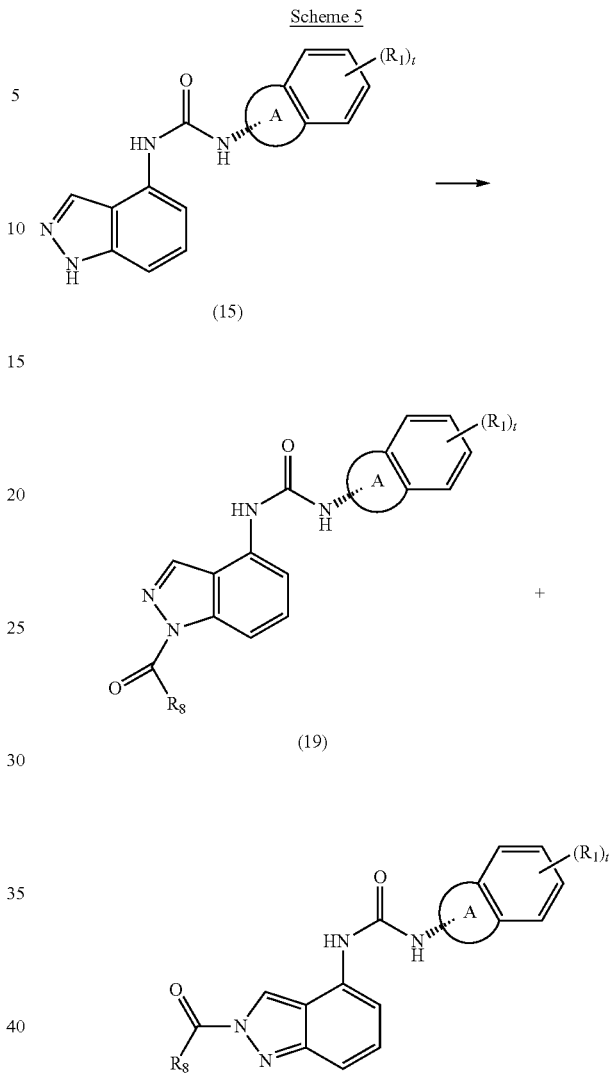

Compounds of formula (18) wherein n, $R_1$ and $R_6$ are as defined in formula (1) can be synthesized as outlined in Scheme 4. Acyl chlorides of formula $R_6(CH_2)_nCOCl$, or anhydrides such as, but not limited to, glutaric anhydride, succinic anhydride or acetic anhydride, purchased or prepared using methodologies known to one skilled in the art, and an amine such as, but not limited to triethylamine, pyridine or mixture thereof, when treated with imidazoles of formula (15), provides compounds of formula (18). The reaction can be conducted with or without a solvent at about room temperature, for a period of about 1 hour to about 5 days. Example of a solvent that can be employed includes, but not limited to, tetrahydrofuran.

Alternatively, compounds of formula (18) can also be obtained from compounds of formula (15) by treatment with acids of formula $R_6(CH_2)_nCOOH$, purchased or prepared by known methodologies, in the presence of a coupling agent such as, but not limited to, N,N'-dicyclohexylcarbodiimide. The reaction can be conducted at ambient temperature and in a solvent such as, but not limited to, dichloromethane, tetrahydrofuran, N,N-dimethylformamide, or mixture thereof.

Compounds of formula (15) can be transformed to compounds of formula (19) and (20) wherein $R_1$ and $R_8$ are as defined in formula (1) as shown in Scheme 5.

Treatment of compounds of formula (15) and carbonyl chlorides of formula $R_8COCl$ wherein $R_8$ is either $N(R_{8a})(R_{8b})$ or a heterocycle wherein the ring nitrogen atom is attached to the carbonyl moiety of the carbonyl chloride, followed by separation of the two regioisomers employing known purification technique such as but not limited to column chromatograph on silica gel, furnished compounds of formula (19) or (20). The reaction can be performed in a solvent such as but not limited to N,N-dimethylformamide, and in the presence of a base such as but not limited to sodium hydride. Treatment of compounds of formula (15) with carbonyl chlorides of formula $R_8COCl$ wherein the carbonyl moiety is appended to the carbon atom of the heterocycle ring afford compounds of formula (19) under the forgoing reaction conditions.

Carbonyl chlorides of formula $R_8COCl$ can be purchased or prepared from acids of formula $R_8COOH$ with thionyl chloride in the presence of catalytic amount of N,N-dimethylformamide, at a temperature of about room temperature, in a solvent such as, but not limited to, dichloromethane.

US 8,232,309 B2

21 22

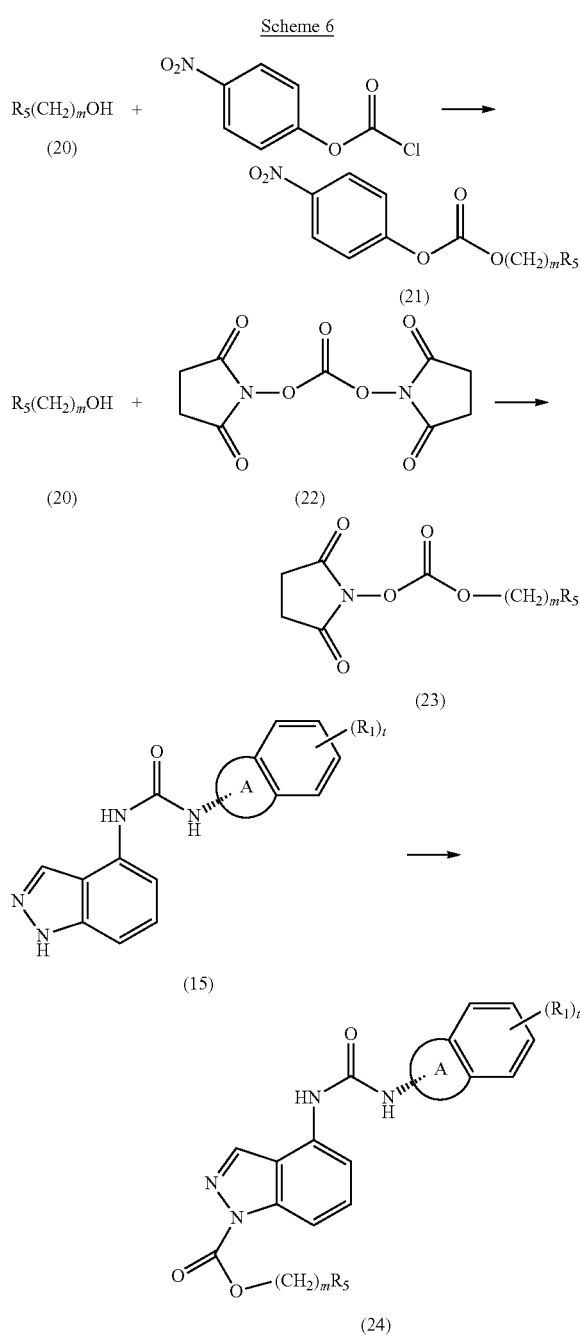

Scheme 6

(20) (21) (22) (23) (15) (24)

Compounds of formula (24) wherein $R_1$, $R_5$ and m are as defined in formula (I) can be prepared as outlined in Scheme 6.

Compounds of formula (15) when treated with compounds of formula (21) or (23) and a base such as but not limited to potassium tert-butoxide, in a solvent such as, but not limited to, N,N-dimethylformamide, at a temperature from about 0° C. to about room temperature, provides compounds of formula (24).

Alternatively, compounds of formula (24) can be obtained by treating compounds of formula (15) with chloroformates of formula $R_5(CH_2)mOC(O)Cl$ (purchased or prepared by known methodologies) in the presence of a base such as but not limited to 4-methylmorpholine, in a solvent such as, but not limited to, tetrahydrofuran.

Compounds of formula (21) or (23) can be prepared from alcohols of formula (20), by treatment with 4-nitrophenyl chloroformate or carbonate of formula (22) respectively, in the presence of a base such as, but not limited to, triethylamine or pyridine, in a solvent such as, but not limited to, dichloromethane or acetonitrile.

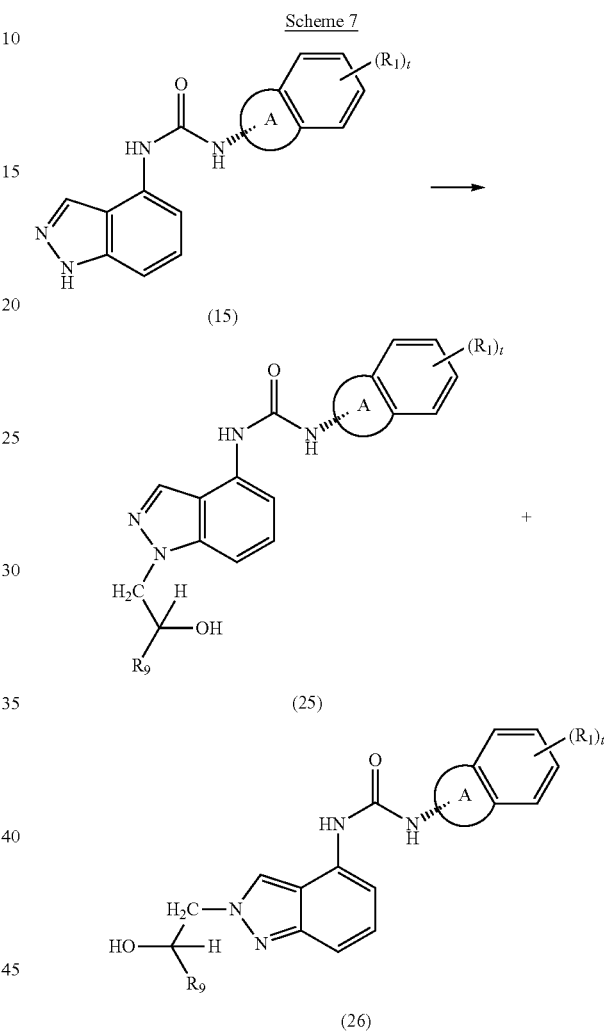

Scheme 7

(15) (25) (26)

Compounds of formula (25) or (26) wherein $R_1$ and $R_9$ are as defined in formula (I), can be prepared from compounds of formula (15), by treatment with substituted oxiranes (prepared by known methodologies or purchased) and a base such as, but not limited to, sodium tert-butoxide, sodium carbonate or potassium carbonate. The two regioisomers obtained can be separated by column chromatography or other purification techniques known to one skilled in the art. The reaction can be conducted at an elevated temperature from about 70° C. to about 120° C., in a solvent such as, but not limited to, methanol, ethanol, or acetonitrile.

It is understood that Schemes 2-7 depicting chiral compounds is done only for illustrative purposes only, and that the use of a racemic mixture of one starting material or the opposite enantiomer will produce a racemic mixture of products or the opposite enantiomeric product, respectively.

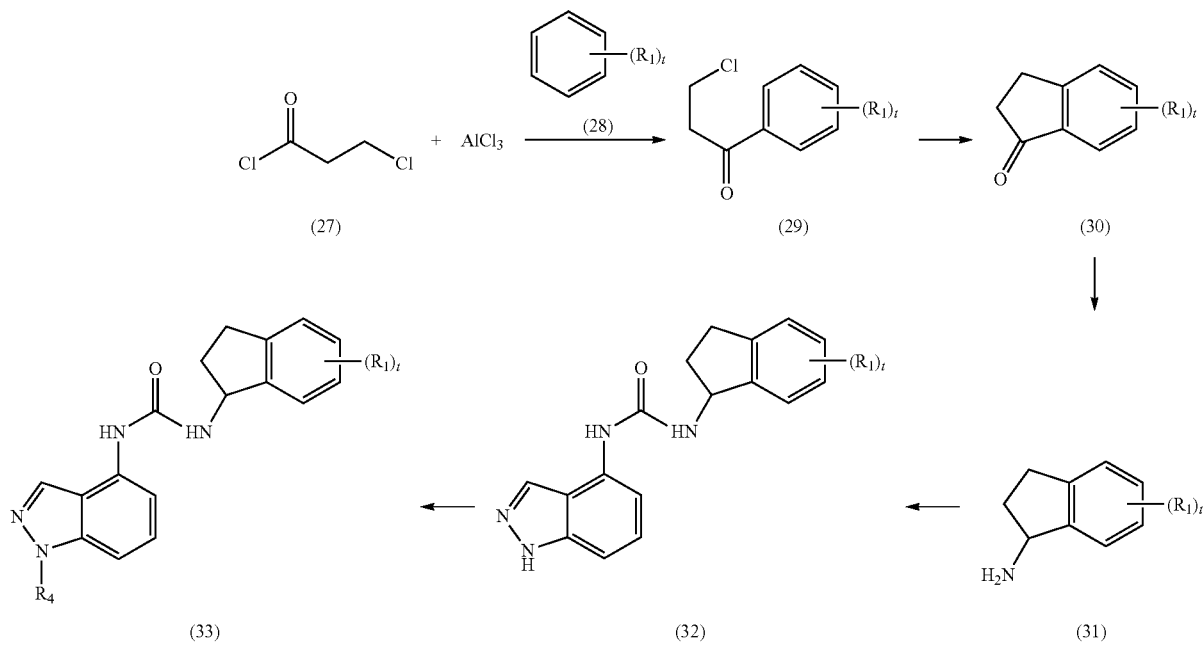

More specifically, compounds of the present invention which contain an amino-indane moiety may be prepared as outlined in Scheme 8. For example, chloropropionyl chloride when treated with aluminum chloride in a solvent such as but not limited to methylene chloride followed by the addition of a compound of formula (28) will provide a compound of formula (29). Compounds of formula (29) when treated with concentrated sulfuric acid or poly phosphoric acid followed by heating will provide compounds of formula (30). Compounds of formula (30) when treated according to the procedure outlined in Scheme 1 will provide amines of formula (31). Furthermore compounds of formula (31) when treated according to the procedures outlined in Scheme 2 will provide compounds of formula (32). Compounds of formula (32) when treated according to the procedures outlined in Scheme 3-5 will provide compounds of formula (33) which are representative of compounds of the present invention.

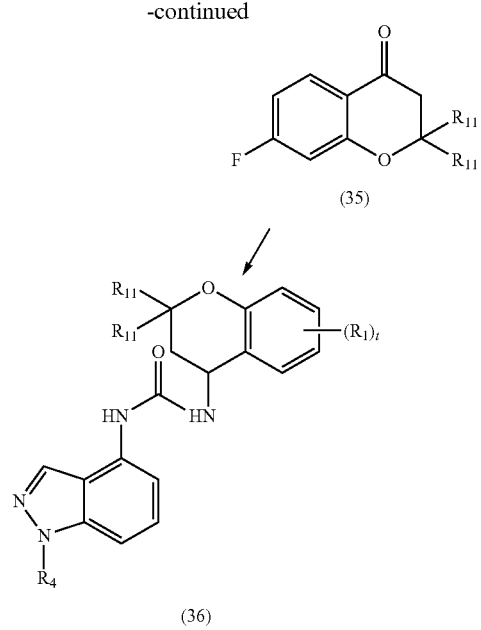

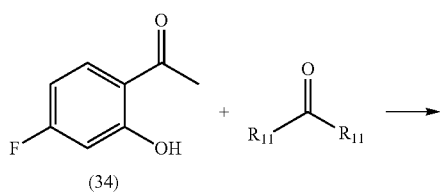

As outlined in Scheme 9, compounds of formula (34) when treated with a ketone substituted with $R_{11}$, wherein each occurance of $R_{11}$ are independently hydrogen, alkyl or aryl, or two $R_{11}$ groups that are attached to a single carbon atom or two adjacent carbon atoms together form a cycloalkyl ring; and a base such as but not limited to pyrrolidine in a solvent such as but not limited to toluene heated to reflux containing a Dean-Stark trap will provide compounds of formula (35). Compounds of formula (35) when treated according to the procedures outlined in Schemes 1-5 will provide compounds of formula (33), which are representative of compounds of the present invention.

Scheme 10

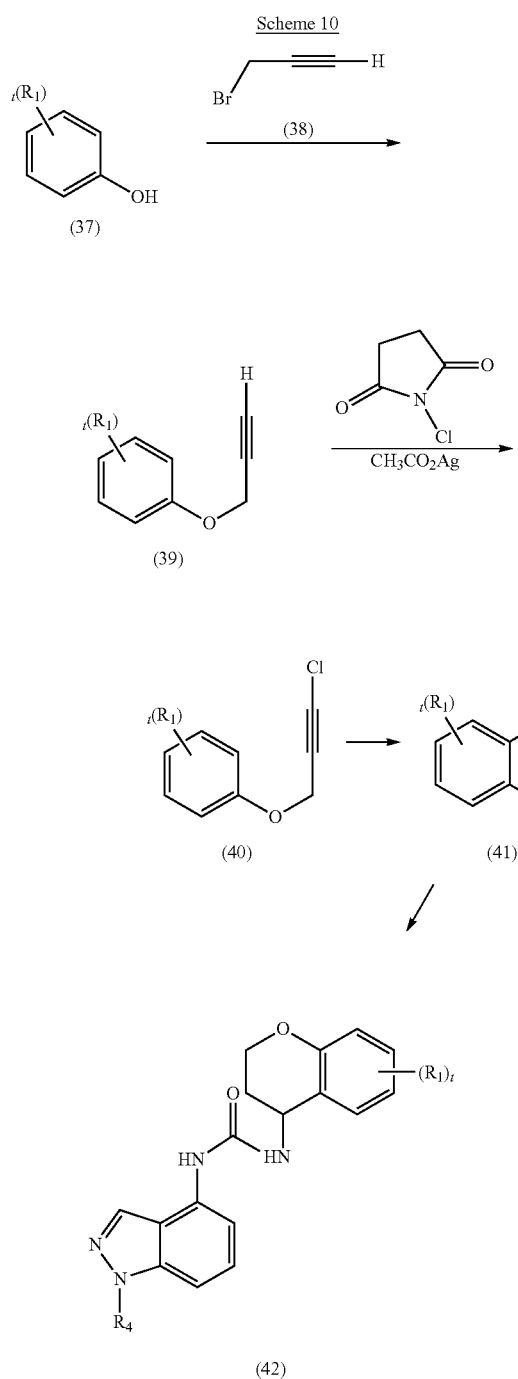

Scheme 11

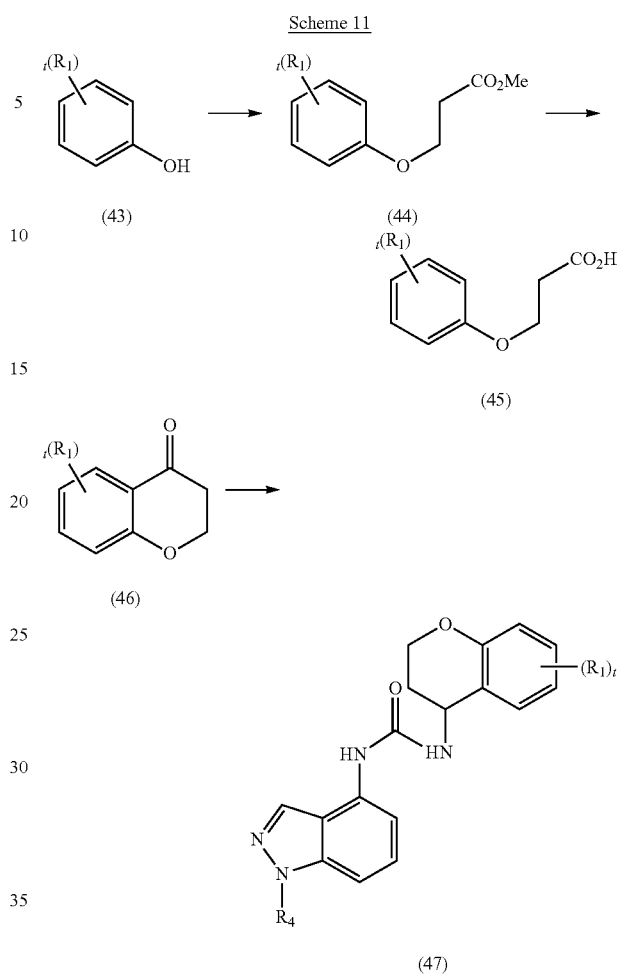

As shown in Scheme 10, compounds of formula (37), wherein $R_1$ and t are defined in formula(I) when treated with propargyl bromide in the presence of a base such as but not limited to potassium carbonate in a solvent such as but not limited to acetonitrile will provide compounds of formula (39). Compounds of formula (39) when treated with N-chlorosuccinimide and silver acetate in a solvent such as but not limited to acetone with heating will provide compounds of formula (40). Compounds of formula (40) when treated with ethylene glycol at reflux will provide compounds of formula (41). Compounds of formula (41) when treated according to the procedures outlined in Schemes 1-5 will provide compounds of formula (42)

As outlined in Scheme 11, compounds of formula (43) wherein $R_1$ and t are defined in formula (I), when treated with a base such as cesium carbonate in acetonitrile or sodium hydride in DMF followed by the treatment with methyl 3-bromopropionate will provide compounds of formula (44). Compounds of formula (44) when treated with sodium, lithium or potassium hydroxide in an aqueous alcoholic solvent will provide compounds of formula (45). Compounds of formula (45) when heated in the presence of polyphosphoric acid will provide compounds of formula (46). Compounds of formula (46) when treated according to conditions outlined in Schemes 1-5 will provide compounds of formula (47), which are representative of compounds of the present invention.

It is understood that the schemes described herein are for illustrative purposes and that routine experimentation, including appropriate manipulation of the sequence of the synthetic route, protection of any chemical functionality that are not compatible with the reaction conditions and the removal of such protecting groups are included in the scope of the invention.

It is understood that Schemes 8-11 depicting racemic mixtures of compounds is done only for illustrative purposes only, and that the use of a single enantiomeric starting material will produce a single enantiomeric product.

The following Examples are intended as an illustration of and not a limitation upon the scope of the invention as defined in the appended claims.

EXAMPLE 2

N-[(1R)-5-tert-butyl-2,3-dihydro-1H-inden-1-yl]-N'-[1-(2-morpholin-4-ylethyl)-1H-indazol-4-yl]urea

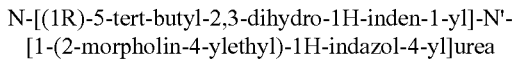

To a solution of compound from Example 56J (150 mg, 0.43 mmol) in 2 ml dimethylformamide was added potassium carbonate (180 mg, 1.3 mmol) and 4-(2-chloro-ethyl)-morpholine hydrochloride (121 mg, 0.65 mmol). The reaction was stirred for eleven days at ambient temperature. At this point, a catalytic amount (10 mg) of tetrabutylammonium iodide was added, and the reaction continued for 16 hours longer. The reaction mixture was diluted with water and filtered. The filtercake was then purified by chromatography on silica gel, using 5% ethanol/ethyl acetate as solvent, to give 92 mg of the title compound. $^1$H NMR (300 MHz, DMSO-d$_6$) δ ppm 8.56 (s, 1 H), 8.02 (s, 1 H), 7.70 (d, J=7.12 Hz, 1 H), 7.17-7.32 (m, 5 H), 6.68 (d, J=7.80 Hz, 1 H), 5.15 (m, 1 H), 4.46 (t, J=6.61 Hz, 2H, 3.44-3.53 (m, 4 H), 2.87-2.79 (m, 4 H), 2.38-2.52 (m, 5 H), 1.76-1.90 (m, 1 H), 1.28 (s, 9 H). MS (ESI) m/e 462 (M+H)$^+$. Calcd. For C$_{27}$H$_{35}$N$_5$O$_2$.0.4H$_2$O: C69.17, H 7.70, N 14.94; Found C 69.39, H 7.78, N 14.95.

EXAMPLE 3

2-{4-[({[(1R)-5-tert-butyl-2,3-dihydro-1H-inden-1-yl]amino}carbonyl)amino]-1H-indazo-1-yl}-2-oxo-ethyl acetate To a solution of compound from Example 56J (1.05 g, 3 mmol) in 10 ml pyridine and 1.5 ml triethylamine was added acetoxyacetyl chloride (0.54 ml, 0.68 g, 5 mmol). The reaction was stirred at ambient temperature for four days and the solvent was removed under reduced pressure. The residue was purified twice by chromatography on silica gel, using 25% to 40% ethyl acetate/hexane, to give 0.26 g of the title compound. $^1$H NMR (300 MHz, DMSO-d$_6$) δ ppm 8.46 (s, 1 H) 8.90 (s, 1 H), 7.91 (d, J=7.80 Hz, 1 H), 7.80 (d, J=8.14 Hz, 1 H), 7.54 (t, J=8.14 Hz, 1 H), 7.25-7.37 (m, 3 H), 6.71 (d, J=8.14 Hz, 1 H), 5.49 (s, 2 H), 5.17 (m, 1 H), 2.89-3.10 (m, 1 H), 2.74-2.88 (m, 1 H), 2.36-2.52 (m, 1 H), 2.19 (s, 3 H), 1.71-1.96 (m, 1 H), 1.27 (s, 9 H). MS (ESI) m/e 489 (M+H)$^{30}$. Calcd. For C$_{25}$H$_{28}$N$_4$O$_4$: C 66.95, H 6.29, N 12.49; Found C 66.74, H 6.43, N 12.28.

EXAMPLE 4 methyl 4-({[[(1R)-5-tert-butyl-2,3-dihydro-1H-inden-1-yl](2-morpholin-4-ylethyl)amino]carbonyl}amino)-1H-indazole-1-carboxylate

EXAMPLE 4A

N-[(1R)-5-tert-butyl-2,3-dihydro-1H-inden-1-yl]-N-(2-morpholin-4-ylethyl)amine

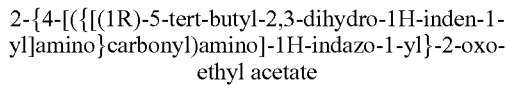

4-(2-Chloro-ethyl)-morpholine hydrochloride (0.56 g, 3 mmol), compound from Example 56K (1.08 g, 3 mmol), and sodium carbonate (1.06 g, 10 mmol) were suspended in 5 ml of ethanol and heated to reflux for four hours. The reaction mixture was then cooled, stirred for two days at ambient temperature, and diluted with water. The aqueous solution was extracted with diethyl ether, and the combined organic layers were dried with magnesium sulfate. The solvent was removed under vacuum to give 0.85 g crude title compound as an oil that was used without further purification.

EXAMPLE 4B methyl 4-({[[(1R)-5-tert-butyl-2,3-dihydro-1H-inden-1-yl](2-morpholin-4-ylethyl)amino]carbonyl}amino)-1H-indazole-1-carboxylate

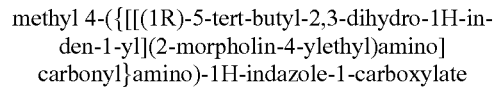

Step A

The product of Example 56C (1.9 g, 10 mmol) and disuccinimidylcarbonate (2.8 g, 11 mmol) in acetonitrile (100 mL) was stirred for 48 hours under nitrogen atmosphere. The solid was isolated by filtration, washed with acetonitrile (10 mL) and dried under vacuum at ambient temperature to give an off-white solid (2.56 g, 77%).

Step B:

Example 4A (0.85 g 2.8 mmol) and intermediate from Step A of Example 4B (0.66 g, 2 mmol) were dissolved in 5 ml dimethylformamide, and diisopropylethylamine (0.39 g, 0.52 ml, 3 mmol). The reaction was stirred at ambient temperature for 16 hours, then diluted with water and filtered. The solid collected was purified via flash chromatography using a gradient of 35% to 50% ethyl acetate in hexanes. After evaporation of solvent, the purified product was further dried by the addition of toluene followed by evaporation under vacuum, giving 0.70 g of title compound. $^1$H NMR (300 MHz, DMSO-d$_6$) δ ppm 8.27 (s, 1 H), 7.83 (d, J=8.48 Hz, 1 H), 7.55 (t, J=8.14 Hz, 1 H), 7.37 (d, J=7.46 Hz, 1 H), 7.11-7.33 (m, 4 H), 5.76 (t, J=7.97 Hz, 1 H), 4.04 (s, 3 H), 3.47-3.51 (m, 4 H), 3.11-3.42 (m, 4 H), 2.96-3.02 (m, 1 H), 2.71-2.89 (m, 1H), 2.33-2.47 (m, 5 H), 2.30 (s, toluene, 1.2 H), 1.89-2.14 (m, 1 H), 1.29 (s, 9 H). MS (ESI) m/e 520 (M+H)$^+$. Calcd. For C$_{29}$H$_{37}$N$_5$O4.0.4toluene.0.3H$_2$O: C 67.97, H 7.32, N 12.46; Found C 68.07, H 7.05, N 12.41.

EXAMPLE 5

N-[(1R)-5-tert-butyl-2,3-dihydro-1H-inden-1-yl]-N'-1H-indazol-4-yl-N-(2-morpholin-4-ylethyl)urea

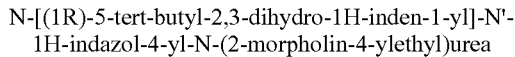

Example 4B (0.49 g, 0.94 mmol) was dissolved in a minimum amount of methanol. 1 ml of 5M sodium hydroxide in methanol was added, and the reaction stirred at ambient temperature for one hour. The reaction mixture was then diluted with water, and the product collected by filtration. Tituration with diethyl ether followed by drying under vacuum gave 0.35 g of the title compound. $^1$H NMR (300 MHz, DMSO-d$_6$) δ ppm 12.94 (s, 1 H), 9.38 (s, 1H), 7.80 (s, 1 H), 6.83-7.53 (m, 6 H), 5.73 (t, J=7.97 Hz, 1 H), 3.48-3.51 (m, 4 H), 3.38-3.48 (m,1H), 3.18-3.24 (m, 1H), 2.96-3.01 (m, 1H), 2.80-2.86 (m, 1H), 2.40-2.56 (m, 7H), 1.96-2.03 (m, 1H), 1.30 (s, 9 H). MS (ESI) m/e 462 (M+H)$^+$. Calcd. For C$_{27}$H$_{35}$N$_5$O$_2$.0.3tetrahydrofuran.1H$_2$O: C 69.74, H 7.93, N 14.42; Found C 69.70, H 7.73, N 14.30.

EXAMPLE 6

N-{1-[(benzyloxy)acetyl]-1H-indazol-4-yl}-N'-[(1R)-5-tert-butyl-2,3-dihydro-1H-inden-1-yl]urea

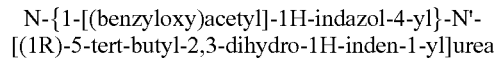

To a solution of compound from Example 56J (1.05 g, 3 mmol) in 10 ml pyridine and 1.5 ml triethylamine was added benzyloxy-acetyl chloride (1 ml, 1.11 g, 6 mmol). The reaction was stirred at ambient temperature for three days and the solvent was removed under reduced pressure. The residue was dissolved in ethyl acetate, washed with water, the organic layer dried with magnesium sulfate, and the solvent removed under reduced pressure. The residue was purified by chromatography on silica gel, using 2% methanol in methylene chloride, then titurated with 1:1 ether:hexanes, to give 1.19 g of the title compound. $^1$H NMR (300 MHz, DMSO-d$_6$) δ ppm 8.86 (s, 1 H), 8.39 (s, 1 H), 7.86-7.94 (m, 2 H), 7.54 (t, J=8.14 Hz, 1 H), 7.30-7.45 (m, 6 H), 7.27 (s, 2 H), 6.70 (d, J=7.80 Hz, 1 H), 5.16 (m, 1 H), 5.02 (s, 2 H), 4.71 (s, 2 H), 2.91-3.01 (m, 1 H), 2.77-2.88 (m, 1 H), 2.41-2.49 (m, 1 H), 1.85 (dd, J=12.55, 7.80 Hz, 1 H), 1.28 (s, 9 H). MS (ESI) m/e 497 (M+H)$^+$. Calcd. For C$_{30}$H$_{32}$N$_4$O$_3$: C 72.56, H 6.49, N 11.28; Found C 72.42, H 6.52, N 11.02.

EXAMPLE 7

N-[(1R)-5-tert-butyl-2,3-dihydro-1H-inden-1-yl]-N'-[1-(methoxyacetyl)-1H-indazol-4-yl]urea The title compound was prepared using the procedure as described in Example 6, substituting methyloxy-acetyl chloride for benzyloxy-acetyl chloride. $^1$H NMR (300 MHz, DMSO-d6) δ ppm 8.86 (s, 1 H), 8.40 (s, 1 H), 7.88 (dd, J=10.51, 8.14 Hz, 2 H), 7.53 (t, J=8.14 Hz, 1 H), 7.24-7.32 (m, 3 H), 6.70 (d, J=7.80 Hz, 1 H), 5.16 (q, J=7.23 Hz, 1 H), 4.90 (s, 2 H), 3.45 (s, 3 H), 2.96 (m, 1 H), 2.82 (m, 1 H), 2.41-2.48 (m, 1 H), 1.79-1.91 (m, 1 H), 1.28 (s, 9H). MS (ESI) m/e 421 (M+H)$^+$. Calcd. For C$_{24}$H$_{28}$N$_4$O$_3$·0.2H$_2$O: C 67.97, H 6.75, N 13.21; Found C 68.03, H 6.68, N 13.13.

EXAMPLE 8

4-{4-[({[(1R)-5-tert-butyl-2,3-dihydro-1H-inden-1-yl]amino}carbonyl)amino]-1H-indazol-1-yl}-4-oxobutanoic acid To a solution of Example 56J (2.09 g, 6 mmol) in 50 ml tetrahydrofuran and 6 ml triethylamine was added succinic anhydride (1.20 g 12 mmol). The reaction was stirred 7 days at ambient temperature, then diluted with water and ethyl acetate, made acidic with 1N aqueous HCl, and extracted with ethyl acetate. The combined organic layers were dried with magnesium sulfate and the solvent removed under reduced pressure to give 2.95 g of the title compound. $^1$H NMR (300 MHz, DMSO-d$_6$) δ ppm δ12.21 (s, 1 H), 8.87 (s, 1 H), 8.42 (s, 1 H), 7.88 (m, 2 H), 7.50 (t, J=8.14 Hz, 1 H), 7.04-7.37 (m, 3 H), 6.72 (d, J=7.80 Hz, 1 H), 5.17 (m, 1 H), 4.03 (q, Ethyl acetate), 3.37-3.42 (m, 2 H), 2.89-3.06 (m, 1 H), 2.75-2.89 (m, 1 H), 2.67-2.71 (m, 2H), 2.33-2.46 (m, 1 H), 1.99 (t, Ethyl acetate), 1.67-1.95 (m, 1 H), 1.28 (s, 9 H), 1.17 (t, Ethyl acetate). MS (ESI) m/e 449 (M+H)$^+$. Calcd. For C$_{25}$H$_{28}$N$_4$O$_4$·0.4ethyl acetate·1.2H$_2$O: C 63.22, H 6.70, N 11.09; Found C 63.06, H 6.26, N 10.94.

EXAMPLE 9

N-[(1R)-5-tert-butyl-2,3-dihydro-1H-inden-1-yl]-N'-[1-(N,N-dimethylglycyl)-1H-indazol-4-yl]urea, trifluoroacetic acid salt To a solution of Example 56J (3.48 g, 10 mmol) in 33 ml pyridine and 10 ml triethylamine was added dimethylamino-acetyl chloride hydrochloride (4.74 g, 30 mmol). The reaction was stirred at ambient temperature for two days and the solvent was removed under reduced pressure. The residue was dissolved in ethyl acetate, washed with water and saturated aqueous sodium bicarbonate, the organic layer dried with magnesium sulfate, and the solvent removed under reduced pressure. The crude product obtained was purified using reverse-phase HPLC (acetonitrile-water with 0.1% trifluoroacetic acid as eleuent) to give the title compound. $^1$H NMR (300 MHz, DMSO-d$_6$) δ ppm 8.98 (s, 1 H), 8.54 (s, 1 H), 7.85-7.92 (m, 2 H), 7.60 (t, J=8.14 Hz, 1 H), 7.26-7.33 (m, 3 H), 6.75 (d, J=7.80 Hz, 1 H), 5.17 (m, 1 H), 4.99 (s, 2 H), 3.23-3.37 (s, 1H, under H$_2$O), 2.96 (s, 6 H), 2.91-3.01 (m, 1 H), 2.77-2.88 (m, 1 H), 1.82-1.91 (m, 1 H), 1.28 (s, 9 H). MS (ESI) m/e 434 (M+H)$^+$. Calcd. For C$_{25}$H$_{31}$N$_5$O$_2$·1.2trifluoroacetic acid: C 57.70, H 5.69, N 12.28; Found C 57.63, H 5.51, N 12.27.

EXAMPLE 10

N-[(1R)-5-tert-butyl-2,3-dihydro-1H-inden-1-yl]-N'-(1-glycoloyl-1H-indazol-4-yl)urea Example 6 (1.06 g, 2.1 mmol) was dissolved in 10 ml tetrahydrofuran and was then subjected to hydrogenolysis over palladium hydroxide (1.10 g of 20% Pd(OH)$_2$ on carbon, wet). The reaction was stirred at ambient temperature for 16 hours under a 50 psi hydrogen atmosphere. Filtration and removal of solvent under vacuum gave 0.54 g of title compound. $^1$H NMR (300 MHz, DMSO-d$_6$) δ ppm 8.85 (s, 1 H), 8.39 (s, 1 H), 7.88 (t, J=7.80 Hz, 2 H), 7.52 (t, J=8.14 Hz, 1 H), 7.25-7.37 (m, 3 H), 6.70 (d, J=7.80 Hz, 1 H), 5.43 (t, J=6.44 Hz, 1 H), 5.16 (q, J=7.35 Hz, 1 H), 4.87 (d, J=6.44 Hz, 2 H), 2.66-3.07 (m, 2 H), 2.35-2.48 (m, 1 H), 1.78-1.94 (m, 1 H), 1.22-1.32 (m, 9 H). MS (ESI) m/e 407 (M+H)$^+$

EXAMPLE 11

N-[(1R)-5-tert-butyl-2,3-dihydro-1H-inden-1-yl]-N'-1H-indazol-4-yl-N-(2-piperidin-1-ylethyl)urea

EXAMPLE 11A

((R)-5-tert-Butyl-indan-1-yl)-(2-piperidin-1-yl-ethyl)-amine

The title compound was prepared using the procedure as described in Example 4A, substituting 1-(2-chloro-ethyl)-piperidine hydrochloride for 4-(2-chloro-ethyl)-morpholine hydrochloride. The crude compound was used without further purification.

EXAMPLE 11B methyl 4-({[[(1R)-5-tert-butyl-2,3-dihydro-1H-inden-1-yl](2-piperidin-1-ylethyl)amino]carbonyl}amino)-1H-indazole-1-carboxylate The title compound was prepared using the procedure as described in Example 4B, substituting Example 11A for Example 4A. The crude product was purified using reverse-phase HPLC (acetonitrile-water with 0.1% trifluoroacetic acid as eleuent) to give 0.32 g of the desired compound. $^1$H NMR (300 MHz, DMSO-d$_6$) δ ppm 9.16 (s, 1 H), 8.97 (s,1 H), 8.34 (s, 1 H), 7.86 (d, J=8.48 Hz, 1 H), 7.46-7.65 (m,1 H), 7.30-7.42 (m, 2 H), 7.23 (d, J=7.80 Hz, 1H), 5.73 (t, J=7.80 Hz, 1 H), 4.04 (s, 3 H), 2.65-3.89 (m, 11 H), 2.49-2.65 (m, 1 H), 1.30-1.89 (m, 6 H), 1.30 (s, 9 H). MS (ESI) m/e 518 (M+H)$^+$.

EXAMPLE 11C

N-[(1R)-5-tert-butyl-2,3-dihydro-1H-inden-1-yl]-N'-1H-indazol-4-yl-N-(2-piperidin1-ylethyl)urea The title compound was prepared using the procedure as described in Example 5, substituting Example 11B for Example 4B. ¹H NMR (300 MHz, DMSO-d₆) δ ppm 12.89 (br s, 1 H), 10.06 (br s, 1 H), 7.86 (s, 1 H), 7.03-7.41 (m, 6 H), 5.77 (t, J=7.97 Hz, 1 H), 3.25-3.44 (m, 2 H), 3.06-3.22 (m, 1 H), 2.89-3.05 (m, 1 H), 2.69-2.89 (m, 1 H), 2.32-2.48 (m, 6 H), 1.83-2.06 (m, 1 H), 1.30-1.57 (m, 6 H), 1.29 (s, 9 H). MS (ESI) m/e 460 (M+H)⁺. Calcd For $C_{28}H_{37}N_5O \cdot 0.1H_2O \cdot 0.33NaCl$: C 69.96, H 7.80, N 14.57; Found C 69.90, H 7.80, N 14.37.

EXAMPLE 12

5-{4-[({[(1R)-5-tert-butyl-2,3-dihydro-1H-inden-1-yl]amino}carbonyl)amino]-1H-indazol-1-yl}-5-oxopentanoic acid To a solution of Example 56J (0.52 g, 1.5 mmol) in 7 ml tetrahydrofuran and 1.5 ml triethylamine was added glutaric anhydride (0.34 g 3 mmol). The reaction was stirred 5 days at ambient temperature, then was diluted with water and ethyl acetate, made acidic with 1N aqueous HCl, and extracted with ethyl acetate. The combined organic layers were dried with magnesium sulfate and the solvent removed under reduced pressure. The residue was found to contain a large amount of glutaric acid, which was removed by tituration with water to give 0.61 g of the title compound. ¹H NMR (300 MHz, DMSO-d₆) δ ppm 12.10 (br s, 1 H), 8.85 (s, 1 H), 8.39 (s, 1 H), 7.90 (d, J=4.75 Hz, 1 H), 7.87 (d, J=5.42 Hz, 1 H), 7.50 (t, J=8.14 Hz, 1 H), 7.23-7.35 (m, 2 H), 6.71 (d, J=8.14 Hz, 1 H), 5.09-5.27 (m, 1 H), 3.15-3.27 (t, J=7.46 Hz, 2H), 2.89-3.06 (m, 1 H), 2.73-2.89 (m, 1 H), 2.41-2.48 (m, 1 H), 2.37 (t, J=7.29 Hz, 2 H), 1.88-2.00 (m, 2 H), 1.77-1.89 (m, 1 H), 1.28 (s, 9 H). MS (ESI) m/e 463 (M+H)⁺. Calcd. For $C_{26}H_{30}N_4O_4 \cdot 0.4H_2O$: C 66.48, H 6.61, N 11.93; Found C 66.43, H 6.38, N 11.82.

EXAMPLE 13

2-(phosphonooxy)ethyl 4-[({[(1R)-5-tert-butyl-2,3-dihydro-1H-inden-1-yl]amino}carbonyl)amino]-1H-indazole-1-carboxylate To Example 14D (0.37 g, 0.6 mmol) in a 250 ml round bottom flask was added acetonitrile (40 ml) and 0.1% trifluoroacetic acid in water (40 ml) and the reaction was stirred at room temperature for 4 days. Every 24 hours 0.5 ml of trifluoroacetic acid was added. After four days, the reaction was concentrated to give a white powder in 84% yield. ¹H NMR (DMSO-d₆, 300 MHz); δ 1.28 (s, 9H), 1.74-1.91 (m, 2H), 2.41-2.54 (m, 1H), 2.77-3.38 (m, 2H), 4.18-4.23 (m, 2H), 4.60-4.63 (m, 2H), 5.13-5.20 (m, 1H), 6.68 (d, J=7.8 Hz, 1H), 7.24-7.28 (m, 2H), 7.50 (t, J=8.41, 16.18 Hz, 1H), 7.71 (d, J=8.48 Hz, 1H), 7.90 (d, J=8.27 Hz, 1H), 8.41 (s, 1H), 8.84 (s, 1H). MS (DCI/NH₃) m/z 517; Calc for $C_{24}H_{29}N_4O_7P$: C, 55.04; H, 5.74; N, 10.70. Found: C, 55.18; H, 5.50; N, 10.52.

EXAMPLE 14

2-[(di-tert-butoxyphosphoryl)oxy]ethyl 4-[({[(1R)-5-tert-butyl-2,3-dihydro-1H-inden-1-yl]amino}carbonyl)amino]-1H-indazole-1-carboxylate

EXAMPLE 14A

Carbonic acid 2-benzyloxy-ethyl ester 4-nitro-phenyl ester

To a 250 ml round bottom flask was added 2-benzyloxyethanol (7.54 g, 49.60 mmol) (Aldrich), 4-nitrophenyl chloroformate (10 g, 49.60 mmol) (Aldrich), dichloromethane (100 ml) followed by the addition of pyridine (5.89 g, 79.10 mmol) and the reaction was stirred at room temperature for 12 hours. The reaction was diluted with 200 ml of dichloromethane was washed with 1N HCl (100 ml), sat NaHCO₃ (100 ml), dried (Na₂SO₄) and concentrated in vacuo. The reaction was purified on SiO₂ and eluted with hexane/ethyl acetate 4/1 to provide a yellow solid (11.20 g) in 71% yield. ¹H NMR (CDCl₃, 300 MHz); δ ppm 3.70-3.80 (m, 2H), 4.30-4.57 (m, 2H), 4.61 (s, 2H), 7.26-7.40 (m, 7H), 8.26 (d, J=8.82 Hz, 2H); DCI/NH₃ m/z 318.00.

EXAMPLE 14B

2-(benzyloxy)ethyl 4-[({[(1R)-5-tert-butyl-2,3-dihydro-1H-inden-1-yl]amino}carbonyl)amino]-1H-indazole-1-carboxylate To a 250 ml round bottom flask was added Example 56J (5.0 g, 14.40 mmol), anhydrous N,N-dimethylformamide (40 ml) and 1M in tetrahydrofuran potassium tert-butoxide (17.30 ml) and the reaction was stirred at room temperature for 1 hour. To the reaction mixture was added Example 14A (5.50 g, 17.70 mmol) at 0° C. and the reaction was stirred for 12 hours while allowing to warm to room temperature. The reaction was poured into a separatory funnel and extracted with ethyl acetate (200 ml) and washed with H₂O (100 ml), brine (100 ml), dried (Na₂SO₄) and concentrated in vacuo. The mixture was purified on SiO₂ eluting with hexane/ethyl acetate 1/1 to provide a white solid (6.78 g) in 74% yield. ¹H NMR (DMSO-d₆, 300 MHz); δ ppm 1.27 (s, 9H), 1.74-1.84 (m, 1H), 2.50-2.60 (m, 1H), 2.73-2.93 (m, 3H), 3.61 (t, J=4.41, 9.16 Hz, 2H), 3.75-3.82 (m, 4H), 5.35-5.37 (m,1H), 7.13-7.38 (m, 7H), 7.70-7.73 (m, 2H), 7.90-7.94 (m, 1H), 8.32 (s, 1H); MS (DCI/NH₃) m/z 527.00.

EXAMPLE 14C

2-hydroxyethyl 4-[({[(1R)-5-tert-butyl-2,3-dihydro-1H-inden-1-yl]amino}carbonyl)amino]-1H-indazole-1-carboxylate In a 250 ml Parr shaker flask was added Example 14B (6.0 g, 11.40 mmol), 20% Pd/C, and ethanol (100 ml). The vessel was pressurized to 60 psi with H₂ gas and shaken at room temperature for 6 hours. The reaction was filter and concentrated in vacuo. The material was purified on SiO₂ with dichloromethane/CH₃OH (98/2) to give a white solid (4.18 g) in 84%. ¹H NMR (DMSO-d₆, 300 MHz); δ ppm 1.32 (s, 9H), 1.86-1.93 (m, 2H), 2.57-2.63 (m, 1H), 2.84-2.92 (m, 1H), 2.96-3.01 (m, 1H), 3.92-3.95 (m, 2H), 4.55-4.58 (m, 2H), 5.27-5.32 (t, J=7.12, 14.58, 1H), 7.28-7.31 (m, 2H), 7.52 (t, J=7.80, 16.28, 1H), 7.73 (d, J=7.72 Hz, 1H), 7.87 (d, J=8.48 Hz, 1H), 8.38 (s, 1H); MS (DCI/NH₃) m/z 437.00.

EXAMPLE 14D

2-[(di-tert-butoxyphosphoryl)oxy]ethyl 4-[({[(1R)-5-tert-butyl-2,3-dihydro-1H-inden-1-yl]amino}carbonyl)amino]-1H-indazole-1-carboxylate To Example 14C (1.60 g, 3.70 mmol) was added methylene chloride (25 ml), tetrahydrofuran (25 ml), tetrazole (0.77 g, 11.0 mmol), 4-(dimethylamino)pyridine (0.18 g, 1.50 mmol) and di-tert-butyl diisopropyl-phosphoramidite (2.04 g, 7.30 mmol) (Aldrich) and the reaction was stirred at room temperature for 2 hours. The reaction was then cooled to 0° C. and 30% hydrogen peroxide was added and the mixture was stirred for 2 hours at room temperature. The reaction was poured into a separatory funnel and washed with water, sat NaHCO$_3$, dried over Na$_2$SO$_4$ and concentrated in vacuo. The mixture was purified by HPLC with acetonitrile and 0.1% trifluoroacetic acid buffer to give a white solid in 48% yield. $^1$H NMR (CD$_3$OD, 300 MHz); δ ppm 1.32 (s, 9H), 1.45 (s, 18H), 1.83-1.95 (m, 2H), 2.52.66 (m, 1H), 2.82-2.90 (m, 1H), 3.92-3.06 (m, 1H), 4.35-4.40 (m, 2H), 4.73-4.84 (m, 2H), 5.29 (t, J=7.26, 14.68 Hz, 1H), 7.28-7.31 (m, 2H), 7.52 (t, J=8.13, 16.27 Hz, 1H), 7.54 (d, J=8.14 Hz, 1H), 7.76 (d, J=7.80 Hz, 1H), 8.37 (s, 1H); MS (DCI/NH$_3$) m/z 629.00; Calc for C$_{32}$H$_{245}$N$_4$O$_7$P: C, 60.44; H, 7.26; N, 8.81. Found: C, 60.45; H, 7.26; N, 8.68.

EXAMPLE 15

3-(phosphonooxy)propyl 4-[({[(1R)-5-tert-butyl-2,3-dihydro-1H-inden-1-yl]amino}carbonyl)amino]-1H-indazole-1-carboxylate

EXAMPLE 15A

Carbonic acid 3-benzyloxy-propyl ester 4-nitro-phenyl ester

To a 250 ml round bottom flask was added 3-benzyloxypropanol (8.24 g, 49.60 mmol) (Aldrich), 4-nitrophenyl chloroformate (10 g, 49.60 mmol) (Aldrich), dichloromethane (100 ml) followed by the addition of pyridine (5.89 g, 79.10 mmol) and the reaction was stirred at room temperature for 12 hours. The reaction was diluted with 200 ml of dichloromethane was washed with 1N HCl (100 ml), sat NaHCO$_3$ (100 ml), dried (Na$_2$SO$_4$) and concentrated in vacuo. The reaction was purified on SiO$_2$ and eluted with hexane/ethyl acetate 4/1 to provide a yellow oil (8.26) in 50% yield. $^1$H NMR (CDCl$_3$, 300 MHz); δ ppn 2.03-2.11 (m, 2H), 3.62 (t, J=6.0, 12.0 Hz, 2H), 4.43 (t, J=6.0, 12.0 Hz, 2H), 4.53 (s, 2H), 7.26-7.37 (m, 7H), 8.26 (d, J=9.0 Hz, 2H); MS (DCI/NH$_3$) m/z 332.0.

EXAMPLE 15B 3-(benzyloxy)propyl 4-[({[(1R)-5-tert-butyl-2,3-dihydro-1H-inden-1-yl]amino}carbonyl)amino]-1H-indazole-1-carboxylate To a 250 ml round bottom flask was added Example 56J (7.35 g, 21.10 mmol), anhydrous N,N-dimethylformamide (60 ml) and potassium tert-butoxide (1 M in tetrahydrofuran, 25.32 ml) and the reaction mixture was stirred at room temperature for 1 hour. To the reaction mixture was added Example 15A (7.0 g, 21.10 mmol) at 0° C., stirred for 12 hours while allowing to warm to room temperature. The reaction mixture was poured into a separatory funnel and extracted with ethyl acetate (500 ml) and washed with H$_2$O (200 ml), brine (200 ml), dried (Na$_2$SO$_4$) and concentrated in vacuo. The mixture was purified on silica gel and eluted with hexane/ethyl acetate 1/1 to provide a white solid (4.96 g) in 43% yield. $^1$H NMR (CDCl$_3$, 300 MHz); δ 1.27 (s, 9H), 1.72-1.87 (m, 1H), 2.07-2.21 (m, 2H), 2.51-2.61 (m, 1H), 2.73-2.94 (m, 3H), 3.64 (t, J=5.77, 16.95 Hz, 2H), 4.49-4.68 (m, 4H), 5.34-5.39 (m, 1H), 7.13-7.38 (m, 7H), 7.70-7.73 (m, 2H), 7.90-7.94 (m, 1H), 8.32 (s, 1H). DCI/NH$_3$ m/z 540.00.

EXAMPLE 15C 3-hydroxypropyl 4-[( {[(1R)-5-tert-butyl-2,3-dihydro-1H-inden-1-yl]amino}carbonyl)amino]-1H-indazole-1-carboxylate In a 250 ml Parr shaker flask was added product of Example 15B (2.2 g, 4.10 mmol), 20% Pd/C and ethanol (100 ml). The vessel was pressurized to 60 psi with H$_2$ gas and shaken at room temperature for 6 hours. The reaction was filtered and concentrated in vacuo. The material was purified on SiO$_2$ with dichloromethane/CH$_3$OH (98/2) to give a white solid (1.57 g) in 85%. $^1$H NMR (CDCl$_3$, 300 MHz); δ ppm 1.28 (s, 9H), 1.81-2.08 (m, 2H), 2.41-2.52 (m, 3H), 2.77-2.87 (m, 1H), 2.91-3.01 (m, 1H), 3.55-3.68 (m, 2H), 4.49 (t, J=4.43, 11.82 Hz, 2H), 5.13-5.20 (m, 1H), 7.22-7.27 (m, 2H), 7.50 (t, J=8.14, 16.28 Hz, 1H), 6.67 (d, J=9.13 Hz, 1H), 7.89 (d, J=8.14 Hz, 1H), 8.39 (s, 1H); MS (DCI/NH$_3$) m/z 451.00.

EXAMPLE 15D

3-[(di-tert-butoxyphosphoryl)oxy]propyl 4-[({[(1R)-5-tert-butyl-2,3-dihydro-1H-inden-1-yl]amino}carbonyl)amino]-1H-indazole-1-carboxylate To the product from Example 15C (1.49 g, 3.30 mmol) was added methylene chloride (50 ml), tetrazole (0.70 g, 9.90 mmol), 4-(dimethylamino)pyridine (0.16 g, 1.30 mmol) and di-tert-butyl diisopropyl-phosphoramidite (3.15 g, 9.90 mmol) (Aldrich) and the reaction was stirred at room temperature for 2 hours. The reaction was then cooled to 0° C. and 30% hydrogen peroxide was added and the mixture was stirred for 2 hours at room temperature. The reaction was poured into a seperatory funnel and washed with water, sat NaHCO$_3$, dried over Na$_2$SO$_4$ and concentrated in vacuo. The mixture was purified on SiO$_2$ with hexane/ethyl acetate (1/1) to give a white solid (2.12 g) in 97% yield. $^1$H NMR (CDCl$_3$, 300 MHz); δ ppm 1.22 (s, 9H), 1.30(s, 18H), 2.17-2.27 (m, 1H), 2.58-2.65 (m,1H), 2.81-2.94 (m, 1H), 3.20-3.51 (m, 2H), 3.72-3.78 (m, 2H), 4.12-4.18 (m, 2H), 4.59 (t, J=6,78, 13.22, 2H), 5.42 (t, J=7.46, 12.24 Hz, 1H), 7.19-7.32 (m, 2H), 7.45 (t, J=8.14, 16.24 Hz, 1H), 7.76 (d, J=8.48 Hz, 1H), 7.95 (d, J=7.80 Hz, 1H), 8.47 (s, 1H); MS (DCI/NH$_3$) m/z 642.00.

EXAMPLE 15E 3-(phosphonooxy)propyl 4-[({[(1R)-5-tert-butyl-2,3-dihydro-1H-inden-1-yl]amino}carbonyl)amino]-1H-indazole-1-carboxylate To the product from Example 15D (2.12 g, 3.30 mmol) in a 250 ml round bottom flask was added acetonitrile (40 ml) and 0.1% trifluoroacetic acid in water (40 ml) and the reaction was stirred at room temperature for 4 days. Every 24 hours 0.5 ml of trifluoroacetic acid was added until day four. The reaction was concentrated to give a white powder in 81% yield. $^1$H NMR (CDCl$_3$, 300 MHz); δ ppm 1.32 (s, 9H), 1.88-1.92 (m, 1H), 2.22-2.26 (m, 2H), 2.57-2.63 (m, 1H), 2.84-2.90 (m, 1H), 2.96-3.32 (m, 1H), 4.21 (m, 2H), 4.65 (t, J=6.11, 12.55Hz, 2H), 5.29 (t, J=7.46, 14.58 Hz, 1H), 7.28-7.31 (m, 3H), 7.52 (t, J=8.14, 16.28 Hz, 1H), 7.73 (d, J=7.45Hz, 1H), 7.83 (d, J=8.48Hz, 1H), 8.36 (s, 1H); MS (DCI/NH$_3$) m/z 531.00; Calc for C$_{25}$H$_{31}$N$_4$O$_7$P: C, 54.45; H, 5.59; N, 9.92. Found: C, 54.84; H, 5.88; N, 9.92.

EXAMPLE 16

N-[(1R)-5-tert-butyl-2,3-dihydro-1H-inden-1-yl]-N'-[1-(hydroxymethyl)-1H-indazol-4-yl]urea To a solution of compound from Example 56J (67 mg, 0.192 mmol) in 4 mL ethanol was added 0.5 mL of 37% aqueous formaldehyde solution. The mixture was stirred at room temperature for 3 days, and then was evaporated in vacuo. The crude product was purified by silica gel chromatography (96:4 dichloromethane:methanol, eluant) to afford a white solid, 24 mg (33%). $^1$H NMR ($d_6$-DMSO) δ ppm 8.60 (s, 1H), 8.04 (s, 1H), 7.72 (dd; 1H; J=7.2, 0.8 Hz), 7.27 (m, 4H), 6.67 (d, 1H, J=8.0 Hz), 6.64 (t, 1H, J=7.5 Hz), 5.66 (d, 2H, J=7.5 Hz), 5.15 (q, 1H, J=7.5 Hz), 2.87 (m, 2H), 2.43 (m, 1H), 1.82 (m, 1H), 1.28 (s, 9H); MS (ESI$^+$) m/z 379 (M+H).

EXAMPLE 17

4-[({[(1R)-5-tert-butyl-2,3-dihydro-1H-inden-1-yl]amino}carbonyl)amino]-1H-indazol-1-yl}methyl acetate The product from Example 16 (50 mg, 0.132 mmol) and acetic anhydride (1 mL) were heated for 4 hours at 60°. The mixture was evaporated in vacuo and chromatographed on silica gel (65:35 hexane:ethyl acetate, eluant) to afford the desired product as a white solid, 12 mg (22%). $^1$H NMR ($d_6$-DMSO) δ 8.67 (s, 1H), 8.16 (s, 1H), 7.75 (d, 1H, J=7.5 Hz), 7.27 (m, 5H), 6.67 (d, 1H, J=7.8 Hz), 6.34 (s, 2H), 5.15 (q, 1H, J=6.7 Hz), 2.85 (m, 2H), 2.42 (m, 1H), 2.02 (s, 3H), 1.85 (m, 1H), 1.28 (s, 9H); MS (ESI$^+$) m/z 421 (M+H), 443 (M+Na).

EXAMPLE 18

{4-[({[(1R)-5-tert-butyl-2,3-dihydro-1H-inden-1-yl]amino}carbonyl)amino]-1H-indazol-1-yl}methyl 3-hydroxypropanoate

EXAMPLE 18A

3-{[tert-butyl(diphenyl)silyl]oxy}propan-1-ol

To a solution of 1,3-propanediol (1.25 g, 16.4 mmol) in N,N-dimethylformamide (50 mL) was added imidazole (2.23 g, 32.8 mmol) and tert-butyldiphenylsilyl chloride (4.97 g, 18.1 mmol). The reaction was stirred for 3 days at room temperature, then was diluted with ethyl acetate and was washed with water and brine. Concentration in vacuo afforded the crude product as a thick colorless oil which was used directly in the next step.

EXAMPLE 18B

3-{[tert-butyl(diphenyl)silyl]oxy}propanoic acid

Example 18A (~5.0 g, 16.4 mmol) was dissolved in acetone (700 mL) and then chilled in ice. Jones reagent (10 mL, prepared by dissolution of 26.72 g $CrO_3$ in 23 mL conc. $H_2SO_4$ and dilution to 100 mL with $H_2O$) was added slowly. The reaction mixture was stirred in the ice bath for 10 minutes, then the acetone was removed in vacuo. Ethyl acetate was added, and this solution was washed several times with $H_2O$ and once with brine. The solution was dried over $Na_2SO_4$ and was then evaporated in vacuo to afford a crude yellow oil, 5.9 g (quantitative). MS (ESI$^+$) m/z 351 (M+Na); MS (ESI$^-$) m/z 327 (M−H).

EXAMPLE 18C chloromethyl 3-{[tert-butyl(diphenyl)silyl]oxy}propanoate

The title compound was prepared from the compound of Example 18B using the procedure as described in Synth. Commun. 2003, 33, 1683. $^1$H NMR ($d_6$-DMSO) δ 7.58-7.64 (m, 4H), 7.37-7.48 (m, 6H), 5.88 (s, 2H), 3.80 (t, 2H, J=6.1 Hz), 2.68 (t, 2H, J=5.8 Hz), 0.96 (s, 9H).

EXAMPLE 18D

{4-[({[(1R)-5-tert-butyl-2,3-dihydro-1H-inden-1-yl]amino}carbonyl)amino]-1H-indazol-1-yl}methyl 3-hydroxypropanoate To a solution of compound from Example 56J (500 mg, 1.44 mmol) in N,N-dimethylformamide (8 mL) was added 60% NaH (65 mg, 1.63 mmol). The reaction was stirred at room temperature for 10 minutes and was then treated with Example 18C (1.35 g, ~40% pure) in 3 mL N,N-dimethylformamide. The mixture was stirred overnight at 60° C. and was then evaporated in vacuo. To this crude mixture in tetrahydrofuran (50 mL) in a polyethylene bottle was added hydrogen fluoride-triethylamine complex (3 mL). The reaction was stirred at room temperature for 5 hours and was then evaporated in vacuo. Chromatography on silica gel (97:3 dichloromethane:methanol to 94:6 dichloromethane:methanol) afforded the desired product as a white solid. $^1$H NMR ($d_6$-DMSO) δ 8.68 (s, 1H), 8.16 (s, 1H), 7.75 (dd; 1H; J=7.5, 1.0 Hz), 7.27-7.37 (m, 5H), 6.68 (d, 1H, J=7.8 Hz), 6.35 (s, 2H), 5.15 (q, 1H, J=6.9 Hz), 4.69 (t, 1H, J=5.0 Hz), 3.60 (m, 2H), 2.73-3.01 (m, 2H), 2.44 (t, 2H, J=6.1 Hz), 1.78-1.92 (m, 2H), 1.28 (s, 9H); MS (ESI$^+$) m/z 451 (M+H).

EXAMPLE 19

(phosphonooxy)methyl 4-[({[(1R)-5-tert-butyl-2,3-dihydro-1H-inden-1-yl]amino}carbonyl)amino]-1H-indazole-1-carboxylate

EXAMPLE 19A

Thiocarbonic acid O-sec-butyl ester O-chloromethyl ester

Sodium methoxide (11.5 g 0.2 moles) of 95% was added to 200 ml of methanol and the solution was cooled to 0° C. Sec-butanethiol (21.4 ml, 0.2 mol) was then added dropwise and the solution stirred for 2 hours. The solvent was removed and the residue was evaporated from ether twice. 300 ml of diethyl ether was added to the residue and the mixture was cooled to −78° C. Chloromethyl chloroformate (19 ml, 0.2 mol) in 75 ml of ether was added dropwise and the reaction mixture was allowed to warm to room temperature and then stirred for 18 hours. The reaction was filtered through celite and washed with ether. The filtrate was evaporated, resuspended in in ether and filtered through a silica plug, and the solvent was evaporated to give 29 g of a clear liquid. $^1$H NMR (300 MHz, CDCl$_3$) δ ppm 0.94 (t, J=7.29 Hz, 3 H) 1.36-1.48 (m, 2 H) 1.60-1.70 (m, 2 H) 2.89-2.95 (m, 2 H) 5.76 (s, 2 H).

EXAMPLE 19B

Thiocarbonic acid O-sec-butyl ester O-iodomethyl ester

Example 19A (6.0 g 33 mmol) in 45 mL of acetone was combined with (9.8 g 66 mmol) of sodium iodide and (0.3 g 3.3 mmol) of sodium bicarbonate and heated at 40° C. for 4 hours. 100 ml of diethyl ether was added and the mixture was washed with 10% sodium bicarbonate then 1% sodium thiosulfate until the organic phase was clear. The organic phase was dried with sodium sulfate and the solvent was evaporated. The residue was resuspended in pentane and the organic layer was washed with 10% sodium bicarbonate then 1% sodium thiosulfate. The organic phase was then dried with magnesium sulfate and the solvent was evaporated to give 7.3 g of a clear oil. $^1$H NMR (300 MHz, CDCl$_3$) δ ppm 0.93 (t, J=7.29 Hz, 3 H) 1.35-1.48 (m, 2 H) 1.58-1.70(m, 2 H) 2.88-2.94 (m, 2 H) 5.99 (s, 2 H).

EXAMPLE 19C

O-({[bis(benzyloxy)phosphoryl]oxy}methyl) O-(sec-butyl) thiocarbonate

The product of Example 19B (7.3 g, 27 mmoles) and tetrabutylammonium dibenzylphosphate (13.8 g, 26.6 mmol) were mixed in 20 ml of tetrahydrofuran and stirred at room temperature for 24 hours. The mixture was diluted with 100 mL of tetrahydrofuran, filtered through celite and the solvent was evaporated. The residue was resuspended in 200 mL of 20% ethyl acetate in hexane and the precipitate was filtered and washed with an additional 100 mL of 20% ethyl acetate. The organic filtrates were combined and the solvent was evaporated. Final product was obtained by flash chromatography on silica using 20% ethyl acetate in hexane. Fractions containing product were combined and the solvent was removed to give 8.7 g (78%) of a colorless oil. $^1$H NMR (300 MHz, CDCl$_3$) δ ppm 0.91 (t, J=7.29 Hz, 3 H) 1.31-1.45 (m, 2 H) 1.55-1.65 (m, 2 H) 2.80-2.90 (m, 2 H) 5.07 (d, J=7.80 Hz, 4 H) 5.65 (d, J=13.90 Hz, 2 H) 7.34 (s, 10 H).

EXAMPLE 19D

O-dibenzylphosphonooxymethyl chloroformate 7.3 g (17 mmol) of the compound from Example 19C was cooled to 4° C. 1.7 mL (21 mmol) of sulfuryl chloride was added dropwise. Reaction was stirred at 4° C. for an additional 20 minutes, the cooling bath was removed and the mixture was allowed to stir at room temperature for an additional 3 hours. Diethyl ether was added and then was evaporated under vacuum. The remaining oil was dried under high vacuum for 18 hours yielding 6.1 g (quantitative) of a colorless oil. $^1$H NMR (300 MHz, CDCl$_3$) δ ppm 5.08 (d, J=8.14 Hz, 4 H) 5.62 (d, J=14.24 Hz, 2 H) 7.35 (s, 10 H).

EXAMPLE 19E

{[bis(benzyloxy)phosphoryl]oxy}methyl 4-[({[(1R)-5-tert-butyl-2,3-dihydro-1H-inden-1-yl]amino}carbonyl)amino]-1H-indazole-1-carboxylate 1.6 g (4.6 mmol) of compound from Example 56J in 15 mL of tetrahydrofuran was cooled to −40° C. in an acetonitrile dry ice bath. 1 mL (9.1 mmol) of 4-methylmorpholine was added, then 4.1 g (11 mmol) of compound from Example 19D was added dropwise. The reaction was stirred at −40° C. for 20 minutes then the ice bath removed and the reaction allowed to warm to room temperature. The mixture was diluted with 200 mL of diethyl ether, extracted 4 times with 25 mL of water, dried over magnesium sulfate, 2 mL of dimethylformamide was added and the ether removed by rotory evaporation leaving a clear oil which was purified by reverse phase HPLC with 0.1% trifluoroacetic acid in water and acetonitrile as mobile phases to provide 1.3 g of a white powder. $^1$H NMR (400 MHz, DMSO-d$_6$) δ ppm 1.31 (s, 9 H) 1.88-1.98 (m, 1 H) 2.48-2.57 (m, 1 H) 2.87 (m, 1 H) 2.97-3.05 (m, 1H) 5.16 (d, J=7.98 Hz, 4 H) 5.26 (q, J=7.06 Hz, 1 H) 6.05 (d, J=14.73 Hz, 2 H) 6.79 (d, J=7.67 Hz, 1 H) 7.29-7.39 (m, 13 H) 7.55 (t, J=8.13 Hz, 1 H) 7.74 (d, J=8.29 Hz, 1 H) 8.01 (d, J=7.98 Hz, 1 H) 8.53 (s, 1 H) 8.97 (s, 1 H). MS(ESI) m/z 683.3 (M+H)$^+$.

EXAMPLE 19F (phosphonooxy)methyl 4-[({[(1R)-5-tert-butyl-2,3-dihydro-1H-inden-1-yl]amino}carbonyl)amino]-1H-indazole-1-carboxylate 1.3 g (1.9 mmol) of Example 19E in 150 mL of tetrahydrofuran was added to 0.7 g of 20% Pd(OH)$_2$ on carbon, wet, under argon. The vessel was charged to 60 psi with hydrogen and reacted for 3.2 hours with shaking. The catalyst was removed by filtration and the solvent removed. The compound was purified by reverse phase HPLC with 0.1% trifluoroacetic acid in water and acetonitrile as mobile phases to obtain 0.3 g of title compound. $^1$H NMR (300 MHz, DMSO-d$_6$) δ ppm 1.28 (s, 9 H) 1.79-1.91 (m, 1 H) 2.41-2.48 (m, 1 H) 2.77-2.88 (m, 1 H) 2.91-3.01 (m, 1 H) 5.16 (q, J=7.35 Hz, 1 H) 5.84 (d, J=14.24 Hz, 2 H) 6.69 (d, J=7.80 Hz, 1H) 7.25-7.33 (m, 3 H) 7.52 (t, J=8.14 Hz, 1 H) 7.72 (d, J=8.48 Hz, 1 H) 7.90 (d, J=7.80 Hz, 1H) 8.44 (s, 1 H) 8.86 (s, 1 H)MS (DCI/NH$_3$) m/z 503.2 (M+H)$^+$.

EXAMPLE 20

3-{4-[({[(1R)-5-tert-butyl-2,3-dihydro-1H-inden-1-yl]amino}carbonyl)amino]-1H-indazol-1-yl}-3-oxo-propyl dihydrogen phosphate

EXAMPLE 20A

3-{[bis(benzyloxy)phosphoryl]oxy}propanoic acid

The water was removed in vacuo from 3-hydroxy-propionic acid and the residue dried twice from toluene. 0.8 g (8.9 mmol), and dissolved in 10 mL of dry tetrahydrofuran. 1 ml (9 mmol) of 4-methyl-morpholine was added, then 10 mL of a 1 M solution of tert-butyldimethylsilyl chloride in tetrahydrofuran was added and the mixture stirred at room temperature for 10 minutes. 5 g (14.5 mmol) of dibenzyl diisopropylphosphoramidite and 1.2 g (17.1 mmol) of tetrazole was premixed in 20 mL of tetrahydrofuran then added to the reaction mixture and allowed to react at room temperature for 30 minutes. The mixture was cooled to 0° C. in an ice bath, then 3.5 mL of 35% aqueous hydrogen peroxide was added and the mixture stirred for 30 minutes. 10 mL of 10% sodium bisulfite was added slowly then 200 mL of diethyl ether. The organic phase was washed three times with 10% potassium dihydrogen phosphate, dried over magnesium sulfate and the was solvent evaporated. Product was obtained by flash chromatography of the crude material on silica using hexanes and ethyl acetate (70:30). $^1$H NMR (300 MHz, CDCl$_3$) δ ppm 2.65 (t, J=6.10

Hz, 2 H) 4.26 (q, J=6.44 Hz, 2 H) 5.04 (d, J=8.14 Hz, 4 H) 7.33 (s, 10 H). MS (ESI) m/z 351.1 (M+H)+.

EXAMPLE 20B dibenzyl 3-{4-[({[(1R)-5-tert-butyl-2,3-dihydro-1H-inden-1-yl]amino}carbonyl)amino]-1H-indazol-1-yl}-3-oxopropyl phosphate 1.1 g (3.1 mmol) of Example 20A in 8 mL of dichloromethane and 3.1 mL of a 1M solution of N,N'-dicyclohexylcarbodiimide in dichloromethane were mixed and 1.0 g (2.9 mmol) of Example 56J in 8 mL of dimethylformamide was added. The mixture was allowed to react at room temperature for 18 hours. 200 mL of diethyl ether was added to the mixture and the organic phase was washed three times with water, dried over magnesium sulfate and the solvent removed. The product was isolated by flash chromatography on silica using hexanes and ethyl acetate (80:20). $^1$H NMR (300 MHz, DMSO-$d_6$) δ ppm 1.28 (s, 9 H) 1.79-1.92 (m, 1 H) 2.41-2.49 (m, 1 H) 2.77-2.89 (m, 1 H) 2.91-3.02 (m, 1 H) 3.56 (t, J=5.93 Hz, 2 H) 4.39-4.49 (m, 2 H) 5.01 (d, J=8.14 Hz, 4 H) 5.17 (q, J=7.23 Hz, 1 H) 6.70 (d, J=7.80 Hz, 1 H) 7.25-7.38 (m, 13 H) 7.52 (t, J=8.14 Hz, 1 H) 7.89 (t, J=8.14 Hz, 2 H) 8.41 (s, 1 H) 8.85 (s, 1H). MS (ESI) m/z 681.5 (M+H)+.

EXAMPLE 20C

3-{4-[({[(1R)-5-tert-butyl-2,3-dihydro-1H-inden-1-yl]amino}carbonyl)amino]-1H-indazol-1-yl}-3-oxopropyl dihydrogen phosphate 0.45 g (0.7 mmol) of Example 20B in 100 mL of tetrahydrofuran was added to 0.7 g of 20% Pd(OH)$_2$ on carbon, wet, under argon. The vessel was charged to 60 psi with hydrogen and reacted for 3.2 hours with shaking. The catalyst was removed by filtration and the solvent was evaporated. The compound was purified by reverse phase HPLC with 0.1% trifluoroacetic acid in water and acetonitrile as mobile phases to obtain 0.15 g of title compound. $^1$H NMR (300 MHz, DMSO-$d_6$) δ ppm 1.28 (s, 9 H) 1.79-1.92 (m, 1 H) 2.41-2.49 (m, 1 H) 2.76-2.88 (m, 1 H) 2.89-3.01 (m, 1 H) 3.53 (t, J=6.27 Hz, 2 H) 4.23-4.32 (m, 2 H) 5.17 (q, J=7.12 Hz, 1 H) 6.71 (d, J=7.80 Hz, 1 H) 7.25-7.33 (m, 3 H) 7.52 (t, J=8.14 Hz, 1 H) 7.89 (t, J=7.46 Hz, 2 H) 8.42 (d, J=0.68 Hz, 1 H) 8.86 (s, 1 H). MS (ESI) m/z 501.3 (M+H)+.

EXAMPLE 21

[({4-[({[(1R)-5-tert-butyl-2,3-dihydro-1H-inden-1-yl]amino}carbonyl)amino]-1H-indazol-1-yl}carbonyl)oxy]methylphosphonic acid

EXAMPLE 21A

Hydroxymethyl-phosphonic acid dibenzyl ester

Charged an Emrys 5 mL process vial with 2.0 g (7.63 mmol) dibenzyl phosphite, 229 mg (7.63 mmol) paraformaldehyde powder, and 0.11 mL (0.76 mmol) triethylamine. The white mixture was heated in a microwave (Personal Chemistry) at 130° for 5 minutes. The crude oil was purified on silica gel, eluting with 50-100% ethyl acetate in hexane to provide 947 mg (42% yield) of the title compound, a colorless oil. MS (ESI) m/z: 181.1, 293.0 [M+H]+ $^1$H NMR (DMSO-$d_6$) δ: 3.83 (m, 2H), 5.02 (d, 4H), 5.50 (m, 1H), 7.37 (m, 10H).

EXAMPLE 21B (4-Nitro-phenoxycarbonyloxymethyl)-phosphonic acid dibenzyl ester Charged a round bottom flask with 20 mL dichloroethane, 947 mg (3.24 mmol) of Example 21A, 718 mg (3.56 mmol) 4-nitrophenyl chloroformate, and 0.31 mL (3.89 mmol) pyridine. The reaction mixture was stirred at 0° C. for 40 minutes, treated with 50 mL ethyl acetate, filtered through a silica gel plug, rinsed with ethyl acetate, and concentrated. The crude oil was purified on silica gel with 30-70% ethyl acetate in hexane to provide 1.429g (97% yield) of the title compound. MS (ESI) m/z: 181.0, 351.1, 458.1 [M+H]+ $^1$H NMR (DMSO-$d_6$) δ: 4.71 (d, 2H), 5.11 (d, 4H), 7.39 (m, 10H), 7.48 (d, 2H), 8.29 (d, 2H).

EXAMPLE 21C

[bis(benzyloxy)phosphoryl]methyl 4-[({[(1R)-5-tert-butyl-2,3-dihydro-1H-inden-1-yl]amino}carbonyl)amino]-1H-indazole-1-carboxylate Dissolved 990 mg (2.84 mmol) of Example 56J in 10 mL N,N-dimethylformamide solution, added 3.12 mL (3.12 mmol) 1.0M potassium tert-butoxide in tetrahydrofuran, stirred for 5 minutes at ambient temperature, then added 1.429 g (3.12 mmol) of Example 21B in 10 mL N,N-dimethylformamide. After 15 minutes, the solution was partitioned between 200 mL ethyl acetate and 200 mL H$_2$O, dried the organic layer with brine and Na$_2$SO$_4$, and concentrated. The crude oil was purified on silica gel, eluting with 50-100% ethyl acetate in hexane to obtain 1.622 g (86%) of title compound as yellow foam. MS (ESI) m/z: 349.1, 667.30 [M+H]+ $^1$H NMR (DMSO-$d_6$) δ: 1.28 (s, 9H), 1.79-1.91 (m, 1H), 2.41-2.47 (m, 1H), 2.79-2.87 (m, 1H), 2.91-3.01 (m, 1H), 4.94 (d, 2H), 5.11-5.23 (m, 5H), 6.70 (d, 1H), 7.27 (s, 2H), 7.29-7.41 (m, 11H), 7.45 (t, 1H), 7.62 (d, 1H), 7.89 (d, 1H), 8.44 (s, 1H), 8.86 (s, 1H).

EXAMPLE 21D

[({4-[({[(1R)-5-tert-butyl-2,3-dihydro-1H-inden-1-yl]amino}carbonyl)amino]-1H-indazol-1-yl}carbonyl)oxy]methylphosphonic acid 1.5 g (2.25 mmol) of the compound from Example 21C was added to a mixture of 0.3 g 20% Pd(OH)$_2$/C and 150 mL methanol in a stainless steel autoclave. The reactor was sealed and flushed with nitrogen, and then it was pressurized with hydrogen (60 psi). The mixture was stirred at ambient temperature for 90 minutes. Product precipitated, added 150 mL tetrahydrofuran to redissolve, catalyst was filtered off, washed with methanol and tetrahydrofuran, and the filtrate was concentrated to provide 1.08 g (99%) of the title compound. MS (ESI) m/z: 485.21 [M−H]− $^1$H NMR (DMSO-$d_6$) δ: 1.28 (s, 9H), 1.81-1.88 (m, 1H), 2.42-2.48 (m, 1H), 2.79-2.87 (m, 1H), 2.91-3.01 (m, 1H), 4.56 (d, 2H), 5.16 (q, 1H), 6.69 (d, 1H), 7.27 (s, 2H), 7.31 (s, 1H), 7.50 (t, 1H), 7.72 (d, 1H), 7.89 (d, 1H), 8.43 (s, 1H), 8.85 (s, 1H).

EXAMPLE 22

[({4-[({[(1R)-5-tert-butyl-2,3-dihydro-1H-inden-1-yl]amino}carbonyl)amino]-1H-indazol-1-yl}carbonyl)oxy]methylphosphonic acid triethylamine salt Suspended 50.2 mg (103 µmol) of compound from Example 21D in 10 mL methanol, added 10.4 mg (103 µmol)

triethylamine, stirred the colorless solution for 10 minutes at ambient temperature, concentrated and vacuum dried. Obtained 61 mg (100% yield) of the title compound as an off-white powder. $^1$H NMR (methanol-$d_4$) δ: 1.29 (t, 9H), 1.32 (s, 9H), 1.90 (m, 1H), 2.59 (m, 1H), 2.89 (m, 1H), 3.00 (m, 1H), 3.16 (q, 6H), 4.54 (d, 2H), 5.29 (t, 1H), 7.28 (s, 2H), 7.31 (s, 1H), 7.52 (t, 1H), 7.74 (d, 1H), 7.97 (d, 1H), 8.36 (s, 1H). Anal Calcd for $C_{23}H_{27}N_4O_6P$.1.0 triethylamine.0.7 methanol: C, 58.47; H, 7.40; N, 11.48. Found: C, 58.46; H, 7.38; N, 11.44.

EXAMPLE 23

2-methoxyethyl 4-[({[(1R)-5-tert-butyl-2,3-dihydro-1H-inden-1-yl]amino}carbonyl)amino]-1H-indazole-1-carboxylate The title compound was prepared using the procedure as described in Example 21C, substituting methoxyethoxychloroformate for Example 21B. MS (ESI) m/z: 450.78 [M+H]$^+$ $^1$H NMR (DMSO-$d_6$) δ: 1.28 (s, 9H), 1.86 (m, 1H), 2.48 (m, 1H), 2.85 (m, 1H), 2.96 (m, 1H), 3.33 (s, 3H), 3.72 (m, 2H), 4.57 (m, 2H), 5.15 (q, 1H), 6.67 (d, 1H), 7.27 (s, 2H), 7.31 (s, 1H), 7.50 (t, 1H), 7.67 (d, 1H), 7.88 (d, 1H), 8.40 (s, 1H), 8.84 (s, 1H). Anal Calcd for $C_{25}H_{30}N_4O_4$: C, 66.65; H, 6.71; N, 12.44. Found: C, 66.22; H, 6.75; N, 12.25.

EXAMPLE 24

(2,2-dimethyl-1,3-dioxolan-4-yl)methyl 4-[({[(1R)-5-tert-butyl-2,3-dihydro-1H-inden-1-yl]amino}carbonyl)amino]-1H-indazole-1-carboxylate

EXAMPLE 24A

Carbonic acid 2,2-dimethyl[1,3]dioxolane-4-ylmethyl ester 2,5-dioxo-pyrrolidin-1-yl ester To a solution of (2,2-dimethyl-[1,3]dioxolan-4-yl)-methanol (0.4 g, 3.0 mmol) in acetonitrile (10 mL) was added carbonic acid bis-(2,5-dioxo-pyrrolidin-1-yl) ester (1.15 g, 4.5 mmol) and triethylamine (0.84 mL, 6.0 mmol). After stirring at ambient temperature for 10 min, the mixture was concentrated at reduced pressure, sat. NaHCO$_3$ (50 mL)was added, and the solution was extracted with ethyl acetate and organic phase was separated and concentrated to obtain 1.0 g of crude product that was used without further purification in the next step. MS (APCI) m/z: 273 [M+H]$^+$ $^1$H NMR (DMSO-$d_6$) δ: 4.50 (m, 1H), 4.40-4.29 (m, 2H), 4.04 (m, 1H), 3.73 (dd, J=6.0 and 9.0 Hz, 1H), 2.80 (s, 4H), 1.35 (s, 3H), 1.30 (s, 3H).

EXAMPLE 24B (2,2-dimethyl-1,3-dioxolan-4-yl)methyl 4-[({[(1R)-5-tert-butyl-2,3-dihydro-1H-inden-1-yl]amino}carbonyl)amino]-1H-indazole-1-carboxylate The title compound was prepared using the procedure as described in Example 21C, substituting Example 24A for Example 21B. MS (APCI) m/z: 507.14 [M+H]$^+$ $^1$H NMR (DMSO-$d_6$) δ: 1.28 (s, 9H), 1.30 (s, 3H), 1.35 (s, 3H), 1.86 (m, 1H), 2.48 (m, 1H), 2.85 (m, 1H), 2.96 (m, 1H), 3.84 (dd, 1H), 4.10 (dd, 1H), 4.45 (m, 3H), 5.15 (q, 1H), 6.67 (d, 1H), 7.27 (s, 2H), 7.31 (s, 1H), 7.50 (t, 1H), 7.69 (d, 1H), 7.88 (d, 1H), 8.40 (s, 1H), 8.83 (s, 1H). Anal Calcd for $C_{28}H_{34}N_4O_5$.1.4H$_2$O: C, 63.24; H, 6.97;N, 10.53. Found: C, 63.16; H, 6.60; N, 10.90.

EXAMPLE 25

(2-oxo-1,3-dioxolan-4-yl)methyl 4-[({[(1R)-5-tert-butyl-2,3-dihydro-1H-inden-1-yl]amino}carbonyl)amino]-1H-indazole-1-carboxylate

EXAMPLE 25A

Carbonic acid 2,5-dioxo-pyrrolidin-1-yl ester 2-oxo-[1,3]dioxolan-4-ylmethyl ester The title compound was prepared using the procedure as described in Example 24A, substituting 4-hydroxymethyl-[1,3]dioxolan-2-one for (2,2-dimethyl-[1,3]dioxolan-4-yl)-methanol. MS (APCI) m/z: 259 [M+H]$^+$ $^1$H NMR (DMSO-$d_6$) δ: 5.13 (m, 1H), 4.61 (m, 3H), 4.31 (dd, J=6.0 and 9.0 Hz, 1H), 2.80 (s, 4H).

EXAMPLE 25B (2-oxo-1,3-dioxolan-4-yl)methyl 4-[({[(1R)-5-tert-butyl-2,3-dihydro-1H-inden-1-yl]amino}carbonyl)amino]-1H-indazole-1-carboxylate The title compound was prepared using the procedure as described in Example 21C, substituting Example 25A for Example 21B. MS (ESI) m/z: 492.93 [M+H]$^+$ $^1$H NMR (DMSO-$d_6$) δ: 1.28 (s, 9H), 1.86 (m, 1H), 2.48 (m, 1H), 2.85 (m, 1H), 2.96 (m, 1H), 4.44 (dd, 1H), 4.66 (m, 3H), 5.15 (q, 1H), 5.24 (m, 1H), 6.68 (d, 1H), 7.27 (s, 2H), 7.31 (s, 1H), 7.51 (t, 1H), 7.64 (d, 1H), 7.89 (d, 1H), 8.42 (s, 1H), 8.85 (s, 1H). Anal Calcd for $C_{26}H_{28}N_4O_6$.0.8H$_2$O: C, 61.60; H, 5.89; N, 11.05. Found: C, 61.62; H, 5.66; N, 11.07.

EXAMPLE 26

2-hydroxyethyl 4-[({[(1R)-5-tert-butyl-2,3-dihydro-1H-inden-1-yl]amino}carbonyl)amino]-1H-indazole-1-carboxylate

EXAMPLE 26A 2-(benzyloxy)ethyl 4-[({[(1R)-5-tert-butyl-2,3-dihydro-1H-inden-1-yl]amino}carbonyl)amino]-1H-indazole-1-carboxylate The title compound was prepared using the procedure as described in Example 21C, substituting benzyloxyethoxychloroformate for Example 21B MS (ESI) m/z: 525 [M−H]$^+$ $^1$H NMR (DMSO-$d_6$) δ: 1.28 (s, 9H), 1.86 (m, 1H), 2.44 (m, 1H), 2.82 (m, 1H), 2.95 (m, 1H), 3.82 (m, 2H), 4.61 (m, 2H), 4.96 (s, 1H), 5.15 (m, 1H), 6.67 (d, J=4.5 Hz, 1H), 7.38-7.25 (m, 9H), 7.48 (t, J=4.5 Hz, 1H), 7.70 (d, J=6.0 Hz, 1H), 7.90 (d, J=6.0 Hz, 1H), 8.40 (s, 1H), 8.84 (s, 1H).

EXAMPLE 26B 2-hydroxyethyl 4-[({[(1R)-5-tert-butyl-2,3-dihydro-1H-inden-1-yl]amino}carbonyl)amino]-1H-indazole-1-carboxylate Example 26A (0.41 g, 0.77 mmol) and 20% Pd(OH)$_2$/C (0.42 g, 0.6 mmol) in ethyl acetate (10 mL) was hydrogenated at ambient temperature at 50 psi for 2 hours. The resulting mixture was filtered through a nylon filter and concentrated to obtain the title compound (0.29 g, 86%). MS (ESI) m/z: 437.0 [M+H]+ $^1$H NMR (DMSO-d$_6$) δ: 1.28 (s, 9H), 1.86 (m, 1H), 2.48 (m, 1H), 2.85 (m, 1H), 2.95 (m, 1H), 3.82 (q, 2H), 4.46 (dd, 2H), 5.00 (t, 1H), 5.15 (q, 1H), 6.67 (d, 1H), 7.27 (s, 2H), 7.31 (s, 1H), 7.49 (t, 1H), 7.69 (d, 1H), 7.87 (d, 1H), 8.40 (s, 1H), 8.84 (s, 1H). Anal Calcd for $C_{24}H_{28}N_4O_4$: C, 66.04; H, 6.47; N, 12.84. Found: C, 65.63; H, 6.54; N, 11.94.

EXAMPLE 27

2-(benzyloxy)-2-oxoethyl 4-[({[(1R)-5-tert-butyl-2, 3-dihydro-1H-inden-1-yl]amino}carbonyl)amino]-1H-indazole-1-carboxylate

EXAMPLE 27A (2,5-Dioxo-pyrrolidin-1-yloxycarbonyloxy)-acetic acid benzyl ester The title compound was prepared using the procedure as described in Example 24A, substituting hydroxy-acetic acid benzyl ester for (2,2-dimethyl-[1,3]dioxolan-4-yl)-methanol.

EXAMPLE 27B 2-(benzyloxy)-2-oxoethyl 4-[({[(1R)-5-tert-butyl-2, 3-dihydro-1H-inden-1-yl]amino}carbonyl)amino]-1H-indazole-1-carboxylate The title compound was prepared using the procedure as described in Example 21C, substituting the compound from Example 27A for the compound from Example 21B MS (ESI) m/z: 541.29 [M+H]+ $^1$H NMR (DMSO-d$_6$) δ: 1.28 (s, 9H), 1.86 (m, 1H), 2.47 (m, 1H), 2.85 (m, 1H), 2.96 (m, 1H), 5.17 (m, 3H), 5.25 (s, 2H), 6.69 (d, 1H), 7.27 (s, 2H), 7.31 (s, 1H), 7.38 (m, 5H), 7.51 (t, 1H), 7.68 (d, 1H), 7.88 (d, 1H), 8.45 (s, 1H), 8.87 (s, 1H). Anal Calcd for $C_{31}H_{32}N_4O_5$: C, 68.87; H, 5.97; N, 10.36. Found: C, 66.93; H, 5.05; N, 9.98.

EXAMPLE 28

2-{[(benzyloxy)carbonyl]amino}ethyl 4-[({[(1R)-5-tert-butyl-2,3-dihydro-1H-inden-1-yl] amino}carbonyl)amino]-1H-indazole-1-carboxylate

EXAMPLE 28A

Carbonic acid 2-benzyloxycarbonylamino-ethyl ester 2,5-dioxo-pyrrolidin-1-yl ester The title compound was prepared using the procedure as described in Example 24A, substituting (2-hydroxy-ethyl)-carbamic acid benzyl ester for (2,2-dimethyl-[1,3]dioxolan-4-yl)-methanol. MS (APCI) m/z: 337 [M+H]+

EXAMPLE 28B

2-{[(benzyloxy)carbonyl]amino}ethyl 4-[({[(1R)-5-tert-butyl-2,3-dihydro-1H-inden-1-yl] amino}carbonyl)amino]-1H-indazole-1-carboxylate The title compound was prepared using the procedure as described in Example 21C, substituting compound from Example 28A for the compound from Example 21B. MS (ESI) m/z: 570.33 [M+H]+ $^1$H NMR (DMSO-d$_6$) δ: 1.28 (s, 9H), 1.85 (m, 1H), 2.48 (m, 1H), 2.85 (m, 1H), 2.95 (m, 1H), 3.45 (q, 2H), 4.47 (t, 2H), 5.01 (s, 2H), 5.15 (q, 1H), 6.67 (d, 1H), 7.27 (s, 2H), 7.32 (m, 6H), 7.47 (t, 1H), 7.55 (m, 1H), 7.65 (d, 1H), 7.87 (d, 1H), 8.39 (s, 1H), 8.83 (s, 1H). Anal Calcd for $C_{32}H_{35}N_5O_5 \cdot 0.9H_2O$: C, 65.60; H, 6.33; N, 11.95. Found: C, 65.60; H, 5.97; N, 11.81.

EXAMPLE 29

[({4-[({[(1R)-5-tert-butyl-2,3-dihydro-1H-inden-1-yl]amino}carbonyl)amino]-1H-indazol-1-yl}carbonyl)oxy]acetic acid The title compound was prepared using the procedure as described in Example 26B, substituting Example 27B for Example 26A. MS (ESI) m/z: 451.20 [M+H]+ $^1$H NMR (DMSO-d$_6$) δ: 1.28 (s, 9H), 1.86 (m, 1H), 2.45 (m, 1H), 2.85 (m, 1H), 2.94 (m, 1H), 4.98 (s, 2H), 5.18 (q, 1H), 6.68 (d, 1H), 7.27 (s, 2H), 7.31 (s, 1H), 7.52 (t, 1H), 7.69 (d, 11), 7.88 (d, 1H), 8.43 (s, 1H), 8.86 (s, 1H), 13.38 (br s, 1H). Anal Calcd for $C_{24}H_{26}N_4O_5 \cdot 0.8H_2O$: C, 62.00; H, 5.98; N, 12.05. Found: C, 62.13; H, 5.78; N, 11.79.

EXAMPLE 30

2-aminoethyl 4-[({[(1R)-5-tert-butyl-2,3-dihydro-1H-inden-1-yl]amino}carbonyl)amino]-1H-indazole-1-carboxylate hydrochloride A mixture of the product from Example 28B (0.53 g, 0.93 mmol) and 10% Pd/C (0.053 g, 0.047 mmol) in methanol (50 mL) and conc. HCl (86 μL, 1.02 mmol) was hydrogenated under 60 psi of hydrogen gas at ambient temperature for 1 h. The resulting mixture was filtered and concentrated to obtain title compound (0.47 g, quantitative yield). $^1$H NMR (DMSO-d$_6$) δ: 1.28 (s, 9H), 1.84 (m, 1H), 2.46 (m, 1H), 2.85 (m, 1H), 2.94 (m, 1H), 4.65 (dd, 2H), 5.18 (q, 1H), 6.96 (d, 1H), 7.26 (s, 2H), 7.31 (s, 1H), 7.51 (t, 1H), 7.69 (d, 1H), 7.91 (d, 1H), 8.02 (br s, 2H), 8.59 (s, 1H), 9.19 (s, 1H). $^1$H NMR (methanol-d$_4$) δ: 1.32 (s, 9H), 1.91 (m, 1H), 2.59 (m, 1H), 2.90 (m, 1H), 3.00 (m, 1H), 3.45 (dd, 2H), 4.71 (dd, 21H), 5.30 (t, 1H), 7.28 (s, 2H), 7.32 (s, 1H), 7.57 (t, 1H), 7.67 (d, 1H), 7.90 (d, 1H), 8.48 (s, 1H). MS (ESI) m/z: 436.2 [M+H]+ Anal Calcd for $C_{24}H_{29}N_5O_3 \cdot HCl \cdot 1.8H_2O$: C, 57.15; H, 6.71; N, 13.88. Found: C, 57.21; H, 6.55; N, 13.60.

EXAMPLE 31

2-ethoxy-2-oxoethyl 4-[({[(1R)-5-tert-butyl-2,3-dihydro-1H-inden-1-yl]amino}carbonyl)amino]-1H-indazole-1-carboxylate

EXAMPLE 31A (4-Nitro-phenoxycarbonyloxy)-acetic acid ethyl ester

The title compound was prepared using the procedure as described in Example 21B, substituting hydroxy-acetic acid ethyl ester for Example 21A. $^1$H NMR (DMSO-d$_6$) δ: 8.36 (m, 2H), 7.57 (m, 2H), 4.90 (s, 2H), 4.20 (q, J=7.5 Hz, 2H), 1.22 (t, J=7.5 Hz, 3H).

EXAMPLE 31B 2-ethoxy-2-oxoethyl 4-[({[(1R)-5-tert-butyl-2,3-dihydro-1H-inden-1-yl]amino}carbonyl)amino]-1H-indazole-1-carboxylate The title compound was prepared using the procedure as described in Example 21C, substituting compound from Example 31A for the compound from Example 21B. MS (ESI) m/z: 479.27 [M+H]+ $^1$H NMR (DMSO-d$_6$) δ: 1.24 (t, 3H), 1.28 (s, 9H), 1.86 (m, 1H), 2.48 (m, 1H), 2.85 (m, 1H), 2.94 (m, 1H), 4.20 (q, 2H), 5.09 (s, 2H), 5.18 (q, 1H), 6.69 (d, 1H), 7.28 (s, 2H), 7.31 (s, 1H), 7.52 (t, 1H), 7.69 (d, 1H), 7.88 (d, 1H), 8.45 (s, 1H), 8.88 (s, 1H). Anal Calcd for C$_{26}$H$_{30}$N$_4$O$_5$.0.4 H$_2$O: C, 64.29; H, 6.39; N, 11.53. Found: C, 64.22; H, 6.23; N, 11.46.

EXAMPLE 32

(diethoxyphosphoryl)methyl 4-[({[(1R)-5-tert-butyl-2,3-dihydro-1H-inden-1-yl]amino}carbonyl)amino]-1H-indazole-1-carboxylate

EXAMPLE 32A (4-Nitro-phenoxycarbonyloxymethyl)-phosphonic acid diethyl ester The title compound was prepared using the procedure as described in Example 21B, substituting hydroxymethylphosphonic acid diethyl ester for Example 21A. $^1$H NMR (DMSO-d$_6$) δ: 8.38 (d, J=11.0 Hz, 2H), 7.60 (d, J-11.0 Hz, 2H), 4.63 (d, 7.5 Hz, 2H), 4.10 (m, 4H), 1.24 (t, J=6.0 Hz, 6H).

EXAMPLE 32B (diethoxyphosphoryl)methyl 4-[({[(1R)-5-tert-butyl-2,3-dihydro-1H-inden-1-yl]amino}carbonyl)amino]-1H-indazole-1-carboxylate The title compound was prepared using the procedure as described in Example 21C, substituting Example 32A for Example 21B. MS (ESI) m/z: 543.3 [M+H]+. $^1$H NMR (DMSO-d$_6$) δ: 1.26 (s, 6H), 1.28 (s, 9H), 1.86 (m, 1H), 2.47 (m, 1H), 2.85 (m, 1H), 2.96 (m, 1H), 4.15 (m, 4H), 4.84 (d, 2H), 5.15 (q, 1H), 6.70 (d, 1H), 7.27 (s, 2H), 7.31 (s, 1H), 7.52 (t, 1H), 7.67 (d, 1H), 7.88 (d, 1H), 8.44 (s, 1H), 8.87 (s, 1H). Anal Calcd for C$_{27}$H$_{35}$N$_4$O$_6$P.0.4 H$_2$O: C, 58.99; H, 6.56; N, 10.19. Found: C, 59.08; H, 6.40; N, 10.01.

EXAMPLE 33

2-(diethylamino)-2-oxoethyl 4-[({[(1R)-5-tert-butyl-2,3-dihydro-1H-inden-1-yl]amino}carbonyl)amino]-1H-indazole-1-carboxylate

EXAMPLE 33A

Carbonic acid diethylcarbamoylmethyl ester 4-nitro-phenyl ester

The title compound was prepared using the procedure as described in Example 21B, substituting N,N-diethyl-2-hydroxy-acetamide for Example 21A. $^1$H NMR (DMSO-d$_6$) δ: 8.38 (d, J=11.0 Hz, 2H), 7.57 (d, J-11.0 Hz, 2H), 5.0 (s, 2H), 3.20 (m, 4H), 1.12 (m 6H).

EXAMPLE 33B 2-(diethylamino)-2-oxoethyl 4-[({[(1R)-5-tert-butyl-2,3-dihydro-1H-inden-1-yl]amino}carbonyl)amino]-1H-indazole-1-carboxylate The title compound was prepared using the procedure as described in Example 21C, substituting Example 33A for Example 21B. MS (ESI) m/z: 506.32 [M+H]+ $^1$H NMR (DMSO-d$_6$) δ: 1.05 (t, 3H), 1.18 (t, 3H), 1.28 (s, 9H), 1.86 (m, 1H), 2.48 (m, 1H), 2.85 (m, 1H), 2.96 (m, 1H), 5.18 (m, 3H), 6.68 (d, 1H), 7.28 (s, 2H), 7.31 (s, 1H), 7.50 (t, 1H), 7.70 (d, 1H), 7.87 (d, 1H), 8.42 (s, 1H), 8.86 (s, 1H). Anal Calcd for C$_{28}$H$_{35}$N$_5$O$_4$.0.7 H$_2$O: C, 64.90; H, 7.08; N, 13.51. Found: C, 65.04; H, 7.13; N, 13.41.

EXAMPLE 34

2-oxopropyl 4-[({[(1R)-5-tert-butyl-2,3-dihydro-1H-inden-1-yl]amino}carbonyl)amino]-1H-indazole-1-carboxylate

EXAMPLE 34A

Carbonic acid 4-nitro-phenyl ester 2-oxo-propyl ester

The title compound was prepared using the procedure as described in Example 21B, substituting 1-hydroxy-propan-2-one for Example 21A. $^1$H NMR (DMSO-d$_6$) δ: 8.35 (d, J=11.0 Hz, 2H), 7.58 (d, J-11.0 Hz, 2H), 5.00 (m 2H), 2.16 (s, 3H).

EXAMPLE 34B 2-oxopropyl 4-[({[(1R)-5-tert-butyl-2,3-dihydro-1H-inden-1-yl]amino}carbonyl)amino]-1H-indazole-1-carboxylate The title compound was prepared using the procedure as described in Example 21C, substituting Example 34A for Example 2 1B. MS (ESI) m/z: 449.17 [M+H]+ $^1$H NMR (DMSO-d$_6$) δ: 1.28 (s, 9H), 1.86 (m, 1H), 2.23 (s, 3H), 2.47 (m, 1H), 2.85 (m, 1H), 2.96 (m, 1H), 4.84 (d, 1H), 5.17 (q, 1H), 5.40 (d, 1H), 6.69 (d, 1H), 7.23 (d, 1H), 7.27 (s, 2H), 7.31 (s, 1H), 7.39 (t, 1H), 7.82 (d, 1H), 8.23 (s, 1H), 8.71 (s, 1H). Anal Calcd for C$_{25}$H$_{28}$N$_4$O$_4$.0.3 H$_2$O: C, 66.15; H, 6.35; N, 12.34. Found: C, 66.14; H, 6.25; N, 12.46.

EXAMPLE 35

2-(acetyloxy)ethyl 4-[({[(1R)-5-tert-butyl-2,3-dihydro-1H-inden-1-yl]amino}carbonyl)amino]-1H-indazole-1-carboxylate

EXAMPLE 35A

Acetic acid 2-(4-nitro-phenoxycarbonyloxy)-ethyl ester

The title compound was prepared using the procedure as described in Example 21B, substituting acetic acid 2-hydroxy-ethyl ester for Example 21A. $^1$H NMR (DMSO-d$_6$) δ: 8.38 (d, J=11.0 Hz, 2H), 7.59 (d, J-11.0 Hz, 2H), 4.46 (m 2H), 4.12 (m, 2H), 2.05 (s, 3H).

EXAMPLE 35B 2-(acetyloxy)ethyl 4-[({[(1R)-5-tert-butyl-2,3-dihydro-1H-inden-1-yl]amino}carbonyl)amino]-1H-indazole-1-carboxylate The title compound was prepared using the procedure as described in Example 21C, substituting Example 35A for Example 21B. MS (ESI) m/z: 479.27 [M+H]+ $^1$H NMR (DMSO-d$_6$) δ: 1.28 (s, 9H), 1.86 (m, 1H), 2.05 (s, 3H), 2.48 (m, 1H), 2.85 (m, 1H), 2.96 (m, 1H), 4.41 (m, 2H), 4.65 (m, 2H), 5.15 (q, 1H), 6.69 (d, 1H), 7.27 (s, 2H), 7.31 (s, 1H), 7.51 (t, 1H), 7.66 (d, 1H), 7.88 (d, 1H), 8.41 (s, 1H), 8.86 (s, 1H). Anal Calcd for C$_{26}$H$_{30}$N$_4$O$_5$.0.4 H$_2$O: C, 64.29; H, 6.39; N, 11.53. Found: C, 64.29; H, 6.48; N, 11.24.

EXAMPLE 36

2-(dimethoxyphosphoryl)ethyl 4-[({[(1R)-5-tert-butyl-2,3-dihydro-1H-inden-1-yl]amino}carbonyl)amino]-1H-indazole-1-carboxylate

EXAMPLE 36A

[2-(4-Nitro-phenoxycarbonyloxy)-ethyl]-phosphonic acid dimethyl ester

The title compound was prepared using the procedure as described in Example 21B, substituting (2-hydroxy-ethyl)-phosphonic acid dimethyl ester for Example 21A. MS (ESI) m/z: 320 [M+H]$^+$ $^1$H NMR (DMSO-d$_6$) δ: 8.35 (d, J=11.0 Hz, 2H), 7.56 (d, J=11.0 Hz, 2H), 4.40 (m, 2H), 3.70 (s, 3H), 3.66 (s, 3H), 2.37 (m, 2H).

EXAMPLE 36B 2-(dimethoxyphosphoryl)ethyl 4-[({[(1R)-5-tert-butyl-2,3-dihydro-1H-inden-1-yl]amino}carbonyl)amino]-1H-indazole-1-carboxylate The title compound was prepared using the procedure as described in Example 21C, substituting Example 36A for Example 21B. MS (ESI) m/z: 529.25 [M+H]$^+$ $^1$H NMR (DMSO-d$_6$) δ: 1.28 (s, 9H), 1.85 (m, 1H), 2.42 (m, 3H), 2.85 (m, 1H), 2.94 (m, 1H), 3.64 (s, 3H), 3.68 (s, 3H), 4.60 (m, 2H), 5.15 (q, 1H), 6.68 (d, 1H), 7.27 (s, 2H), 7.31 (s, 1H), 7.50 (t, 1H), 7.71 (d, 1H), 7.87 (d, 1H), 8.40 (s, 1H), 8.84 (s, 1H). Anal Calcd for C$_{26}$H$_{33}$N$_4$O$_6$P.0.5 H$_2$O: C, 58.09; H, 6.38; N, 10.42. Found: C, 58.16; H1 6.37; N, 10.30.

EXAMPLE 37

[bis(benzyloxy)phosphoryl]methyl 4-[({[(1R)-5-tert-butyl-2,3-dihydro-1H-inden-1-yl]amino}carbonyl)amino]-1H-indazole-1-carboxylate

EXAMPLE 37A (4-Nitro-phenoxycarbonyloxymethyl)-phosphonic acid dibenzyl ester The title compound was prepared using the procedure as described in Example 21B, substituting hydroxymethyl-phosphonic acid dibenzyl ester for Example 21A. MS (ESI) m/z: 458 [M+H]$^+$ $^1$H NMR (DMSO-d$_6$) δ: 8.30 (d, J=11.0 Hz, 2H), 7.51 (d, J=11.0 Hz, 2H), 7.37 (m, 10H), 5.13 (d, J=7.5 Hz, 4H), 4. 72 (d J=8.0 Hz, 2H).

EXAMPLE 37B

[bis(benzyloxy)phosphoryl]methyl 4-[({[(1R)-5-tert-butyl-2,3-dihydro-1H-inden-1-yl]amino}carbonyl)amino]-1H-indazole-1-carboxylate The title compound was prepared using the procedure as described in Example 21C, substituting Example 37A for the compound from Example 21B. MS (ESI) m/z: 349.1, 667.30 [M+H]$^+$ $^1$H NMR (DMSO-d$_6$) δ: 1.28 (s, 9H), 1.79-1.91 (m, 1H), 2.41-2.47 (m, 1H), 2.79-2.87 (m, 1H), 2.91-3.01 (m, 1H), 4.94 (d, 2H), 5.11-5.23 (m, 5H), 6.70 (d, 1H), 7.27 (s, 2H), 7.29-7.41 (m, 11H), 7.45 (t, 1H), 7.62 (d, 1H), 7.89 (d, 1H), 8.44 (s, 1H), 8.86 (s, 1H). Anal Calcd for C$_{37}$H$_{39}$N$_4$O$_6$P: C, 66.66; H, 5.90; N, 8.40. Found: C, 66.56; H, 5.76; N, 8.55.

EXAMPLE 38

[({4-[({[(1R)-5-tert-butyl-2,3-dihydro-1H-inden-1-yl]amino}carbonyl)amino]-1H-indazol-1-yl}carbonyl)oxy]methylphosphonic acid The title compound was prepared using the procedure as described in Example 26B, substituting Example 37B for Example 26A. MS (ESI) m/z: 485.21 [M–H]$^-$ $^1$H NMR (DMSO-d$_6$) δ: 1.28 (s, 9H), 1.81-1.88 (m, 1H), 2.42-2.48 (m, 1H), 2.79-2.87 (m, 1H), 2.91-3.01 (m, 1H), 4.56 (d, 2H), 5.16 (q, 1H), 6.69 (d, 1H), 7.27 (s, 2H), 7.31 (s, 1H), 7.50 (t, 1H), 7.72 (d, 1H), 7.89 (d, 1H), 8.43 (s, 1H), 8.85 (s, 1H). $^1$H NMR (methanol-d$_4$) δ: 1.32 (s, 9H), 1.89 (m, 1H), 2.59 (m, 1H), 2.87 (m, 1H), 3.01 (m, 1H), 4.72 (d, 2H), 5.29 (t, 1H), 7.28 (s, 2H), 7.32 (s, 1H), 7.54 (t, 1H), 7.75 (d, 1H), 7.90 (d, 1H), 8.41 (s, 1H). Anal Calcd for C$_{23}$H$_{27}$N$_4$O$_6$P.0.6 H$_2$O: C, 55.55; H, 5.72; N, 11.27. Found: C, 55.63; H, 5.77; N, 10.99.

EXAMPLE 39

[({4-[({[(1R)-5-tert-butyl-2,3-dihydro-1H-inden-1-yl]amino}carbonyl)amino]-1H-indazol-1-yl}carbonyl)oxy]methylphosphonate, triethylamine salt To a suspension of Example 38 (0.05 g, 0.1 mmol) in methanol (10 mL) was added triethylamine (0.01 g, 0.1 mmol) and the mixture stirred 10 minutes at ambient temperature, concentrated under reduced pressure and drying in vacuum to provide 0.06 g (100%) of title compound. $^1$H NMR (methanol-d$_4$) δ: 1.29 (t, 9H), 1.32 (s, 9H), 1.90 (m, 1H), 2.59 (m, 1H), 2.89 (m, 1H), 3.00 (m, 1H), 3.16 (q, 6H), 4.54 (d, 2H), 5.29 (t, 1H), 7.28 (s, 2H), 7.31 (s, 1H), 7.52 (t, 1H), 7.74 (d, 1H), 7.97 (d, 1H), 8.36 (s, 1H). Anal Calcd for C$_{23}$H$_{27}$N$_4$O$_6$P.1.0 triethylamine.0.7 methanol: C, 58.47; H, 7.40; N, 11.48. Found: C, 58.46; H, 7.38; N, 11.44.

EXAMPLE 40

[({4-[({[(1R)-5-tert-butyl-2,3-dihydro-1H-inden-1-yl]amino}carbonyl)amino]-1H-indazol-1-yl}carbonyl)oxy]methylphosphonic acid, diethylaminoethanol salt The title compound was prepared using the procedure as described in Example 39, substituting diethylaminoethanol for triethylamine. $^1$H NMR (methanol-d$_4$) δ: 1.30 (t, 6H), 1.32 (s, 9H), 1.90 (m, 1H), 2.59 (m, 1H), 2.89 (m, 1H), 3.00 (m, 1H), 3.20 (m, 6H), 3.83 (dd, 2H), 4.54 (d, 2H), 5.29 (t, 1H), 7.28 (s, 2H), 7.31 (s, 1H), 7.52 (t, 1H), 7.74 (d, 1H), 7.98 (d, 1H), 8.36 (s, 1H). Anal Calcd for C$_{23}$H$_{27}$N$_4$O$_6$P.0.8

C₆H15NO.0.65 methanol: C, 56.85; H, 6.98; N, 11.19. Found: C, 56.85; H, 7.01; N, 11.23.

EXAMPLE 41

[({4-[({[(1R)-5-tert-butyl-2,3-dihydro-1H-inden-1-yl]amino}carbonyl)amino]-1H-indazol-1-yl}carbonyl)oxy]methylphosphonic acid, triethanolamine salt The title compound was prepared using the procedure as described in Example 39, substituting triethanolamine for triethylamine. $^1$H NMR (methanol-d₄) δ: 1.31 (s, 9H), 1.90 (m, 1H), 2.59 (m, 1H), 2.89 (m, 1H), 3.00 (m, 1H), 3.37 (m, 6H), 3.87 (dd, 6H), 4.54 (d, 2H), 5.29 (t, 1H), 7.28 (s, 2H), 7.31 (s, 1H), 7.52 (t, 1H), 7.74 (d, 1H), 7.98 (d, 1H), 8.36 (s, 1H). Anal Calcd for C₂₃H₂₇N₄O₆P1.1 C₆H₁₅NO₃.0.7 methanol: C, 54.08; H, 6.93; N, 10.61. Found: C, 54.08; H, 6.82; N, 10.67.

EXAMPLE 42

[({4-[({[(1R)-5-tert-butyl-2,3-dihydro-1H-inden-1-yl]amino}carbonyl)amino]-1H-indazol-1-yl}carbonyl)oxy]methylphosphonic acid, piperazine salt The title compound was prepared using the procedure as described in Example 39, substituting piperazine for triethylamine. $^1$H NMR (methanol-d₄) δ: 1.32 (s, 9H), 1.90 (m, 1H), 2.59 (m, 1H), 2.89 (m, 1H), 3.01 (m, 1H), 3.04 (s, 8H), 4.54 (d, 2H), 5.29 (t, 1H), 7.29 (s, 2H), 7.31 (s, 1H), 7.52 (t, 1H), 7.74 (d, 1H), 7.97 (d, 1H), 8.37 (s, 1H). Anal Calcd for C₂₃H₂₇N₄O₆P.0.9 C₄H₁₀N₂.1.2 H₂O: C, 54.56; H, 6.61; N, 13.87. Found: C, 54.58; H, 6.74; N, 13.76.

EXAMPLE 43

[({4-[({[(1R)-5-tert-butyl-2,3-dihydro-1H-inden-1-yl]amino}carbonyl)amino]-1H-indazol-1-yl}carbonyl)oxy]methylphosphonic acid, N-methyl-D-glucamine salt The title compound was prepared using the procedure as described in Example 39, substituting N-methyl-D-glucamine for triethylamine. $^1$H NMR (methanol-d₄) δ: 1.32 (s, 9H), 1.90 (m, 1H), 2.59 (m, 1H), 2.69 (s, 3H), 2.89 (m, 1H), 3.00 (m, 1H), 3.15 (d, 2H), 3.61-3.83 (m, 5H), 4.04 (m, 1H), 4.54 (d, 2H), 5.29 (t, 1H), 7.28 (s, 2H), 7.31 (s, 1H), 7.52 (t, 1H), 7.74 (d, 1H), 7.97 (d, 1H), 8.37 (s, 1H). Anal Calcd for C₂₃H₂₇N₄O₆P.1.3 C₇H₁₇NO₅.0.6 H₂O: C, 51.33; H, 6.75; N, 9.88. Found: C, 51.45; H, 6.61; N, 9.78.

EXAMPLE 47

N-[(1R)-5-tert-butyl-2,3-dihydro-1H-inden-1-yl]-N'-[1-(2-hydroxy-3-methoxypropyl)-1H-indazol-4-yl]urea A mixture of 2-methoxymethyl-oxirane (0.18 g, 4.0 mmol), Example 56J (0.35 g, 1.0 mmol) and K₂CO₃ (0.14 g, 1.0 mmol) in ethanol (4.0 mL) were heated at 120° C. for 10 minutes in the microwave (Personal Chemistry). After filtration, concentration of the filtrate and chromatography (ethyl acetate, 100%) two regioisomers were obtained: title compound (0.17 g, 26%) and compound described in Example 48 (0.11 g, 24%). MS (ESI) m/z: 437.14 [M+H]₊ $^1$H NMR (DMSO-d₆) 67: 1.28 (s, 9H), 1.84 (m, 1H), 2.45 (m, 1H), 2.84 (m, 1H), 2.94 (m, 1H), 3.25 (s, 3H), 4.05 (q, 1H), 4.28 (dd, 1H), 4.34 (dd, 1H), 5.06 (d, 1H), 5.16 (q, 1H), 6.66 (d, 1H), 7.15 (d, 1H), 7.24 (d, 1H), 7.27 (s, 2H), 7.31 (s, 1H), 7.68 (d, 1H), 8.02 (s, 1H), 8.55 (s, 1H).

EXAMPLE 48

N-[(1R)-5-tert-butyl-2,3-dihydro-1H-inden-1-yl]-N'-[2-(2-hydroxy-3-methoxypropyl)-2H-indazol-4-yl]urea The title compound was prepared and isolated as described in Example 47 with yield of 0.11 g (24%). MS (ESI) m/z: 437.13 [M+H]⁺ $^1$H NMR (DMSO-d₆) 67 : 1.28 (s, 9H), 1.82 (m, 1H), 2.44 (m, 1H), 2.84 (m, 1H), 2.94 (m, 1H), 3.22 (m, 1H), 3.29 (s, 3H), 4.05 (m, 1H), 4.31 (dd, 1H), 4.45 (dd, 1H), 5.13 (q, 1H), 5.27 (d, 1H), 6.56 (d, 1H), 7.13 (m, 2H), 7.26 (s, 2H), 7.30 (s, 1H), 7.52 (dd, 1H), 8.21 (s, 1H), 8.45 (s, 1H).

EXAMPLE 49 methyl 3-{4-[({[(1R)-5-tert-butyl-2,3-dihydro-1H-inden-1-yl]amino}carbonyl)amino]-1H-indazol-1-yl}-2-hydroxypropanoate A mixture of oxirane-2-carboxylic acid methyl ester (0.51 g, 5.0 mmol), Example 56J (0.35 g, 1.0 mmol) and sodium tert-butoxide (0.1 g, 1.0 mmol) in methanol (4.0 mL) was heated at 120° C. for 30 minutes in microwave (Personal Chemistry). After filtration, concentration of the filtrate and chromatography (ethyl acetate:dichloromethane 1:1 to 3:1) two regioisomers were obtained: title compound (0.18 g, 40%) and compound described in Example 50 (0.12 g, 27%). MS (ESI) m/z: 451.12 [M+H]⁺. $^1$H NMR (DMSO-d₆) δ: 1.28 (s, 9H), 1.84 (m, 1H), 2.44 (m, 1H), 2.84 (m, 1H), 2.94 (m, 1H), 3.60 (s, 3H), 4.49-4.64 (m, 3H), 5.14 (q, 1H), 6.65 (d, 1H), 7.13 (d, 1H), 7.22 (d, 1H), 7.27 (s, 2H), 7.31 (s, 1H), 7.68 (d, 1H), 8.02 (s, 1H), 8.56 (s, 1H).

EXAMPLE 50 methyl 3-{4-[({[(1R)-5-tert-butyl-2,3-dihydro-1H-inden-1-yl]amino}carbonyl)amino]-2H-indazol-2-yl}-2-hydroxypropanoate The title compound was prepared and isolated as described in Example 49 with yield of 0.12 g (27%). MS (ESI) m/z: 451.11 [M+H]⁺ $^1$H NMR (DMSO-d₆) 67 : 1.28 (s, 9H), 1.81 (m, 1H), 2.47 (m, 1H), 2.84 (m, 1H), 2.93 (m, 1H), 3.67 (s, 3H), 4.56 (m, 2H), 4.67 (m, 1H), 5.13 (q, 1H), 6.56 (d, 1H), 7.11 (d, 2H), 7.26 (s, 2H), 7.30 (s, 1H), 7.53 (t, 1H), 8.21 (s, 1H), 8.46 (s, 1H).

EXAMPLE 51 tert-butyl 3-{4-[({[(1R)-5-tert-butyl-2,3-dihydro-1H-inden-1-yl]amino}carbonyl)amino]-1H-indazol-1-yl}-2-hydroxypropylcarbamate A mixture of oxiranylmethyl-carbamic acid tert-butyl ester (0.35 g, 2.0 mmol), Example 56J (0.35 g, 1.0 mmol) and K₂CO₃ (0.14 g, 1.0 mmol) in acetonitrile (4.0 mL) were heated at 120° C. for 15 minutes in the microwave (Personal Chemistry). The reaction mixture was cooled, filtered and concentrated. The crude material was purified on silica gel (ethyl acetate/hexane 65/35 to 80/20) to provide the title compound (0.12 g, 23%). MS (ESI) m/z: 522.15 [M+H]+ 1H NMR (DMSO-d$_6$) 67 : 1.28 (s, 9H), 1.38 (s, 9H), 1.84 (m, 1H), 2.45 (m, 1H), 2.84 (m, 1H), 2.99 (m, 3H), 3.92 (m, 1H), 4.23 (dd, 1H), 4,29 (dd, 1H), 5.01 (d, 1H), 5.14 (q, 1H), 6.66 (d, 1H), 6.80 (t, 1H), 7.13 (d, 1H), 7.22 (d, 1H), 7.27 (s, 2H), 7.31 (s, 1H), 7.68 (d, 1H), 8.02 (s, 1H), 8.56 (s, 1H).

EXAMPLE 52

3-{4-[({[(1R)-5-tert-butyl-2,3-dihydro-1H-inden-1-yl]amino}carbonyl)amino]-1H-indazol-1-yl}-2-hydroxypropanoic acid A solution of compound from Example 49 (0.31 g, 0.68 mmol) in methanol (20 mL) was treated with 1N NaOH (2 mL) for 16 hours. The mixture was cooled in ice bath, treated with 1N HCl (2 mL) and concentrated under reduced pressure. The residue was dissolved in dimethyl sulfoxide-methanol, 1:1 (3 mL), filtered and the filtrated purified by HPLC (eluted with water/acetonitrile 10 to 100% contains 0.1% trifluoroacetic acid) (0.12 g, 27%). MS (ESI) m/z: 437.11 [M+H]+ 1H NMR (DMSO-d$_6$) δ: 1.28 (s, 9H), 1.84 (m, 1H), 2.45 (m, 1H), 2.84 (m, 1H), 2.94 (m, 1H), 4.40-4.62 (m, 3H), 5.14 (q, 1H), 6.65 (d, 1H), 7.15 (d, 1H), 7.22 (d, 1H), 7.27 (s, 2H), 7.31 (s, 1H), 7.68 (d, 1H), 8.03 (s, 1H), 8.56 (s, 1H).

EXAMPLE 53

3-{4-[({[(1R)-5-tert-butyl-2,3-dihydro-1H-inden-1-yl]amino}carbonyl)amino]-2H-indazol-2-yl}-2-hydroxypropanoic acid The title compound was prepared using the procedure as described in Example 52, substituting Example 50 for Example 49. MS (ESI) m/z: 437.11 [M+H]+ 1H NMR (DMSO-d$_6$) 67 : 1.28 (s, 9H), 1.82 (m, 1H), 2.45 (m, 1H), 2.84 (m, 1H), 2.93 (m, 1H), 4.44 (dd, 1H), 4.52 (dd, 1H), 4.65 (dd, 1H), 5.13 (q, 1H), 6.57 (d, 1H), 7.11 (d, 2H), 7.26 (s, 2H), 7.30 (s, 1H), 7.54 (t, 1H), 8.23 (s, 1H), 8.47 (s, 1H).

EXAMPLE 54

N-[(1R)-5-tert-butyl-2,3-dihydro-1H-inden-1-yl]-N'-[2-(2-hydroxy-3-morpholin-4-ylpropyl)-2H-indazol-4-yl]urea Charged an Emrys 5 mL process vial with 350 mg (1.0 mmol) Example 56J, 290 mg (2.0 mmol) 4-[(±)-2,3-epoxypropyl]-morpholine, 139 mg (1.0 mmol) K$_2$CO$_3$ and 4 mL ethanol. The mixture was heated in a microwave at 120° C. for 30 minutes, filtered, rinsed with ethanol and concentrated. The ~1:1 mixture of regioisomers was purified on silica gel with 5-10% methanol in ethyl acetate to obtain 0.32 g of the title compound and 0.45 g of the compound described in Example 55. MS (ESI) m/z: 492.18 [M+H]+ 1H NMR (DMSO-d$_6$) 67 : 1.28 (s, 9H), 1.80 (m, 1H), 2.32 (dd, 2H), 2.42 (dd, 4H), 2.47 (m, 1H), 2.84 (m, 1H), 2.93 (m, 1H), 3.57 (dd, 4H), 4.08 (m, 1H), 4.23 (dd, 1H), 4.51 (dd, 1H), 5.07 (d, 1H), 5.13 (q, 1H), 6.57 (d, 1H), 7.12 (m, 2H), 7.26 (s, 2H), 7.30 (s, 1H), 7.51 (dd, 1H), 8.24 (s, 1H), 8.47 (s, 1H).

EXAMPLE 55

N-[(1R)-5-tert-butyl-2,3-dihydro-1H-inden-1-yl]-N'-[1-(2-hydroxy-3-morpholin-4-ylpropyl)-1H-indazol-4-yl]urea The title compound was prepared and isolated as described in Example 54 with yield of 0.45 g MS (ESI) m/z: 492.19 [M+H]+ 1H NMR (DMSO-d$_6$) 67 : 1.28 (s, 9H), 1.84 (m, 1H), 2.29 (dd, 2H), 2.36 (dd, 4H), 2.44 (m, 1H), 2.84 (m, 1H), 2.94 (m, 1H), 3.52 (dd, 4H), 4.08 (m, 1H), 4.23 (dd, 1H), 4.39 (dd, 1H), 4.85 (m, 1H), 5.14 (q, 1H), 6.71 (d, 1H), 7.15 (d, 1H), 7.21 (d, 1H), 7.27 (s, 2H), 7.31 (s, 1H), 7.67 (d, 1H), 8.02 (s, 1H), 8.59 (s, 1H).

EXAMPLE 56

N-[(1R)-5-tert-butyl-2,3-dihydro-1H-inden-1-yl]-N'-1H-indazol-4-ylurea

EXAMPLE 56A 4-nitro-1H-indazole

2-Methyl-3-nitroaniline (20 g, 129.0 mmol) in acetic acid (~200 mL) was treated with NaNO$_2$ (20 g, 290.0 mmol) in water (50 mL) at 4° C. with mechanical stirring. The reaction mixture was allowed to warm to room temperature and stir overnight. The solvent was removed under reduced pressure. The residue was treated with water (700 mL) and the mixture was filtered. The solid was dried at 45° C. in a vacuum oven overnight to provide the title compound. 1H NMR (DMSO-d$_6$) δ 8.56 (s, 1H), 8.2-8.05 (dd, 2H), 7.6 (t, 1H).

EXAMPLE 56B methyl 4-nitro-1H-indazole-1-carboxylate

NaH (0.3 g, 12.5 mmol) in N,N-dimethylformamide (5 mL) was treated with Example 56A (1.33 g, 10 mmol) at 0° C. The reaction mixture was allowed to warm to room temperature and stir for 1 hour. The mixture was treated with methyl chloroformate (0.9 mL, 11.7 mol) and stirred at room temperature for 3 hours. The mixture was treated with water and filtered to provide the title compound as a solid. 1H NMR (300 MHz, DMSO-d$_6$) 67 4.19 (s, 3H), 7.9 (t, 1H), 8.38 (d, 1H), 8.62 (d, 1H), 8.85 (s, 1H).

EXAMPLE 56C methyl 4-amino-1H-indazole-1-carboxylate

Example 56B (1.66 g, 7.5 mmol) and 10% Pd/C were combined in ethanol (20 mL) and exposed to a hydrogen atmosphere. The reaction mixture was heated at 80° C. for 20 minutes, allowed to cool to room temperature, and filtered through Celite. The filtrate was evaporated to provide title compound. 1H NMR (300 MHz, DMSO-d$_6$) δ 6.1 (s, 2H), 6.41 (dd, 1H), 7.21 (m, 2H), 8.42 (s, 1H).

EXAMPLE 56D 1-(4-tert-butylphenyl)-3-chloro-1-propanone

A solution of tert-butyl benzene (31 ml, 200 mmol) and 3-chloro-propionyl chloride (19 ml, 200 mmol) in methylene chloride (75 ml) was added dropwise to a suspension of aluminum chloride (29.33 g, 220 mmol) in methylene chloride (300 ml) at 0° C. The reaction mixture was allowed to warm to ambient temperature, stirred for 16 hours, and quenched with water dropwise. The reaction mixture was washed with water, dried with magnesium sulfate, and the filtrate was evaporated under reduced pressure to provide the title compound which was used without further purification in the next step.

EXAMPLE 56E

5-tert-butyl-1-indanone

Example 56D (22.25 g, 99 mmol) was dissolved in concentrated sulfuric acid (100 ml) and heated on a water bath at 95° C. for 2.5 hours. The reaction mixture was cooled, poured onto ice, and extracted with diethyl ether. The combined organic extracts were washed with saturated aqueous sodium bicarbonate, dried with magnesium sulfate, and the filtrate was evaporated under reduced pressure to provide the title compound which was used without further purification in the next step.

EXAMPLE 56F

5-tert-butyl-1-indanone O-methyloxime

Example 56E (13.41 g, 71.23 mmol) and methoxyamine hydrochloride (6.68 g, 80 mmol) were dissolved in pyridine (75 ml) and stirred at ambient temperature for 16 hours. The mixture was evaporated under reduced pressure and the residue was partitioned between water and diethyl ether. The combined organic layers were washed with 1N aqueous hydrochloric acid, dried with magnesium sulfate, and the filtrate was evaporated under reduced pressure to provide the title compound which was used without further purification in the next step.

EXAMPLE 56G

5-tert-butyl-2,3-dihydro-1H-inden-1-ylamine

Example 56F (4.37 g, 20.2 mmol) and 10% palladium on carbon (2.2 g) were combined in methanol (50 ml) and ammonia (10 ml) and placed in a Parer apparatus which was charged with hydrogen to 60 psi. The reaction was shaken at 50° C. for 16 hours. The reaction mixture was filtered and the filtrate was evaporated under reduced pressure. The residue was treated with diethyl ether (100 ml) and extracted with hydrochloric acid (1N, 3×50 ml). The combined aqueous extracts were neutralized with sodium hydroxide (6 g) in water (25 ml) and extracted with diethyl ether. The organic extracts were combined, dried with magnesium sulfate, and the filtrate was evaporated under reduced pressure to provide the title compound which was used without further purification in the next step.

EXAMPLE 56H

(1R)-5-tert-butyl-2,3-dihydro-1H-inden-1-ylamine

Example 56G (11.70 g, 61.9 mmol, 44.4% ee), N-acetyl-(D)-leucine (11.78 g 68.1 mmol) and methanol (120 mL) were combined and heated at 65° C. for 1 hour. The solution was allowed to cool to ambient temperature. The solids were filtered and washed with toluene. The solid was then resuspended in methanol (125 mL) and brought to reflux. The solution was allowed to cool to ambient temperature and the solids were filtered. The solid was dried at 40° C. under reduced pressure to provide the title compound. The solid was treated with 1N NaOH (100 mL) and extracted with methyl-t-butyl ether. Organic phase was concentrated to obtain free base (3.8 g, 98.7% ee, determined by chiral HPLC with Chirobiotic column from Astec using mobile phase of 0.1% acetic acid and 0.06% triethylamine in methanol) (98.7% ee)

EXAMPLE 56I methyl 4-[({[(1R)-5-tert-butyl-2,3-dihydro-1H-inden-1-yl]amino}carbonyl)amino]-1H-indazole-1-carboxylate Example 56C (4.59 g, 24 mmol) in toluene (800 ml) was treated with phosgene (20% in toluene, 25.4 ml, 48 mmol). The mixture was heated at reflux for 3 hours, cooled, and the solvent removed under vacuum. The residue in diethyl ether (800 ml) and triethyl amine (20 ml) was filtered and then treated with Example 56H (3.78 g, 20 mmol). After stirring at ambient temperature for 16 hours, the solvent was removed under vacuum and the residue triturated with a 1:1 mixture of diethyl ether and hexanes to provide the title compound. $^1$H NMR (DMSO-$d_6$) 67 1.28 (s, 9H), 1.78-1.91 (m, 1H), 2.39-2.48 (m, 1H), 2.75-2.88 (m, 1H), 2.91-3.02 (m, 1H), 4.04 (s, 3H), 5.17 (m, 1H), 6.73 (d, 1H), 7.27 (s, 2H), 7.30 (m, 1H), 7.50 (m, 1H), 7.69 (d, 1H), 7.88 (d, 1H), 8.39 (s, 1H), 8.84 (s, 1H); MS (ESI+) 407 (M+H)$^+$; Elemental: Calculated for $C_{23}H_{26}N_4O_3$: C,67.96, H,6.45, N,13.78. Found: C, 67.85; H, 6.51; N, 13.56.

EXAMPLE 56J

N-[(1R)-5-tert-butyl-2,3-dihydro-1H-inden-1-yl]-N'-1H-indazol-4-ylurea

Example 56I (5.67 g, 14 mmol) in tetrahydrofuran (20 ml) was treated with A 5M solution of sodium hydroxide in methanol (8 ml, 40 mmol). After stirring for 30 minutes, the reaction mixture was diluted with water and filtered. The solid was air-dried to obtain desired compound. $^1$H NMR (DMSO-$d_6$) 67 1.27 (s, 9H), 1.75-1.88 (m, 1H), 2.40-2.48 (m, 1H), 2.76-2.88 (m, 1H), 2.90-3.01 (m, 1H), 5.15 (m, 1H), 6.84 (br, 1H), 7.05 (d, 1H), 7.20, (m, 1H), 7.26 (s, 2H), 7.31 (s, 1H), 7.69 (d, 1H), 8.17 (s, 1H), 8.83 (s, 1H); MS (ESI+): 349 (M+H)$^+$; Elemental: Calculated for $C_{21}H_{24}N_4O$.HCl: C,65.53; H, 6.55; N, 14.56. Found: C, 65.29; H, 6.63; N, 14.23.

EXAMPLE 56K

(1R)-5-tert-butyl-indan-1-ylamine tosylate salt

A solution of the product from Example 56H (1.9 g, 10 mmol) in methanol (25 mL) was added to a solution of p-toluenesulfonic acid (1.76 g, 10.5 mmol) in methanol (5 mL). The resultant solution was distilled under reduced pressure to approximately 5 mL. The internal temperature was adjusted to ~65° C., and water (50 mL) was added while maintaining the internal temperature at 60° C. The product crystallized during the addition. The mixture was held at ~65° C. for 1 h, then gradually cooled to ~20° C. After stirring at ~20° C. for 2 h, the suspension was filtered through a polypropylene pad to collect the crude product The wetcake was washed with water and dried to obtain title compound (2.81 g, 80%).

EXAMPLE 57

N-[(1R)-5-tert-butyl-2,3-dihydro-1H-inden-1-yl]-N'-{1-[(4-methylpiperazin-1-yl)carbonyl]-1H-indazol-4-yl}urea A solution of the product from Example 56J (240 mg, 0.69 mmol) in N,N-dimethylformamide (5 mL) was treated with 60% NaH (45 mg, 1.13 mmol) and stirred at room temperature for 15 min. 4-methylpiperazine carbonyl chloride (1.64 mmol) was then added, and the reaction mixture was stirred overnight at 80° C. It was then cooled to room temperature and poured into $H_2O$, and the resulting precipitate was collected by filtration. Chromatography on silica gel (eluted with 97:3 $CH_2Cl_2$-methanol) afforded the desired product. 1H NMR ($d_6$-DMSO) 67 8.59 (s, 1H), 8.07 (s, 1H), 7.72 (d, J=7.5 Hz, 1H), 7.28 (m, 3H), 7.17 (d, J=7.5 Hz, 1H), 6.66 (d, J=7.5 Hz, 1H), 5.17 (m, 1H), 4.44 (m, 2H), 3.48 (m, 2H), 3.02 (m, 1H), 2.90 (m, 1H), 2.81 (m, 1H), 2.53 (s, 3H), 2.42 (m, 1H), 1.80 (m, 1H), 1.27 (s, 9H). MS (DCI) m/z 475 (M+H). $C_{27}H_{34}N_6O_2 \cdot 0.5H_2O$: C, 67.06; H, 7.29; N, 17.38. Found: C, 66.87; H, 7.22; N, 17.04.

EXAMPLE 58

N-[(1R)-5-tert-butyl-2,3-dihydro-1H-inden-1-yl]-N'-{2-[(4-methylpiperazin-1-yl)carbonyl]-2H-indazol-4-yl}urea The title compound was prepared and isolated as described in Example 57. $^1$H NMR ($d_6$-DMSO) 67 8.43 (s, 1H), 8.20 (s, 1H), 7.51 (d, J=1.0 and 7.5 Hz, 1H), 7.31 (s, 1H), 7.25 (m, 2H), 7.17 (m, 2H), 6.58 (d, J=7.5 Hz, 1H), 5.17 (m, 1H), 4.53 (m, 2H), 3.60 (m, 2H), 3.11 (m, 2H), 3.00 (m, 2H), 2.92 (m, 1H), 2.81 (m, 1H), 2.60 (s, 3H), 2.42 (m, 1H), 1.80 (m, 1H), 1.24 (s, 3H). MS (DCI) m/z 475 (M+H). $C_{27}H_{34}N_6O_2 \cdot 0.8H_2O$: C, 66.32; H, 7.34; N, 17.19. Found: C, 66.62; H, 7.29; N; 16.78.

EXAMPLE 59

N-[(1R)-5-tert-butyl-2,3-dihydro-1H-inden-1-yl]-N'-[1-(N,N-dimethylglycyl)-1H-indazol-4-yl]urea To a 200 mL round bottom flask was added 1-hydroxybenzotriazole (HOBT) (3.50 mmol, 0.47 g), 1-ethyl-3-(3-dimethylaminopropyl)-carbodiimide hydrochloride (EDCI) (3.50 mmol, 0.67 g), N,N-dimethylglycine (2.90 mmol, 0.30 g) and methylene chloride (36 mL) and the reaction was stirred at room temperature for 10 minutes. To the flask was then added Example 56J (2.90 mmol, 1.10 g) in 4 mL of DMF and the reaction was stirred at room temperature for 24 hours. The reaction was not complete after 24 hours so another equivalent of HOBT and EDCI was added and stirred at room temperature for 24 hours. The reaction was diluted with methylene chloride (100 mL) and the organic layer was washed with saturated sodium bicarbonate (100 mL), dried (sodium sulfate) and concentrated in vacuo. The material was purified on $SiO_2$ and eluted with ethyl acetate to give a oily white solid in 62%. $^1$H NMR (DMSO-$d_6$, 300 MHz); 67 1.28 (s, 9H), 1.79-1.91 (m, 1H), 2.38 (s, 6H), 2.73-3.01(m, 3H), 4.04 (s, 2H), 5.13-5.20 (m, 1H), 6.70 (d, J=7.8Hz, 1H), 7.27-7.54 (m, 3H), 7.51 (t, J=8.14, 16.28, 1H), 7.88 (t, J=8.48, 13.91 Hz, 2H), 8.38 (s, 1H), 8.84 (s, 1H). DCI/NH$_3$ m/z 434.

EXAMPLE 60

N-[(1R)-5-tert-butyl-2,3-dihydro-1H-inden-1-yl]-N'-[1-(N,N-dimethylglycyl)-1H-indazol-4-yl]urea, hydrochloride salt The solid from Example 59 was taken up in ethyl acetate/diethyl ether (1/10) (20 mL) and 2N HCl in diethyl ether (2.0 eq) was added dropwise and the mixture was stirred for 5 minutes. The reaction was concentrated in vacuo to give the title compound as a white solid. $^1$H NMR (DMSO-$d_6$, 300 MHz); δ1.28 (s, 9H), 1.77-1.83 (m, 1H), 2.42-2.53 (m, 1H), 2.73-2.94 (m, 2H), 2.97 (s, 6H), 5.02 (s, 2H), 5.14-5.21 (m, 1H), 7.25-7.35 (m, 4H), 7.58 (t, J=7.80, 15.94 Hz, 1H), 7.83 (d, J=8.14 Hz, 1H), 8.03 (d, J=8.14 Hz, 1H), 8.93(s, 1H), 9.77 (s, 1H). Calc for $C_{25}H_{31}N_5O_2 \cdot 1.7HCl$: C, 60.60; H, 6.65; N, 14.13. Found: C, 60.91; H, 6.87; N, 13.85. MS (DCI/NH$_3$) m/z 434.

EXAMPLE 61

(R)-1-(5-tert-Butyl-2,3-dihydro-1H-inden-1-yl)-3-(1-(2-(2-methoxyethoxy)acetyl)-1H-indazol-4-yl)urea

EXAMPLE 61A

4-Nitrophenyl 2-(2-methoxyethoxy)acetate 2-(2-methoxyethoxy)acetic acid (Alfa, 2.68 g, 20 mmol) was dissolved in dichloromethane (60 mL), and oxalyl chloride (5.2 mL, 60 mmol) was added with a few drops of dimethylformamide. The mixture was stirred for one hour, concentrated to a yellow slurry and dichloromethane (40 mL) was added. 4-nitrophenol (Aldrich, 2.78 g, 20 mmol) was dissolved in pyridine (2.4 mL, 30 mmol) and dichloromethane (60 mL), and then the (2-methoxyethoxy)acetyl chloride solution was added and the mixture was stirred for one hour. A solution of 1:1 ethyl acetate:hexane was added which precipitated the salts, which were then filtered through a silica gel plug. The filtrate was concentrated to a yellow oil and chromatographed on silica gel with 0-to-60% ethyl acetate in hexane. Obtained 4.33 g (85% yield) of Example 61A as a yellow solid. $^1$H NMR (300 MHz, DMSO-$d_6$) δ ppm 3.26 (s, 3H), 3.50 (m, 2H), 3.71 (m, 2H), 4.48 (s, 2H), 7.49 (d, J=9.15 Hz, 2H), 8.32 (d, J=9.15 Hz, 2H). MS (DCI) mn/z 273.08 (M+NH$_4$)$^+$.

EXAMPLE 61B (R)-1-(5-tert-Butyl-2,3-dihydro-1H-inden-1-yl)-3-(1-(2-(2-methoxyethoxy)acetyl)-1H-indazol-4-yl)urea Example 56J (1.74 g, 5.0 mmol) was dissolved in tetrahydrofuran (80 mL), and then potassium tert-butoxide (1.0 M in THF, 5.5 mL, 5.5 mmol) was added. The solution stirred for 5 minutes, Example 61A (1.40 g, 5.5 mmol) was added in tetrahydrofuran (20 mL), and the solution was stirred for another 15 minutes. Ethyl acetate was added, the salts precipitated, and the mixture was filtered through a silica gel plug. The filtrate was concentrated and chromatographed on silica gel using 0-to-35% ethyl acetate in dichloromethane as the eluent. Obtained 1.227 g (53% yield) of Example 61B as a solid. $^1$H NMR (300 MHz, DMSO-$d_6$) δ ppm 1.28 (s, 9H), 1.85 (m, 1H), 2.45 (m, 1H), 2.82 (m, 1H), 2.96 (m, 1H), 3.27 (s, 3H), 3.53 (m, 2H), 3.75 (m, 2H), 4.98 (s, 2H), 5.16 (q, J=7.34 Hz, 1H), 6.69 (d, J=7.80 Hz, 1H), 7.27 (s, 2H), 7.31 (s, 1H), 7.52 (t, J=7.97 Hz, 1H), 7.86 (d, J=8.14 Hz, 1H), 7.89 (d, J=7.79 Hz, 1H), 8.39 (s, 1H), 8.85 (s, 1H). MS (ESI) m/z 465.32 (M+H)$^+$. Calcd for $C_{26}H_{32}N_4O_4 \cdot 0.22$ Ethyl acetate. 0.15 $H_2O$: C, 66.34; H, 7.11.51. Found: C, 66.32; H, 6.63; N, 11.45.

EXAMPLE 62

1-((R)-5-tert-Butyl-2,3-dihydro-1H-inden-1-yl)-3-(1-(3,5,5-trimethylhexanoyl)-1H-indazol-4-yl)urea

EXAMPLE 62A

4-Nitrophenyl 3,5,5-trimethylhexanoate

Dissolved 4-nitrophenol (Aldrich, 1.39 g, 10 mmol) in pyridine (1.2 mL, 15 mmol) and dichloromethane (50 mL), chilled to 0° C., then added 3,5,5-trimethylhexanoyl chloride (Aldrich, 1.9 mL, 10 mmol), warmed to ambient temperature and stirred for 1.5 hours. Added ethyl acetate, precipitated salts, and filtered through silica gel plug. Concentrated filtrate and chromatographed on silica gel with 0-to-20% ethyl acetate in hexane. Obtained 2.79 g (100% yield) of Example 62A as an oil. $^1$H NMR (300 MHz, DMSO-$d_6$) δ ppm 0.92 (s, 9H), 1.05 (d, J=6.78 Hz, 3H), 1.18 (dd, J=13.90, 6.44 Hz, 1H), 1.34 (dd, J=13.90, 4.07 Hz, 1H), 2.07 (m, 1H), 2.47 (dd, J=14.92, 7.80 Hz, 1H), 2.62 (dd, J=14.92, 6.11 Hz, 1H), 7.44 (d, J=9.16 Hz, 2H), 8.30 (d, J=9.16 Hz, 2H). MS (DCI) m/z 297.1 $(M+NH_4)^+$.

EXAMPLE 62B 1-((R)-5-tert-Butyl-2,3-dihydro-1H-inden-1-yl)-3-(1-(3,5,5-trimethylhexanoyl)-1H-indazol-4-yl)urea Dissolved Example 56J (1.394 g, 4.0 mmol) in tetrahydrofuran (50 mL), added potassium tert-butoxide (1.0 M in THF, 4.0 mL, 4.0 mmol), stirred for 5 minutes, then added Example 62A (1.229 g, 4.4 mmol) in tetrahydrofuran (20 mL). After stirring for 15 minutes, 1:1 ethyl acetate:hexane was added, the salts precipitated, and were filtered through a silica gel plug. Concentrated filtrate to a foam and chromatographed on silica gel using 0-to-30% ethyl acetate in hexane. Obtained 1.771 g (91 % yield) of Example 62B as a foam. $^1$H NMR (300 MHz, DMSO-$d_6$) δ ppm 0.88 (s, 9H), 1.02 (d, J=6.79 Hz, 3H), 1.19 (dd, J=6.78, 3.05 Hz, 1H), 1.28 (s, 9H), 1.36 (dd, J=14.07, 3.90 Hz, 1H), 1.84 (m, 1H), 2.23 (m, 1H), 2.45 (m, 1H), 2.82 (m, 1H), 2.95 (m, 1H), 3.05 (d, J=4.41 Hz, 1H), 3.08 (d, J=3.39 Hz, 1H), 5.16 (q, J=7.46 Hz, 1H), 6.69 (d, J=7.80 Hz, 1H), 7.27 (s, 2H), 7.31 (s, 1H), 7.50 (t, J=7.97 Hz, 1H), 7.88 (dd, J=8.14, 3.05 Hz, 2H), 8.39 (s, 1H), 8.82 (s, 1H). MS (ESI) m/z 489.42 $(M+H)^+$. Calcd for $C_{30}H_{40}N_4O_2 \cdot 0.19$ Ethyl acetate: C, 73.10; H 8.28, N 11.09. Found: C, 73.13; H, 8.12; N, 11.02.

EXAMPLE 63

2-Ethylhexyl 4-(3-((R)-5-tert-butyl-2,3-dihydro-1H-inden-1-yl)ureido)-1H-indazole-1-carboxylate Dissolved Example 56J (1.045 g, 3.0 mmol) in dimethylformamide (20 mL), added potassium tert-butoxide (1.0M in THF, 3.0 mL, 3.0 mmol), stirred the solution for 5 minutes, then added 2-ethylhexyl chloroformate (Aldrich, 0.65 mL, 3.3 mmol), and stirred solution for 20 minutes. The solution was partitioned between ethyl acetate (200 mL) and water (200 mL), the organic layer was washed with brine and sodium sulfate and then concentrated to an oil and chromatographed on silica gel with 0-to-50% ethyl acetate in hexane. Obtained 1.475 g (97% yield) of Example 63 as a foam. $^1$H NMR (300 MHz, DMSO-$d_6$) δ ppm 0.87 (m, 6H), 1.33 (m, 17H), 1.81 (m, 2H), 2.45 (m, 1H), 2.82 (m, 1H), 2.96 (m, 1H), 4.38 (dd, J=5.76, 1.70 Hz, 2H), 5.16 (q, J=7.12 Hz, 1H), 6.70 (d, J=7.80 Hz, 1H), 7.27 (s, 2H), 7.31 (s, 1H), 7.50 (t, J=8.14 Hz, 1H), 7.66 (d, J=8.48 Hz, 1H), 7.89 (d, J=7.79 Hz, 1H), 8.39 (s, 1H), 8.83 (s, 1H). MS (ESI) m/z 505.43 $(M+H)^+$. Calcd for $C_{30}H_{40}N_4O_3 \cdot 0.14$ Ethyl acetate: C, 71.00; H, 8.02N, 10.84. Found: C, 71.23; H, 8.36; N, 10.53.

EXAMPLE 64

(R)-1-(1-(2-(2-Butoxyethoxy)acetyl)-1H-indazol-4-yl)-3-(5-tert-butyl-2,3-dihydro-1H-inden-1-yl)urea

EXAMPLE 64A

4-Nitrophenyl 2-(2-butoxyethoxy)acetate

Dissolved 2-(2-butoxyethoxy)acetic acid (TCI, 3.654 g, 20.7 mmol) in dichloromethane (60 mL), added oxalyl chloride (5.4 mL, 62.2 mmol) and a few drops of dimethylformamide, stirred for 1 hour, concentrated to an oil and added dichloromethane (40 mL). This solution was added to a solution of 4-nitrophenol (Aldrich, 2.88 g, 20.7 mmol) in pyridine (2.5 mL, 31.1 mmol) and dichloromethane (60 mL) and stirred for 1.5 hours. Added 1:1 ethyl acetate:hexane, precipitated the salts, and filtered through a silica gel plug. Concentrated the filtrate to a yellow oil and chromatographed on silica gel with 0-to-30% ethyl acetate in hexane. Residue was dissolved in ethyl acetate (200 mL), washed with 0.5 M potassium carbonate (200 mL), dried with brine and sodium sulfate, and then evaporated. Recovered 5.63 g (91% yield) of Example 64A as an oil. $^1$H NMR (300 MHz, DMSO-$d_6$) δ ppm 0.87 (t, J=7.29 Hz, 3H), 1.30 (m, 2H), 1.48 (m, 2H), 3.40 (t, J=6.44 Hz, 2H), 3.54 (m, 2H), 3.71 (m, 2H), 4.88 (, 2H), 7.49 (d, J=9.16 Hz, 2H), 8.32 (d, J=9.16 Hz, 2H). MS (DCI) m/z 315.14 $(M+NH_4)^+$.

EXAMPLE 64B (R)-1-(1-(2-(2-Butoxyethoxy)acetyl)-1H-indazol-4-yl)-3-(5-tert-butyl-2,3-dihydro-1H-inden-1-yl)urea Dissolved Example 56J (2.09 g, 6.0 mmol) in tetrahydrofuran (100 mL), added potassium tert-butoxide (1.0 M in THF, 6.0 mL, 6.0 mmol), stirred solution for 5 minutes, and then added Example 64A (1.96 g, 6.6 mmol) in tetrahydrofuran (40 mL), and stirred mixture for 15 minutes. Added 1:1 ethyl acetate:hexane, precipitated the salts, and filtered through silica gel plug. Concentrated filtrate and chromatographed on silica gel with 0-to-30% ethyl acetate in dichloromethane. Dissolved solid in ethyl acetate (250 mL), washed with 0.5 M potassium carbonate (200 mL), dried with brine, filtered through a silica gel plug, and concentrated the filtrate. Recovered 2.13 g (70% yield) of Example 64B as a solid. $^1$H NMR (300 MHz, DMSO-$d_6$) δ ppm 0.82 (t, J=7.29 Hz, 3H), 1.28 (m, 11H), 1.41 (m, 2H), 1.86 (m, 1H), 2.45 (m, 1H), 2.82 (m, 1H), 2.96 (m, 1H), 3.38 (t, J=6.44 Hz, 2H), 3.56 (m, 2H), 3.75 (m, 2H), 4.99 (s, 2H), 5.16 (q, J=7.12 Hz, 1H), 6.70 (d, J=7.80 Hz, 1H), 7.27 (s, 2H), 7.31 (s, 1H), 7.52 (t, J=7.97 Hz, 1H), 7.86 (d, J=8.14 Hz, 1H), 7.90 (d, J=7.80 Hz, 1H), 8.39 (s, 1H), 8.86 (s, 1H). MS (ESI) m/z 507.43 $(M+H)^+$. Calcd for $C_{29}H_{38}N_4O_4 \cdot 0.25$ Ethyl acetate: C, 68.16; H, 7.63; N, 10.60. Found: C, 68.16; H, 7.74; N, 10.61.

EXAMPLE 65

1-(7-fluoro-2,2-dimethylchroman-4-yl)-3-(1-(2-methoxyethyl)-1H-indazol-4-yl)urea

EXAMPLE 65A 7-fluoro-2,2-dimethylchroman-4-one

A mixture of 4-fluoro-2-hydroxyacetophenone (Aldrich, 1.54 g, 10 mmol), acetone (0.95 mL, 12.9 mmol), and pyrrolidine (0.83 mL, 9.94 mmol) was stirred in 3 mL toluene at room temperature for 1 h and at reflux (Dean-Stark trap) for 4 hours. After cooling to room temperature, the mixture was diluted with ether (30 mL) and was washed with 2N HCl (10 mL) and $H_2O$ (10 mL). Drying over $Na_2SO_4$ and evaporation of volatiles in vacuo afforded the crude title compound, which was used without further purification.

EXAMPLE 65B 7-fluoro-2,2-dimethylchroman-4-amine

To a solution of Example 65A (415 mg, 2.14 mmol) in methanol (12 mL) was added methoxylamine hydrochloride (0.179 g, 2.14 mmol) and pyridine (0.87 mL, 10.8 mmol). The mixture was stirred overnight at room temperature and was then evaporated in vacuo. The residue was partitioned between ethyl acetate and $H_2O$, and the organic layer was dried over $Na_2SO_4$ and was evaporated in vacuo. The residue thus obtained was dissolved in methanol (8 mL) and was hydrogenated (balloon) over 10% Pd-C in the presence of 4 drops of concentrated HCl overnight at room temperature. The catalyst was filtered off (Celite), and the filtrate was evaporated in vacuo. The residue was taken up in ether (20 mL) and was extracted with 1N HCl (3×10 mL). These acidic extracts were then basified to pH 10 with 2N NaOH and were extracted with ethyl acetate (3×10 mL). Drying over $Na_2SO_4$, followed by evaporation in vacuo, yielded Example 65B, 158 mg (48%). $^1$H NMR (300 MHz, DMSO-$d_6$) δ ppm 7.56 (m, 1H), 6.66 (m, 1H), 6.48 (m, 1H), 3.81 (m, 1H), 2.02 (m, 2H), 1.35 (s, 3H), 1.20 (s, 3H). MS (ESI) m/z 196 (M+H).

EXAMPLE 65C methyl 4-(3-(7-fluoro-2,2-dimethylchroman-4-yl)ureido)-1H-indazole-1-carboxylate Example 65B (158 mg, 0.81 mmol) was stirred with Example 66E (269 mg, 0.81 mmol) and DIEA (0.21 mL, 1.21 mmol) in 2 mL DMF at room temperature for 2 hours. The DMF was removed in vacuo, and the residue was diluted with $H_2O$. The precipitate thus formed was collected by filtration and was air-dried to afford the title compound, which was used without further purification.

EXAMPLE 65D 1-(7-fluoro-2,2-dimethylchroman-4-yl)-3-(1H-indazol-4-yl)urea

Example 65C (2.35 mmol, 0.57 mmol) was suspended in methanol (5 mL) and was treated with 5N methanolic NaOH (0.6 mL, 3.0 mmol). The mixture was stirred at room temperature for 30 minutes, and poured into $H_2O$ (30 mL). The precipitate was collected by filtration and was air-dried to afford the title compound, 68 mg (34%). 1H NMR (300 MHz, DMSO-$d_6$) δ ppm 13.02 (br, 1H), 8.72 (s, 1H), 8.31 (s, 1H), 7.67 (d, J=6.8 Hz, 1H), 7.36 (m, 1H), 7.22 (m, 1H), 7.09 (m, 1H), 6.59-6.72 (m, 3H), 4.97 (m, 1H), 2.22 (m, 1H), 1.78 (m, 1H), 1.42 (s, 3H), 1.30 (s, 3H). MS (ESI) m/z 355 (M+H).

EXAMPLE 65E 1-(7-fluoro-2,2-dimethylchroman-4-yl)-3-(1-(2-methoxyethyl)-1H-indazol-4-yl)urea A solution of Example 65D (500 mg, 1.41 mmol) in DMF (7 mL) was treated with 60% sodium hydride (68 mg, 1.7 mmol) at room temperature, and the mixture was stirred at this temperature for 1 hour. Bromoethyl methyl ether (0.15 mL, 1.6 mmol) was then added, and the mixture was stirred overnight at room temperature. After this time, most of the DMF was evaporated in vacuo, then water (50 mL) was added. The resulting sticky residue was collected by filtration and was then chromatographed on silica gel (98:2 $CH_2Cl_2$—$CH_3OH$) to afford the title compound, 131 mg (23%). $^1$H NMR (300 MHz, DMSO-$d_6$) δ ppm 8.73 (s, 1H), 8.07 (s, 1H), 7.69 (d, J=6.44 Hz, 1H), 7.32 (dd, J=15.09, 7.63 Hz, 1H), 7.18-7.26 (m, 2H), 6.71-6.79 (m, 2H), 6.61 (dd, J=10.85, 2.71 Hz, 1H), 4.96 (m, 1H), 4.51 (t, J=5.43 Hz, 2H), 3.75 (t, J=5.43 Hz, 2H), 3.18 (s, 3H), 2.20 (dd, J=13.39, 6.27 Hz, 1H), 1.78 (dd, J=13.05, 11.02 Hz, 1H), 1.41 (s, 3H), 1.30 (s, 3H). MS (ESI$^+$) m/z 413 (M+H), 435 (M+Na).

EXAMPLE 66

3-(Dimethylamino)propyl 4-(3-(4-cyclopropyl-5-fluoro-2,3-dihydro-1H-inden-1-yl)ureido)-1H-indazole-1-carboxylate

EXAMPLE 66A

4-Bromo-5-fluoro-2,3-dihydro-1H-inden-1-one

5-Fluoro-1-indanone (Aldrich, 6.0 g, 40 mmol) was charged in three portions to aluminum chloride (13.32 g, 100 mmol). After mixing by mechanical stirrer for 40 minutes, bromine (2.5 mL, 48 mmol) was added over 15 minutes. The mixture was heated in a hot water bath (internal temperature 45-50° C.) for 2 hours. More bromine (0.1 mL) was added via syringe, then heating continued for another 30 minutes. The solution was poured onto a mixture of 12N hydrochloric acid (16 mL) and ice (80 g). The residual tar in the flask was rinsed out with the quenched solution. The product was extracted into ethyl acetate and the combined organic layers were washed twice with water (60 mL), dried over sodium sulfate, and concentrated. The product was isolated by flash chromatography on silica gel with 10% ethyl acetate in heptane. Obtained 5.90 g (64.5% yield) of Example 66A as a light yellow solid. $^1$H NMR (300 MHz, DMSO-$d_6$) δ 2.73 (t, J=5.77 Hz, 2H), 3.04 (t, J=5.77 Hz, 2H), 7.44 (t, J=8.48 Hz, 1H), 7.70 (dd, J=8.31, 4.92 Hz, 1H). MS (DCI) m/z 247.89 (M+NH$_4$)$^+$.

EXAMPLE 66B

4-Bromo-5-fluoro-2,3-dihydro-1H-inden-1-one O-methyl oxime

Methoxylamine hydrochloride (1.92 g, 22.9 mmol) was added to Example 66A (4.777 g, 20.9 mmol) in pyridine (30 mL) and stirred for 3 hours at ambient temperature. Concentrated the mixture to a slurry, added ethyl acetate (200 mL), washed with 1N hydrochloric acid (200 mL), dried with brine, filtered through a silica gel plug, and concentrated the filtrate. Obtained 5.186 g (96% yield) of Example 66B. $^1$H NMR (300 MHz, DMSO-$d_6$) δ ppm 2.86 (m, 2H), 2.99 (m, 2H), 3.90 (s, 3H), 7.29 (t, J=8.65 Hz, 1H), 7.57 (dd, J=8.48, 5.09 Hz, 1H). MS (DCI) m/z 259.83 (M+H)$^+$.

EXAMPLE 66C

4-Cyclopropyl-5-fluoro-2,3-dihydro-1H-inden-1-one O-methyl oxime

Example 66B (1.29 g, 5.0 mmol) was added to a mixture of cyclopropylboronic acid (Aldrich, 558 mg, 6.5 mmol), potassium phosphate (3.71 g, 17.5 mmol), palladium(II) acetate (56 mg, 0.25 mmol) and tricyclohexylphosphine (140 mg, 0.5 mmol) in toluene (20 mL) with water (1 mL). Heated the mixture at 100° C. for 1.5 hours on the microwave (Personal Chemistry). After cooling, the mixture was filtered through celite and rinsed with ethyl acetate. Concentrated the filtrate to an oil and chromatographed on silica gel with 0-to-15% ethyl acetate in hexane. Obtained 1.03 g (94% yield) of Example 66C. $^1$H NMR (300 MHz, DMSO-$d_6$) δ ppm 0.81 (m, 2H), 0.93 (m, 2H), 1.76 (m, 1H), 2.82 (m, 2H), 3.06 (m, 2H), 3.87 (s, 3H), 7.03 (dd, J=11.19, 8.48 Hz, 1H), 7.39 (dd, J=8.31, 4.92 Hz, 1H). MS (DCI) m/z 220.07 (M+H)$^+$.

EXAMPLE 66D

4-Cyclopropyl-5-fluoro-2,3-dihydro-1H-inden-1-amine

Example 66C (1.03 g, 4.7 mmol), Raney nickel (10 g), and 20% ammonia in methanol (90 mL) were shaken under hydrogen (60 psi) for 4 hours at ambient temperature. The catalyst was removed by filtration and the solvent evaporated under reduced pressure, giving 828 mg (92% yield) of Example 66D as a light yellow oil. $^1$H NMR (300 MHz, DMSO-$d_6$) δ ppm 0.73 (m, 2H), 0.88 (m, 2H), 1.59 (m, 1H), 1.73 (m, 1H), 1.85 (br s, 2H), 2.34 (m, 1H), 2.70 (m, 1H), 2.96 (ddd, J=16.02, 8.73, 3.05 Hz, 1H), 4.11 (t, J=7.46 Hz, 1H), 6.88 (dd, J=11.36, 8.31 Hz, 1H), 7.14 (dd, J=8.14, 5.09 Hz, 1H). MS (DCI) m/z 192.0 (M+H)$^+$.

EXAMPLE 66E

Methyl 4-({[(2,5-dioxopyrrolidin-1-yl)oxy]carbonyl}amino)-1H-indazole-1-carboxylate Example 56C (1.9 g, 10 mmol) and disuccinimidyl carbonate (Fluka, 2.8 g, 11 mmol) were mixed in acetonitrile (100 mL) for 48 hours under nitrogen atmosphere. The solid was isolated by filtration, washed with acetonitrile (10 mL) and dried under vacuum at ambient temperature to give Example 66E (2.56 g, 77%). This product was used without further purification.

EXAMPLE 66F 1-(4-Cyclopropyl-5-fluoro-2,3-dihydro-1H-inden-1-yl)-3-(1H-indazol-4-yl)urea Example 66E (1.44 g, 4.33 mmol) was added to Example 66D (828 mg, 4.33 mmol) in diisopropylethylamine (0.75 mL, 4.33 mmol) and dimethylformamide (30 mL) at ambient temperature. After 1 hour the mixture was diluted with water (100 mL), the resulting white precipitate was filtered off, washed with water and air-dried. Suspended the wet cake in triethylamine (1.2 mL, 8.66 mmol), methanol (100 mL) and water (10 mL). Refluxed the mixture for 30 minutes, cooled to ambient temperature, diluted with water (300 mL), collected the precipitate by filtration, rinsed with water and allowed to dry. The resulting filter cake was further dried to constant weight, yielding 1.439 g (95% yield) of Example 66F as a white solid. $^1$H NMR (300 MHz, DMSO-$d_6$) δ ppm 0.78 (m, 2H), 0.93 (m, 2H), 1.78 (m, 1H), 1.87 (m, 1H), 2.47 (m, 1H), 2.87 (m, 1H), 3.05 (m, 1H), 5.14 (q, J=7.46 Hz, 1H), 6.69 (d, J=7.80 Hz, 1H), 6.96 (dd, J=11.36, 8.31 Hz, 1H), 7.06 (d, J=8.48 Hz, 1H), 7.16 (dd, J=8.13, 4.74 Hz, 1H), 7.21 (t, J=8.14 Hz, 1H), 7.67 (d, J=7.12 Hz, 1H), 8.04 (s, 1H), 8.59 (s, 1H), 12.99 (s, 1H). MS (ESI) m/z 351.09 (M+H)$^+$. Calcd for $C_{20}H_{19}FN_4O$: C, 68.56; H, 5.47; N, 15.99. Found: C, 68.43; H, 5.41; N, 15.34.

EXAMPLE 66G 3-(Dimethylamino)propyl 2,5-dioxopyrrolidin-1-yl carbonate

To a flask containing dichloromethane (200 mL) was added di-(N-succinimidyl) carbonate 5.50 g, 21.50 mmol) and 3-(dimethylamino)propan-1-ol (2.43 g, 23.60 mmol) and the mixture was stirred at room temperature for 12 hours. The mixture was concentrated in vacuo, purified on $SiO_2$ eluting with 1% $CH_3OH$ in $CH_2Cl_2$ to give Example 66G (3.7 g) in 70% yield. MS(+APCI)m/z 245 (M+H)$^+$.

EXAMPLE 66H 3-(Dimethylamino)propyl 4-(3-(4-cyclopropyl-5-fluoro-2,3-dihydro-1H-inden-1-yl)ureido)-1H-indazole-1-carboxylate trifluoroacetate To a solution of Example 66F (0.24 g, 0.70 mmol) and Example 66G (0.335 g, 1.40 mmol) in N,N-dimethylformamide (10 mL) was added a solution of 1N KO-t-Bu (0.8 mL, 0.80 mmol) and the mixture stirred 12 hours at ambient temperature. The resulting solution was concentrated and the residue was purified on reverse phase HPLC eluting with acetonitrile/0.1%TFA in $H_2O$ to give Example 66H (0.124 g) in 34%. $^1$H NMR (300 MHz, $CD_3OD$) δ ppm 0.80-0.84 (m, 2H), 0.92-0.97 (m, 2H), 1.60-1.82 (m, 1H), 1.86-212 (m, 2H), 2.28-2.38 (m, 1H), 2.60-2.72 (m, 1H), 2.97 (s, 6H), 3.40 (t, J=7.80, 15.26 Hz, 2H), 3.71 (t, J=6.44, 13.22 Hz, 1H), 4.21 (t, J=6.10, 11.87 Hz, 1H), 4.61 (t, J=5.77, 11.87 Hz, 2H), 5.27 (t, J=7.46, 14.58 Hz, 1H), 6.83-6.98 (m, 1H), 7.14-7.18 (m, 1H), 7.42-7.67 (m, 2H), 7.87-7.96 (m, 1H), 8.40 (d, J=1.02 Hz, 1H). MS(+APCI)m/z 480 (M+H)$^+$. Calc for $C_{26}H_{30}N_5O_3F$: 1.0TFA:C, 56.66; H, 5.26; N, 11.80. Found: C, 56.84; H, 5.43; N, 11.92.

EXAMPLE 67

1-(4-Cyclopropyl-2,3-dihydro-1H-inden-1-yl)-3-(1-(2-(dimethylamino)acetyl)-1H-indazol-4-yl)urea trifluoroacetate Example 67A 4-Bromo-2,3-dihydro-1H-inden-1-one O-methyl oxime Methoxylamine hydrochloride (5.7 g, 68.2 mmol) was added to 4-bromo-1-indanone (Aldrich, 13.477 g, 63.9 mmol) in pyridine (50 mL) and stirred for 3 hours at ambient temperature. Concentrated the mixture to a slurry, added ethyl acetate (200 mL), washed with 1N hydrochloric acid (200 mL), dried with brine, filtered through a silica gel plug, and concentrated the filtrate. Obtained 15.248 g (99% yield) of Example 67A. $^1$H NMR (300 MHz, DMSO-$d_6$) δ ppm 2.83 (m, 2H), 2.96 (m, 2H), 3.91 (s, 3H), 7.25 (t, J=7.80 Hz, 1H), 7.57 (dd, J=7.63, 0.84 Hz, 1H), 7.61 (dd, J=7.79, 1.01 Hz, 1H). MS (DCI) m/z 241.90 (M+H)$^+$.

EXAMPLE 67B

4-Cyclopropyl-2,3-dihydro-1H-inden-1-one O-methyl oxime

Example 67A (1.92 g, 8.0 mmol) was added to a mixture of cyclopropylboronic acid (Aldrich, 893 mg, 10.4 mmol), potassium phosphate (5.94 g, 28.0 mmol), palladium(II) acetate (90 mg, 0.4 mmol) and tricyclohexylphosphine (224 mg, 0.8 mmol) in toluene (32 mL) with water (1.6 mL). Heated the mixture at 100° C. for 3 hours on the microwave (Personal Chemistry). After cooling, the mixture was filtered through celite and rinsed with ethyl acetate. Concentrated the filtrate to an oil and chromatographed on silica gel with 0 to 10% ethyl acetate in hexane. Obtained 1.32 g (82% yield) of Example 67B. $^1$H NMR (300 MHz, DMSO-$d_6$) δ ppm 0.68 (m, 2H), 0.95 (m, 2H), 1.90 (m, 1H), 2.82 (m, 2H), 3.05 (m, 2H), 3.88 (s, 3H), 6.90 (d, J=7.46 Hz, 1H), 7.18 (t, J=7.63 Hz, 1H), 7.36 (d, J=7.80 Hz, 1H). MS (DCI) m/z 202.09 (M+H)$^+$.

EXAMPLE 67C

4-Cyclopropyl-2,3-dihydro-1H-inden-1-amine

Example 67B (1.32 g, 6.56 mmol), Raney nickel (6.0 g), and 20% ammonia in methanol (40 mL) were shaken under hydrogen (60 psi) for 4 hours at ambient temperature. The catalyst was removed by filtration and the solvent evaporated under reduced pressure, giving 1.11 g (97% yield) of Example 67C. $^1$H NMR (300 MHz, DMSO-$d_6$) δ ppm 0.61 (m, 2H), 0.90 (m, 2H), 1.58 (dq, J=12.29, 8.45 Hz, 1H), 1.85 (m, 3H), 2.35 (m, 1H), 2.70 (dt, J=16.05, 7.97 Hz, 1H), 2.97 (ddd, J=15.85, 8.73, 3.22 Hz, 1H), 4.17 (t, J=7.46 Hz, 1H), 6.66 (d, J=7.80 Hz, 1H), 7.09 (m, 2H). MS (DCI) m/z 174.12 (M+H)$^+$.

EXAMPLE 67D 1-(4-Cyclopropyl-2,3-dihydro-1H-inden-1-yl)-3-(1H-indazol-4-yl)urea

Example 66E (2.13 g, 6.41 mmol) was added to Example 67C (1.11 g, 6.41 mmol) in diisopropylethylamine (1.12 mL, 6.41 mmol) and dimethylformamide (50 mL) at ambient temperature. After 1 hour the mixture was diluted with water (200 mL), the resulting white precipitate was filtered off, washed with water and air dried. Obtained 2.44 g (98% yield) of methyl 4-(3-(4-cyclopropyl-2,3-dihydro-1H-inden-1-yl)ureido)-1H-indazole-1-carboxylate as a white solid. Suspended 1.94 g of this intermediate in triethylamine (1.4 mL, 10.0 mmol), methanol (150 mL) and water (15 mL). Refluxed the mixture for 30 minutes, cooled to ambient temperature, diluted with water (500 mL), collected the white precipitate by filtration, rinsed with water and air-dried. The wet cake was freeze-dried to constant weight, yielding 1.60 g (97% yield) of Example 67D. 1H NMR (300 MHz, DMSO-$d_6$) δ ppm 0.66 (m, 2H), 0.94 (m, 2H), 1.84 (m, 1H), 1.91 (m, 1H), 2.48 (m, 1H), 2.87 (dt, J=15.94, 7.97 Hz, 1H), 3.07 (ddd, J=15.94, 8.81, 4.07 Hz, 1H), 5.20 (q, J=7.46 Hz, 1H), 6.70 (d, J=7.80 Hz, 1H), 6.78 (m, 1H), 7.06 (d, J=8.14 Hz, 1H), 7.13 (d, J=4.41 Hz, 2H), 7.22 (t, J=7.97 Hz, 1H), 7.68 (d, J=7.12 Hz, 1H), 8.04 (s, 1H), 8.58 (s, 1H), 12.99 (s, 1H). MS (ESI) m/z 333.08 (M+H)$^+$. Calcd for $C_{20}H_{20}N_4O$. 0.23 $H_2O$: C, 71.38; H, 6.13; N, 16.65. Found: C, 71.40; H, 5.95; N, 16.42.

EXAMPLE 67E 1-(4-Cyclopropyl-2,3-dihydro-1H-inden-1-yl)-3-(1-(2-(dimethylamino)acetyl)-1H-indazol-4-yl)urea trifluoroacetate The title compound was prepared as described in Example 68E substituting Example 67D (0.18 g, 0.50 mmol) for Example 68D and HPLC purification (acetonitrile/0.1%TFA in $H_2O$) instead of HCl treatment. The material was recrystallized from THF (10 mL) to give 0.056 g (25% yield). $^1$H NMR (300 MHz, $CD_3OD$) δ ppm 0.63-0.67 (m, 2H), 0.90-0.96 (m, 2H), 1.83-1.93 (m, 2H), 2.53-2.64 (m, 1H), 2.79-2.89 (m, 1H), 2.96-3.05 (m, 1H), 3.31 (s, 6H), 5.06 (s, 2H), 5.27-5.28 (m, 1H), 6.96-7.01 (m, 2H), 7.24 (d, J=7.67 Hz, 1H), 7.39 (t, J=8.28, 15.96 Hz, 1H), 7.57 (d, J=7.98 Hz, 1H), 7.75 (d, J=7.98 Hz, 1H), 8.53 (s, 1H). MS(+APCI)m/z 418 (M+H)$^+$. Calc for $C_{24}H_{27}N_5O_2$: 1.0TFA:C, 58.75; H, 5.31; N,13.18. Found: C, 58.92; H, 5.18; N, 13.26.

EXAMPLE 68

1-(5-Cyclopropyl-2,3-dihydro-1H-inden-1-yl)-3-(1-(2-(dimethylamino)acetyl)-1H-indazol-4-yl)urea hydrochloride

EXAMPLE 68A

5-Bromo-2,3-dihydro-1H-inden-1-one O-methyl oxime

Methoxylamine hydrochloride (6.75 g, 80.9 mmol) was added to 5-bromo-1-indanone (Aldrich, 15.517 g, 73.5 mmol) in pyridine (75 mL) and stirred overnight at ambient temperature. Concentrated the mixture to a slurry, added ethyl acetate (200 mL), washed with 1N hydrochloric acid (200 mL), dried with brine, filtered through a silica gel plug, and concentrated the filtrate. Obtained 17.56 g (99% yield) of Example 68A as a beige solid. $^1$H NMR (300 MHz, DMSO-$d_6$) δ ppm 2.80 (m, 2H), 3.01 (m, 2H), 3.89 (s, 3H), 7.47 (m, 2H), 7.63 (m, 1H). MS (DCI) m/z 239.96 (M+H)$^+$.

EXAMPLE 68B

5-Cyclopropyl-2,3-dihydro-1H-inden-1-one O-methyl oxime

Example 68A (960 mg, 4.0 mmol) was added to a mixture of cyclopropylboronic acid (Aldrich, 447 mg, 5.2 mmol), potassium phosphate (2.97 g, 14.0 mmol), palladium(II) acetate (45 mg, 0.2 mmol) and tricyclohexylphosphine (112 mg, 0.4 mmol) in toluene (16 mL) with water (0.8 mL). Heated the mixture at 100° C. for 3 hours on the microwave (Personal Chemistry). After cooling, the mixture was filtered through celite and rinsed with ethyl acetate. Concentrated the filtrate to an oil and chromatographed on silica gel with 0-to-10% ethyl acetate in hexane. Obtained 657 mg (82% yield) of Example 68B. $^1$H NMR (300 MHz, DMSO-$d_6$) δ ppm 0.70 (m, 2H), 0.97 (m, 2H), 1.94 (m, 1H), 2.77 (m, 2H), 2.94 (m, 2H), 3.86 (s, 3H), 6.99 (d, J=8.14 Hz, 1H), 7.06 (s, 1H), 7.42 (d, J=7.80 Hz, 1H). MS (DCI) m/z 202.06 (M+H)$^+$.

EXAMPLE 68C

5-Cyclopropyl-2,3-dihydro-1H-inden-1-amine

Example 68B (629 mg, 3.13 mmol), Raney nickel (3.0 g), and 20% ammonia in methanol (40 mL) were shaken under hydrogen (60 psi) for 6 hours at ambient temperature. The catalyst was removed by filtration and the solvent evaporated under reduced pressure, giving 509 mg (94% yield) of Example 68C. $^1$H NMR (300 MHz, DMSO-$d_6$) δ ppm 0.60 (m, 2H), 0.88 (m, 2H), 1.54 (dq, J=12.21, 8.59 Hz, 1H), 1.87 (m, 3H), 2.30 (m, 1H), 2.63 (m, 2H), 2.78 (ddd, J=15.77, 8.65, 3.05 Hz, 1H), 4.12 (t, J=7.46 Hz, 1H), 6.87 (m, 2H), 7.18 (d, J=7.46 Hz, 1H). MS (DCI) m/z 157.07 (M+H−$NH_3$)$^+$.

EXAMPLE 68D 1-(5-Cyclopropyl-2,3-dihydro-1H-inden-1-yl)-3-(1H-indazol-4-yl)urea Example 66E (977 mg, 2.94 mmol) was added to Example 68C (509 mg, 2.94 mmol) in diisopropylethylamine (0.51 mL, 2.94 mmol) and dimethylformamide (30 mL) at ambient temperature. After 1 hour the mixture was diluted with water (100 mL), the resulting white precipitate was filtered off, washed with water and air dried. Suspended the wet cake in triethylamine (0.82 mL, 5.88 mmol), methanol (75 mL) and water (5 mL). Refluxed the mixture for 30 minutes, cooled to ambient temperature, diluted with water (250 mL), collected the white precipitate by filtration, rinsed with water and allowed to dry. The resulting filter cake was further dried to constant weight, yielding 924 mg (95% yield) of Example 68D. $^1$H NMR (300 MHz, DMSO-$d_6$) δ ppm 0.65 (m, 2H), 0.92 (m, 2H), 1.78 (m, 1H), 1.91 (m, 1H), 2.44 (m, 1H), 2.78 (m, 1H), 2.91 (m, 1H), 5.14 (q, J=7.46 Hz, 1H), 6.69 (d, J=7.80 Hz, 1H), 6.97 (m, 2H), 7.06 (d, J=8.14 Hz, 1H), 7.21 (m, 2H), 7.68 (d, J=7.46 Hz, 1H), 8.05 (s, 1H), 8.60 (s, 1H), 12.99 (s, 1H). MS (ESI) m/z 333.04 (M+H)$^+$. Calcd for $C_{20}H_{20}N_4O \cdot 0.3\,H_2O$: C, 71.11; H, 6.15; N, 16.59. Found: C, 71.13; H, 6.04; N, 16.38.

EXAMPLE 68E 1-(5-Cyclopropyl-2,3-dihydro-1H-inden-1-yl)-3-(1-(2-(dimethylamino)acetyl)-1H-indazol-4-yl)urea hydrochloride To a round bottom flask containing 40 mL of $CH_2Cl_2$/DMF (10/1) was added Example 68D (0.30 g, 1.10 mmol), 1-hydroxybenzotriazole hydrate (0.18 g, 1.30 mmol), 1-(3-dimethylaminopropyl)-3-ethylcarbodiimide hydrochloride (0.256 g, 1.30 mmol), N,N-dimethylglycine (0.138 g, 1.30 mmol), and the mixture was stirred at room temperature for 24 hours. The mixture was diluted with $CH_2Cl_2$ (100 mL), washed with sat $NaHCO_3$, dried ($Na_2SO_4$) and concentrated in vacuo. The material was purified on $SiO_2$ eluting with ethyl acetate. The material was taken up in ethyl acetate/diethyl ether (22 mL, 1/10) and 2M HCl in diethyl ether (2.0 eq) was added and the solution stirred at room temperature for 5 minutes. The material was concentrated in vacuo to give Example 68E as a white solid (0.192 g) in 42%. $^1$H NMR (300 MHz, $CD_3OD$) δ ppm 0.62-0.66 (m, 2H), 0.91-0.96 (m, 2H), 1.84-1.93 (m, 2H), 2.54-2.62 (m, 1H), 2.79-2.87 (m, 1H), 2.94-3.01 (m, 1H), 3.11 (s, 6H), 5.02 (s, 2H), 5.25-5.29 (m, 1H), 6.93-6.96 (m, 2H), 7.23 (d, J=7.67Hz, 1H), 7.37 (t, J=8.28, 15.96 Hz, 1H), 7.56 (d, J=7.98 Hz, 1H), 7.74 (d, J=7.98 Hz, 1H), 8.49 (s, 1H). MS(+APCI)m/z 418 (M+H)+. Calc for $C_{24}H_{27}N_5O_2$: 1.4 HCl: C, 61.52; H, 6.11; N, 14.95. Found: C, 61.87; H, 6.15; N, 14.82.

EXAMPLE 69

1-(1-(2-(Dimethylamino)acetyl)-1H-indazol-4-yl)-3-(4-(3,3-dimethylbutyl)-5-fluoro-2,3-dihydro-1H-inden-1-yl)urea

EXAMPLE 69A 4-(3,3-Dimethylbut-1-ynyl)-5-fluoro-2,3-dihydro-1H-inden-1-one O-methyl oxime Example 66B (1.29 g, 5.0 mmol) was added to a mixture of 3,3-dimethyl-1-butyne (Aldrich, 0.75 mL, 6.0 mmol), $Pd(Ph_3P)_2Cl_2$ (175 mg, 0.25 mmol), copper(I) iodide (48 mg, 0.25 mmol) and triphenylphosphine (262 mg, 1.0 mmol) in triethylamine (7.5 mL) and dimethylformamide (2.5 mL). The mixture was heated to 130 ° C. for 20 minutes on the microwave (Personal Chemistry). Additional 3,3-dimethyl-1-butyne (1.5 mL, 12.0 mmol) was added via syringe, then continued heating for another 20 minutes. After cooling, the mixture was filtered through celite, rinsed with ethyl acetate, and the filtrate concentrated to an oil. The material was chromatographed on silica gel with 0 to 10% ethyl acetate in hexane, yielding 1.32 g of impure product. Repeated chromatography on silica gel with 0 to 100% dichloromethane in hexane, to give 1.089 g (84% yield) of Example 69A. $^1$H NMR (300 MHz, DMSO-$d_6$) δ ppm 1.31 (s, 9H), 2.84 (m, 2H), 2.99 (m, 2H), 3.89 (s, 3H), 7.17 (dd, J=9.67, 8.65 Hz, 1H), 7.51 (dd, J=8.48, 5.09 Hz, 1H). MS (DCI) m/z 260.06 (M+H)$^+$.

EXAMPLE 69B 4-(3,3-Dimethylbutyl)-5-fluoro-2,3-dihydro-1H-inden-1-amine

Example 69A (1.065 g, 4.11 mmol), Raney nickel (10 g), and 20% ammonia in methanol (90 mL) were shaken under hydrogen (60 psi) for 16 hours at ambient temperature. The catalyst was removed by filtration and the solvent evaporated under reduced pressure, giving 843 mg (88% yield) of (Z)-4-(3,3-dimethylbut-1-enyl)-5-fluoro-2,3-dihydro-1H-inden-1-amine as a green oil. This intermediate (700 mg, 3.0 mmol), Raney nickel (7.17 g), and methanol (20 mL) were shaken under hydrogen (60 psi) for 16 hours at 40° C. The mixture was filtered and retreated with catalyst (7.01 g) for 2 hours at 40° C., then 14 hours at ambient temperature. The mixture was filtered through a nylon membrane and the filtrate was concentrated to yield 389 mg (55% yield) of Example 69B. $^1$H NMR (300 MHz, DMSO-$d_6$) δ ppm 0.94 (s, 9H), 1.31 (m, 2H), 1.60 (m, 1H), 1.87 (br s, 2H), 2.34 (m, 1H), 2.63 (m, 1H), 2.84 (ddd, J=15.85, 8.73, 3.22 Hz, 1H), 4.14 (t, J=7.80 Hz, 1H), 6.91 (dd, J=10.51, 8.14 Hz, 1H), 7.14 (dd, J=7.97, 4.92 Hz, 1H). MS (DCI) m/z 236.1 (M+H)$^+$.

EXAMPLE 69C 1-(4-(3,3-Dimethylbutyl)-5-fluoro-2,3-dihydro-1H-inden-1-yl)-3-(1H-indazol-4-yl) urea Example 66E (549 mg, 1.65 mmol) was added to Example 69B (389 mg, 1.65 mmol) along with diisopropylethylamine (0.29 mL, 1.65 mmol) in dimethylformamide (20 mL) at ambient temperature. After I hour, the mixture was partitioned between ethyl acetate (200 mL) and water (200 mL), and the organic layer was dried with brine and sodium sulfate, and then evaporated under reduced pressure. The residue was chromatographed on silica gel with 10% methanol in ethyl acetate to obtain methyl 4-(3-(4-(3,3-dimethylbutyl)-5-fluoro-2,3-dihydro-1H-inden-1-yl)ureido)-1H-indazole-1-carboxylate as a tan solid. This intermediate was dissolved in triethylamine (0.46 mL, 3.31 mmol), methanol (50 mL) and water (5 mL). The mixture was refluxed for 1 hour, concentrated under reduced pressure and chromatographed on silica gel with 0 to 10% methanol in dichloromethane to give 413 mg (63% yield) of Example 69C as a solid. $^1$H NMR (300 MHz, DMSO-$d_6$) δ ppm 0.97 (s, 9H), 1.35 (m, 2H), 1.87 (m, 1H), 2.55 (m, 2H), 2.80 (dt, J=15.60, 7.80 Hz, 1H), 2.96 (ddd, J=16.28, 8.47, 4.41 Hz, 1H), 5.17 (q, J=7.12 Hz, 1H), 6.70 (d, J=7.80 Hz, 1H), 6.99 (dd, J=10.18, 8.47 Hz, 1H), 7.07 (d, J=8.47 Hz, 1H), 7.18 (m, 1H), 7.21 (t, J=8.14 Hz, 1H), 7.67 (d, J=7.45 Hz, 1H), 8.04 (s, 1H), 8.59 (s, 1H), 12.99 (s, 1H). MS (ESI) m/z 395.23 (M+H)$^+$. Calcd for $C_{23}H_{27}FN_4O \cdot 0.25 H_2O \cdot 0.20$ Methanol: C, 68.74; H, 7.04; N, 13.82. Found: C, 68.72; H, 7.09; N, 13.84.

EXAMPLE 69D 1-(1-(2-(Dimethylamino)acetyl)-1H-indazol-4-yl)-3-(4-(3,3-dimethylbutyl)-5-fluoro-2,3-dihydro-1H-inden-1-yl)urea hydrochloride The title compound was prepared as described in Example 68E substituting Example 69C (0.150 g, 0.40 mmol) for Example 68D. The mixture was purified on $SiO_2$ with ethyl acetate/methylene chloride (1/1) to give a white solid. The material was taken up in ethyl acetate/diethyl ether (22 mL, 1/10) and 2M HCl in diethyl ether (2.0 eq) was added and stirred at room temperature for 5 minutes. The material was concentrated in vacuo to give Example 69D (0.062g) in 30% yield. $^1$H NMR (300 MHz, $CD_3OD$) δ ppm 1.0 (s, 9H), 1.35-1.43 (m, 2H), 1.91-2.01 (m, 1H), 2.59-2.69 (m, 2H), 2.81-2.89 (m, 1H), 2.97-3.07 (m, 2H), 3.10 (s, 6H), 5.02 (s, 2H), 5.27-5.32 (m, 1H), 6.88-6.97 (m, 1H), 7.15-7.20 (m, 1H), 7.58 (t, J=8.13, 15.93 Hz, 1H), 7.72 (d, J=7.8 Hz, 1H), 8.02 (d, J=8.14 Hz, 1H), 8.47 (d, J=1.02 Hz, 1H). MS(+APCI) m/z 480 (M+H)$^+$. Calc for $C_{27}H_{34}N_5O_2F$: 1.1 HCl: 1.0 $H_2O$: C, 60.31; H, 6.95; N, 13.02. Found: C, 60.57; H, 7.32; N, 12.83.

EXAMPLE 70

1-(4-cyclopropyl-5-fluoro-2,3-dihydro-1H-inden-1-yl)-3-(1-(2-(dimethylamino)acetyl)-1H-indazol-4-yl) urea hydrochloride The title compound was prepared as described in Example 68E, substituting Example 66F (0.250 g, 0.70 mmol) for Example 68D. The mixture was purified on $SiO_2$ with 1% methanol in ethyl acetate to give a solid. The material was taken up in ethyl acetate/diethyl ether (44 mL, 1/10) and 2M HCl in diethyl ether (2.0 eq) was added and stirred at room temperature for 5 minutes. The material was concentrated in vacuo to give Example 70 (0.180g) in 54%. $^1$H NMR (300 MHz, $CD_3OD$) δ ppm 0.80-0.84 (m, 2H), 0.92-0.97 (m, 2H), 1.74-1.79 (m, 1H), 1.87-2.00 (m, 1H), 2.57-2.68 (m, 1H), 2.87-2.98 (m, 1H), 3.10-3.20 (m, 7H), 5.02 (s, 2H), 5.25-5.30 (m, 1H), 6.83-6.90 (m, 1H), 7.14-7.18 (m, 1H), 7.58 (t, J=8.14, 15.93Hz, 1H), 7.71 (d, J=8.14Hz, 1H), 8.03 (d, J=7.46Hz, 1H), 8.46 (d, J=0.68Hz, 1H). MS(+APCI)m/z 436 (M+H)$^+$. Calc for $C_{24}H_{22}N_5O_2F$: 1.2HCl: C, 60.15; H, 5.72; N, 14.61. Found: C, 60.07; H, 5.76; N, 14.28.

EXAMPLE 75

(R)-1-(5-tert-butyl-2,3-dihydro-1H-inden-1-yl)-3-(1-(2-(methylamino)acetyl)-1H-indazol-4-yl)urea hydrochloride

EXAMPLE 75A (R)-benzyl 2-(4-(3-(5-tert-butyl-2,3-dihydro-1H-inden-1-yl)ureido)-1H-indazol-1-yl)-2-oxoethyl(methyl)carbamate The title compound was prepared as described in Example 68E substituting Example 56J for Example 68D and 2-((benzyloxycarbonyl)(methyl)amino)acetic acid for N,N-dimethylglycine. The mixture was purified on $SiO_2$ eluting with 5% $CH_3OH$ in $CH_2Cl_2$ to give Example 75A. $^1$H NMR (300 MHz, $CD_3OD$) δ ppm 1.32 (s, 9H), 1.83-1.95 (m, 1H), 2.55-2.65 (m, 1H), 2.81-2.89 (m, 1H), 2.92-3.06 (m, 1H), 4.76 (s, 2H), 4.84 (s, 3H), 5.15 (s, 2H), 5.29 (t, J=7.46, 14.58 Hz, 1H), 7.24-7.42 (m, 8H), 7.51 (t, J=7.80, 15.94 Hz, 1H), 7.75 (d, J=7.80 Hz, 1H), 8.01 (d, J=7.84 Hz, 1H), 8.34 (s, 1H). MS(+APCI )m/z 554 (M+H)$^+$.

EXAMPLE 75B (R)-1-(5-tert-butyl-2,3-dihydro-1H-inden-1-yl)-3-(1-(2-(methylamino)acetyl)-1H-indazol-4-yl)urea hydrochloride To a Parr flask containing methanol (100 mL) was added Example 75A (0.85 g, 1.50 mmol), 10% Pd/C (0.20 g) and saturated HCl in methanol (1.1eq). A hydrogen atmosphere (60 psi) was applied to the mixture and the vessel was shaken at room temperature for 1 hour. The mixture was filtered, washed with methanol (50 mL) and concentrated in vacuo to give Example 75B as a white solid (0.46 g) in 73% yield. $^1$H NMR (300 MHz, $CD_3OD$) δ ppm 1.31 (s, 9H), 1.82-1.98 (m, 1H), 2.54-2.72 (m, 1H), 2.80-2.88 (m, 1H), 2.91-3.07 (m, 1H), 3.83 (s, 3H), 3.91 (s, 2H), 5.25-5.33 (m, 1H), 7.17 (d, J=7.46Hz, 1H), 7.24-7.34 (m, 4H), 7.59 (d, J=7.46 Hz, 1H), 8.01 (s, J=0.68 Hz, 1H). MS(+APCI)m/z 420 (M+H)$^+$. Calc for $C_{24}H_{29}N_5O_2$: 1.1HCl: 0.40$H_2O$: C, 61.75; H, 6.67; N, 15.00. Found: C, 62.12; H, 7.07; N, 14.75.

EXAMPLE 76

1-( 1-(2-(Dimethylamino)acetyl)-1H-indazol-4-yl)-3-(7-(trifluoromethyl)chroman-4-yl)urea

EXAMPLE 76A 3-(3-Trifluoromethyl-phenoxy)propanoic acid

Sodium hydroxide (4.24 g, 106 mmol) was dissolved in water (50 ml). 3-Trifluoromethyl-phenol (5.19 g, 32 mmol) was dissolved in 25 ml of the sodium hydroxide solution and heated to reflux. 3-Bromopropionic acid (9.79g, 64 mmol) in the other 25 ml of sodium hydroxide solution was added dropwise over 15 minutes. The reflux was continued for 45 minutes more, with portions of 10M sodium hydroxide solution added to maintain the pH of the solution at appoximately pH 10. The reaction mixture was then cooled, acidified with hydrochloric acid, and extracted with ethyl acetate. The combined organic layers were extracted with saturated aqueous sodium bicarbonate, and the aqueous layers acidified with hydrochloric acid. The acidified aqueous layers were extracted with diethyl ether. The ether layers were dried with magnesium sulfate, and the solvent removed under vacuum to give 2.5 g of the crude product which was used directly in the next step.

$^1$H NMR (300 MHz, $d_6$-DMSO) δ 12.40 (broad s, 1H), 7.51 (t, J 7.5 Hz, 1H), 7.24 (m, 3H), 4.23 (t, J 6.0 Hz, 2H), 2.71 (t, J 6.0 Hz, 2H).

EXAMPLE 76B

7-Trifluoromethyl-chroman-4-one

Polyphosphoric acid (10 mL) was heated in water bath and Example 76A (~2.5 g) was added. After stirring for 30 minutes this mixture was poured onto ice and extracted twice with diethyl ether. The combined organic layers were washed with water, aqueous NaHCO$_3$, and water and concentrated. The residue was chromatographed on silica gel, and eluted with 9:1 ethyl acetate: hexanes to afford the title compound (0.84 g, 12% for 2 steps) as a solid. $^1$H NMR (300 MHz, DMSO-d$_6$) δ 7.96 (d, J 7.5 Hz, 1H), 7.40 (m, 2H), 4.62 (t, J 6.0 Hz, 2H), 2.88 (t, J 6.0 Hz, 2H). MS (DCI/NH$_3$) m/e 234 (M+NH$_4$)$^+$.

EXAMPLE 76C

7-Trifluoromethyl-chroman-4-one O-methyl-oxime

A solution of Example 76B (0.84 g, 3.88 mmol) and methoxyl amine hydrochloride (0.65 g, 7.78 mmol, 2eq.) in pyridine (10 mL) was stirred for 18 hours at ambient temperature and concentrated under reduced pressure. The residue was dissolved in diethyl ether and washed sequentially with water, 1N HCl and water. The isolated organic layer was concentrated and the residue chromatographed on silica gel, eluting with 5:95 ethyl acetate: hexanes to afford the title product (0.71 g, 74%). $^1$H NMR (300 MHz, DMSO-d$_6$) δ 8.60 (d, J 7.5 Hz, 1H, major), 8.00 (d, J 7.5 Hz, 1H, minor), 7.28 (m, 2H), 4.40 (t, J 6.0 Hz, 2H, major), 4.24 (t, J 6.0 Hz, 2H, minor), 3.98 (s, 3H, minor), 3.96 (s, 3H, major), 2.87(t, J 6.0 Hz, 2H, minor), 2.70 (t, J 6.0 Hz, 2H, major). MS (DCI/NH$_3$) m/e 246 (M+H)$^+$.

EXAMPLE 76D

7-Trifluoromethyl-chroman-4-ylamine

The title compound was prepared as described in Example 66D, substituting Example 76C for Example 66C. $^1$H NMR (300 MHz, CDCl$_3$) δ 7.43(d, 1H, J=8.1 Hz), 7.14(d, 1H, J=8.1 Hz ), 7.06(s, 1H), 4.22-4.37 (m, 2H), 4.08 (t, 1H, J=5.4 Hz), 2.12-2.22 (m, 1H), 1.82-1.92 (m, 1H). MS (DCI) m/e 218 (M+H)$^+$.

EXAMPLE 76E

4-[3-(7-Trifluoromethyl-chroman-4-yl)-ureido]-indazole-1carboxylic acid methyl ester The title compound was prepared as described in Example 65C, substituting Example 76D for Example 65B. $^1$H NMR (300 MHz, DMSO-d$_6$) δ 8.92 (s, 1H), 8.40 (s, 1H), 7.85 (d, 1H, J=7.1 Hz), 7.71 (d, 1H, J=8.5 Hz), 7.54 (m, 2H), 7.26 (d, 1H, J=7.8 Hz), 7.14 (s, 1H), 6.95 (d, 1H, J=8.1 Hz), 5.03 (m, 1H), 4.38 (m, 1H), 4.27 (m, 1H), 4.03 (s, 3H), 2.19 (m, 1H), 2.09 (m, 1H). MS (ESI) m/e 435 (M+H)$^+$.

EXAMPLE 76F

N-1H-indazol-4-yl-N'-[7-(trifluoromethyl)-3,4-dihydro-2H-chromen-4-yl]urea

The title compound was prepared as described in Example 65D, substituting Example 76E for Example 65C. $^1$H NMR (300 MHz, DMSO-d$_6$) δ 13.00 (broad s, 1H), 8.67 (s, 1H), 8.04 (s, 1H), 7.67 (d, J=7.5 Hz, 1H), 7.55 (d, J=7.5 Hz, 1H), 7.22 (m, 2H), 7.10 (m, 2H), 7.00 (d, J=7.5 Hz, 1H), 5.00 (m, 1H), 4.41-4.20 (m, 2H), 2.22-2.00 (m, 2H). S (ESI) m/e 377 (M+H)$^+$. Calcd. For C$_{18}$H$_{15}$N$_4$O$_2$F$_3$. 0.7 H$_2$O: C, 55.59; H, 4.25; N, 14.40. Found: C, 55.51; H, 3.98; N, 14.65.

EXAMPLE 76G 1-(1-(2-(Dimethylamino)acetyl)-1H-indazol-4-yl)-3-(7-(trifluoromethyl)chroman-4-yl)urea The title compound was prepared as described in Example 68E, substituting Example 76F for Example 68D. The mixture was purified on SiO$_2$ eluting with 3% CH$_3$OH in CH$_2$Cl$_2$ to give the title compound as a solid (0.62g) in 46% yield. $^1$H NMR (300 MHz, CD$_3$OD) δ ppm 2.10-2.34 (m, 1H), 2.23-2.34 (m, 1H), 3.11 (s, 6H), 4.32-4.42 (m, 2H), 5.03 (s, 2H), 5.12 (t, J=5.77, 11.87 Hz, 1H), 7.08-7.10 (m, 1H), 7.17-7.20 (m, 1H), 7.52-7.63 (m, 2H)', 7.72-7.75 (m, 1H), 7.98-8.05 (m, 1H), 8.50 (d, J=1.01 Hz, 1H). MS(+APCI)m/z 462 (M+H)$^+$. Calc for C$_{22}$H$_{22}$N$_5$O$_3$F$_3$: 1.1HCl: C, 52.69; H, 4.64; N, 13.96. Found: C, 52.64; H, 4.88; N, 13.76.

EXAMPLE 77

1-(8-Tert-butylchroman-4-yl)-3-(1-(2-(dimethylamino)acetyl)-1H-indazol -4-yl)urea hydrochloride

EXAMPLE 77A

1-Tert-butyl-2-(prop-2-ynyloxy)benzene

2-Tert-butylphenol (15.02 g, 15.4 ml, 100 mmol), propargyl bromide (14.3 ml of 80% in toluene, 128 mmol), and potassium carbonate (17.66 g, 128 mmol) were stirred together in 200 ml of acetonitrile at ambient temperature for 5 days. The solvent was removed under reduced pressure, and the residue taken into water and extracted with diethyl ether. The organic layers were combined, dried with magnesium sulfate, and filtered. The solvent was evaporated under reduced pressure to give 18.86 g of the title compound which was used without further purification. $^1$H NMR (300 MHz, CDCl$_3$) δ ppm 7.30 (dd, J=7.80, 1.70 Hz, 1 H), 7.15-7.22 (m, 1 H), 6.90-6.98 (m, 2 H), 4.73 (d, J=2.37 Hz, 2 H), 2.48 (t, J=2.37 Hz, 1 H), 1.39 (s, 9 H). MS (DCI) m/e 206 (M+NH$_4$)$^+$.

EXAMPLE 77B

1Tert-butyl-2-(3-chloroprop-2-ynyloxy)benzene

Example 77A (18.86 g, 100 mmol) was dissolved in 400 ml acetone. N-chlorosuccinimide (16.02 g, 120 mmol) and silver acetate (1.67 g, 10 mmol) were added, and the mixture heated to reflux for 4 hours. After cooling, the silver salts were removed by filtration and the filtrate evaporated under reduced pressure. The residue was taken up in diethyl ether, washed with water and saturated aqueous sodium bicarbonate, dried with magnesium sulfate, and filtered. The solvent removed under reduced pressure to give 26.13 g of Example 77B which was used without further purification. $^1$H NMR (300 MHz, CDCl$_3$) δ ppm 7.30 (dd, J=7.97, 1.53 Hz, 1 H), 7.19 (td, J=7.71, 1.86 Hz, 1 H), 6.91-6.97 (m, 2 H), 4.73 (s, 2 H), 1.38 (s, 9 H). MS (DCl) m/e 223 (M+H)$^+$

EXAMPLE 77C

8-Tert-butylchroman-4-one

Example 77B (25.8 g) in 250 ml ethylene glycol was heated to reflux for 4 hours. The mixture was cooled, poured into water, and extracted with diethyl ether. The organic layers were combined, washed with IN sodium hydroxide and saturated ammonium carbonate sequentially, dried with magnesium sulfate, and filtered. Removal of solvent under reduced pressure gave a residue. The residues were filtered through a pad of silica gel with 1:1 methylene chloride:hexanes, and the filtrate evaporated under reduced pressure to give 13.51 g of Example 77C. $^1$H NMR (300 MHz, CDCl$_3$) δ ppm 7.81 (dd, J=7.80, 1.70 Hz, 1 H), 7.47 (dd, J=7.63, 1.86 Hz, 1 H), 6.95 (t, J=7.80 Hz, 1 H), 4.51-4.58 (m, 2 H), 2.79-2.85 (m, 2 H), 1.39 (s, 9 H). MS (DCI) m/e 205 (M+H)$^+$

EXAMPLE 77D

8-Tert-butylchroman-4-one O-methyl oxime

Example 77C (13.51 g, 66 mmol) was dissolved in 100 ml pyridine. Methoxylamine hydrochloride (10 g, 120 mmol) was added and the mixture stirred at ambient temperature for 16 hours. The pyridine was removed under reduced pressure, and the residue partitioned between water and diethyl ether. The mixture was extracted with diethyl ether, and the combined organic layers washed with 1N sodium hydroxide and 1N hydrochloric acid sequentially, dried with magnesium sulfate, and filtered. The solvent was removed under reduced pressure to give 14.44 g of Example 77D which was used without further purification. $^1$H NMR (300 MHz, CDCl$_3$) δ ppm 7.79 (dd, J=7.80, 1.70 Hz, 1 H), 7.21-7.27 (m, 1 H), 6.87 (t, J=7.80 Hz, 1 H), 4.18 (t, J=6.27 Hz, 2 H), 3.98 (s, 3 H), 2.91 (t, J=6.27 Hz, 2 H), 1.36 (s, 9 H). MS (DCI) m/e 234 (M+H)$^+$.

EXAMPLE 77E

8-Tert-butylchroman-4-amine

Example 77D (14.44 g, 61.9 mmol), 1.5 g of 10% palladium on carbon, and 400 ml of 20% ammonia in methanol were shaken under hydrogen at 60 psi and ambient temperature for 2.5 hours. The catalyst was removed by filtration and the solvent evaporated under reduced pressure, giving 13.50 g of Example 77E which was used without further purification. $^1$H NMR (300 MHz, CDCl$_3$) δ ppm 7.14-7.24 (m, 3 H) 6.81-6.89 (m, 1 H) 4.22-4.29 (m, 2 H) 4.11 (t, J=5.09 Hz, 1 H) 2.10-2.25 (m, 1 H) 1.90 (td, J=9.16, 4.07 Hz, 1 H) 1.34-1.37 (m, 9 H). MS (DCI) m/e 206 (M+H)$^+$.

EXAMPLE 77F

Methyl 4-({[(8-tert-butyl-3,4-dihydro-2H-chromen-4-yl)amino]carbonyl} amino)-1H-indazole-1-carboxylate Example 77E (12.32 g, 60 mmol), Example 66E (19.94 g, 60 mmol), and diisopropylethylamine (11.63 g, 16 ml, 90 mmol) were dissolved in 100 ml of N,N-dimethylformamide. The mixture was stirred at ambient temperature for 16 hours, and diluted with water. The precipitate that formed was collected by filtration, air-dried, and then suspended in diethyl ether and hexane and filtered with a mixture of diethyl ether and hexanes to give 20.6 g of the titled compound. $^1$H NMR (300 MHz, DMSO-d$_6$) δ ppm 8.77 (s, 1 H), 8.35 (s, 1 H), 7.89 (d, J=7.46 Hz, 1 H), 7.69 (d, J=8.48 Hz, 1 H), 7.46-7.55 (m, 1 H), 7.16 (dd, J=8.14, 2.37 Hz, 2 H), 6.83-6.93 (m, 2 H), 4.86-4.92 (m, 1 H), 4.32-4.40 (m, 1 H), 4.09-4.20 (m, 1 H), 4.03 (s, 3 H), 2.09 (ddd, J=17.88, 8.90, 4.75 Hz, 2 H), 1.34 (s, 9 H). MS (ESI) m/e 423 (M+H)$^+$.

EXAMPLE 77G

N-(8-Tert-butyl-3,4-dihydro-2H-chromen-4-yl)-N'-1H-indazol-4-ylurea

Example 77F (20.6 g, 48 mmol) was dissolved in a mixture of 100 ml tetrahydrofuran and 75 ml methanol. Sodium hydroxide (5M in methanol, 50 ml, 250 mmol) was added, and the mixture stirred at ambient temperature for 30 minutes. The mixture was diluted with water, and the precipitate that formed was collected by filtration, giving 15.70 g of the titled compound. $^1$H NMR (300 MHz, DMSO-d$_6$) δ ppm 13.00 (s, 1 H), 8.51 (s, 1 H), 8.01 (s, 1 H), 7.69 (d, J=7.46 Hz, 1 H), 7.13-7.25 (m, 3 H), 7.06 (d, J=8.14 Hz, 1 H), 6.83-6.94 (m, 2 H), 4.84-4.91 (m, 1 H), 4.37 (dt, J=10.85, 4.24 Hz, 1 H), 4.06-4.19 (m, 1 H), 1.99-2.14 (m, 2H), 1.35 (s, 9 H). MS (ESI) m/e 365 (M+H)$^+$.

EXAMPLE 77H 1-(8-Tert-butylchroman-4-yl)-3-(1-(2-(dimethylamino)acetyl)-1 H-indazol-4-yl)urea hydrochloride The title compound was prepared as described in Example 68E, substituting 77G for Example 68D. The mixture was purified on SiO2 eluting with ethyl acetate/CH$_2$Cl$_2$ (1/4) followed-by recrystallization from THF to give the title compound as a solid in 67% yield. $^1$H NMR (300 MHz, CD$_3$OD) δ ppm 1.37 (s, 9H), 2.09-2.16 (m, 1H), 2.20-2.28 (m, 1H), 3.10 (s, 6H), 4.21-4.27 (m, 1H), 4.32-4.37 (m, 1H), 5.02-5.04 (m, 3H), 6.82 (t, J=7.68, 15.35 Hz, 1H), 7.18 (d, J=15.95 Hz, 2H), 7.57 (t, J=7.97, 15.02 Hz, 1H), 7.75 (d, J=7.98 Hz, 1H), 8.00 (d, J=8.29 Hz, 1H), 8.48 (s, 1H). MS(+APCI)m/z 450 (M+H)$^+$. Calc for C$_{25}$H$_{31}$N$_5$O$_3$: 1.2HCl: C, 60.87; H, 6.58; N, 14.20. Found: C, 60.93; H, 6.82; N, 13.95.

Compositions of the Invention

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "p arenterally," as used herein, refers to modes of administration, including intravenous, intramuscular, intraperitoneal, intrasternal, subcutaneous, intraarticular injection and infusion.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono-or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, eardrops, eye ointments, powders and solutions are also contemplated as being within the scope of this invention. The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention also can be administered in the form of liposomes. As is known in the art, liposomes are generally derived from phospholipids or other lipid substances. Liposomes are formed by mono-or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

The compounds of the invention can be used in the form of pharmaceutically acceptable salts, esters, or amides derived from inorganic or organic acids. The term "pharmaceutically acceptable salts, esters and amides," as used herein, include salts, zwitterions, esters and amides of compounds of formula (1) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

The term "pharmaceutically acceptable ester," as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyl iodide, benzyl iodide, cyclopentyl iodide. They also can be prepared by reaction of the compound with an acid such as hydrochloric acid and an alkylcarboxylic acid such as acetic acid, or with acid and an arylcarboxylic acid such as benzoic acid.

The term "pharmaceutically acceptable amide," as used herein, refers to non-toxic amides of the invention derived from ammonia, primary $C_1$-to-$C_6$ alkyl amines and secondary $C_1$-to-$C_6$ dialkyl amines. In the case of secondary amines, the amine can also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also can be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention contemplates pharmaceutically active compounds either chemically synthesized or formed by in vivo biotransformation to compounds of formula (I).

Methods of the Invention

Compounds and compositions of the invention are useful for ameliorating or preventing disorders involving TRPV1 receptor activation such as, but not limited to, inflammatory thermal hyperalgesia, bladder overactivity, and urinary incontinence as described by Nolano, M. et al., Pain, Vol. 81, pages 135-145, (1999); Caterina, M. J. and Julius, D., Annu. Rev. Neurosci. Vol. 24, pages 487-517 (2001); Caterina, M. J. et al., Science Vol. 288 pages 306-313 (2000); Caterina, M. J. et al., Nature Vol. 389 pages 816-824 (1997); Fowler, C. Urology Vol. 55 pages 60-64 (2000); and Davis, J. et al., Nature Vol. 405 pages 183-187.

The present invention also provides pharmaceutical compositions that comprise compounds of the present invention. The pharmaceutical compositions comprise compounds of the present invention that may be formulated together with one or more non-toxic pharmaceutically acceptable carriers.

In vivo Evaluation of TRPV1 Prodrugs

The pharmacokinetic behavior of prodrugs was evaluated in male Sprague-Dawley derived rats (n=3/group). Each compound was prepared as a 10 µmol/ml solution in a vehicle of 10% DMSO in PEG-400. Groups of three rats received a 10 µmol/kg (1 ml/kg) intravenous or oral dose of each compound. The intravenous dose was administered in a jugular vein under light isoflurane anesthetic; the oral dose was administered by gavage. Serial blood samples were obtained from a tail vein of each rat 0.1 (IV only), 0.25, 0.5, 1, 1.5, 2, 4, 6 and 8 hours after dosing. Plasma was separated by centrifugation and stored frozen until analysis.

The plasma concentrations of the administered prodrug and a TRPV1 antagonist compound were determined by HPLC-MS/MS. The compounds were removed from the plasma using protein precipitation with acetonitrile. Following centrifugation, the supernatant was transferred to a clean container and evaporated to dryness with nitrogen. The prodrug and parent compound were separated from co-extracted contaminant using reverse phase HPLC, with MS/MS detection and quantitation. Spiked standards were analyzed simultaneously with the samples. The plasma drug concentration of each sample was calculated by least squares linear regression analysis (non-weighted) of the peak area ratio (parent/internal standard) of the spiked plasma standards versus concentration.

Peak plasma concentrations ($C_{max}$) and the time to peak plasma concentration ($T_{max}$) were read directly from the plasma concentration data for each rat. The plasma concentration data were submitted to multi-exponential curve fitting using WinNonlin (WinNonlin-Professional®, Version 3.2, Pharsight Corporation, Mountain View, Calif.). All representative prodrug compounds transformed to a TRPV1 antagonist compound. $C_{max}$ ranges varied from 2% to 100% compared to the 100% $C_{max}$ of the administered TRPV1 antagonist compound.

What is claimed is:

1. A compound of formula (I)

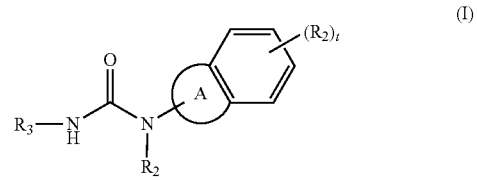

or a pharmaceutically acceptable salt, prodrug, salt of a prodrug or a combination thereof, wherein A is cyclopently

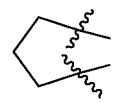

$R_1$ is alkyl, cycloalkyl, alkenyl, halogen or haloalkyl;

$R_2$ is hydrogen;

$R_3$ is

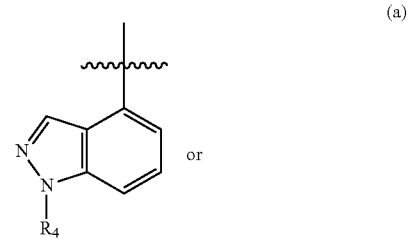

-continued

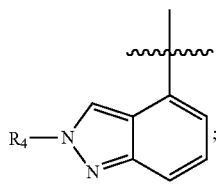
(b)

wherein
R$_4$ is —C(O)—O—(CH$_2$)$_m$R$_5$, —C(O)(CH$_2$)$_n$—R$_6$, —(CH$_2$)$_r$—R$_7$, —C(O)R$_8$, or —CH$_2$(H)(OH)R$_9$;
m is 1, 2, or 3;
n is 1, 2 or 3;
r is 1, 2 or 3;
t is 0, 1, 2, 3 or 4;
u is 0, 1, 2 or 3;
R$_5$ is —O—P(O)(OR$_A$)(OR$_A$), —P(O)(OR$_A$)(OR$_A$), —OR$_A$, —OC(O)(R$_A$), heterocycle, —C(O)OR$_A$, —C(O)N(R$_B$)$_2$, —C(O)(R$_A$), —NR$_A$R$_B$, or —N(R$_B$)C(O)OR$_A$,
R$_6$ is —OC(O)(R$_A$), —OR$_A$, —C(O)OR$_A$, —NR$_A$R$_B$, —OP(O)(OR$_A$)(OR$_A$), or —P(O)(OR$_A$)(OR$_A$);
R$_7$ is heterocycle, —OC(O)(R$_A$), —OC(O)(hydroxyalkyl), —OP(O)(OR$_A$)(OR$_A$), or —P(O)(OR$_A$)(OR$_A$),
R$_8$ is heterocycle or N(R$_{8a}$)(R$_{8b}$) wherein R$_{8a}$ and R$_{8b}$ are independently hydrogen or alkyl;
R$_9$ is alkoxyalkyl, —C(O)OR$_A$, -alkyl-N(R$_B$)C(O)OR$_A$, or heterocyclealkyl;
R$_A$ is hydrogen, alkyl, alkoxyalkyl, aryl or arylalkyl;
R$_B$ is hydrogen or alkyl;
the heterocycle and the heterocycle moiety of the heterocyclealkyl, represented by R$_5$, R$_7$, R$_8$, and R$_9$, are each independently substituted with 0, 1, 2 or 3 substituents independently selected from the group consisting of alkyl, haloalkyl, alkoxy, haloalkoxy, —C(O)OH, -alkyl-C(O)OH, and —N(Z$_A$)(Z$_B$);
Z$_A$ and Z$_B$ are each independently hydrogen, alkyl, —C(O) alkyl, formyl, aryl, or arylalkyl; and
the aryl and the aryl moiety of the arylalkyl, represented by R$_A$, Z$_A$ and Z$_B$ are each independently substituted with 0, 1, 2 or 3 substituents selected from the group consisting of alkyl, haloalkyl, alkoxy and haloalkoxy.

2. The compound of claim 1, wherein
R$_1$ is alkyl, cycloalkyl, alkenyl, halogen or haloalkyl;
R$_2$ is hydrogen;
R$_3$ is

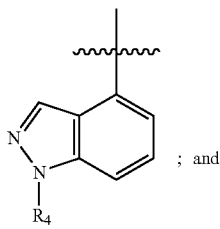
(a)

; and

R$_4$ is —(CH$_2$)$_r$—R$_7$.

3. The compound of claim 1, wherein
R$_1$ is alkyl, cycloalkyl, halogen or haloalkyl;
R$_2$ is hydrogen;
R$_3$ is

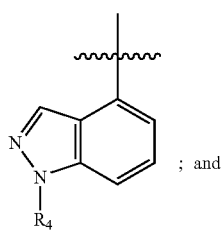
(a)

; and

R$_4$ is —C(O)(CH$_2$)$_n$—R$_6$.

4. The compound of claim 1, wherein
R$_1$ is alkyl, cycloalkyl, halogen or haloalkyl;
R$_2$ is hydrogen;
R$_3$ is

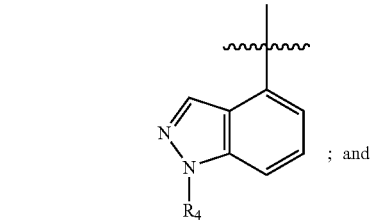
(a)

; and

R$_4$ is —CH$_2$C(H)(OH)R$_9$.

5. The compound of claim 1, wherein
R$_1$ is alkyl, cycloalkyl, halogen or haloalkyl;
R$_2$ is hydrogen;
R$_3$ is

(a)

; and

R$_4$ is —C(O)R$_8$.

6. The compound of claim 1, wherein
R$_1$ is alkyl, cycloalkyl, halogen or haloalkyl;
R$_2$ is heterocyclealkyl;
R$_3$ is

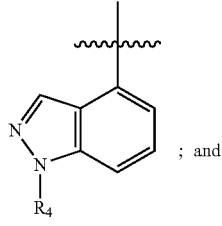
(a)

; and

R$_4$ is —C(O)—O—(CH$_2$)$_m$R$_5$.

7. The compound of claim 6, wherein R$_5$ is —O—P(O)(OR$_A$)(OR$_A$).

8. The compound of claim 6 wherein R$_5$ is —P(O)(OR$_A$)(OR$_A$).

9. The compound of claim 6 wherein R$_5$ is —OR$_A$.

10. The compound of claim 6 wherein R$_5$ is —OC(O)(R$_A$).

11. The compound of claim 6 wherein R$_5$ is heterocycle.

12. The compound of claim 6 wherein R$_5$ is —C(O)OR$_A$.

13. The compound of claim 6 wherein R$_5$ is selected from the group consisting of —C(O)R$_A$, —N(R$_B$)C(O)OR$_A$, —NR$_A$R$_B$, and —C(O)N(R$_B$)$_2$.

14. The compound of claim 1, wherein
R$_1$ is alkyl, cycloalkyl, halogen or haloalkyl;
R$_2$ is hydrogen;
R$_3$ is

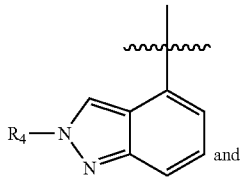

(b)

and

R$_4$ is —C(O)R$_8$.

15. The compound of claim 1, wherein
R$_1$ is alkyl, cycloalkyl, halogen or haloalkyl;
R$_2$ is hydrogen;
R$_3$ is

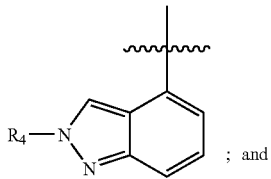

(b)

; and

R$_4$ is —CH$_2$C(H)(OH)R$_9$.

16. The compound of claim 1, wherein
R$_1$ is alkyl, cycloalkyl, halogen or haloalkyl;
R$_2$ is hydrogen;
R$_3$ is

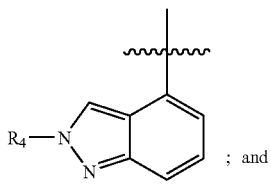

(b)

; and

R$_4$ is selected from the group consisting of —C(O)—O—(CH$_2$)$_m$R$_5$, —C(O)(CH$_2$)$_n$—R$_6$, and —(CH$_2$)$_r$—R$_7$.

17. A compound selected from the group consisting of
N-[(1R)-5-tert-butyl-2,3-dihydro-1H-inden-1-yl]-N'-[1-(2-morpholin-4-ylethyl)-1H-indazol-4-yl]urea;

2-{4-[({[(1R)-5-tert-butyl-2,3-dihydro-1H-inden-1-yl]amino}carbonyl)amino]-1H-indazol-1-yl}-2-oxoethyl acetate;

N-{1-[(benzyloxy)acetyl]-1H-indazol-4-yl}-N'-[(1R)-5-tert-butyl-2,3-dihydro-1H-inden-1-yl]urea;

N-[(1R)-5-tert-butyl-2,3-dihydro-1H-inden-1-yl]-N'-[1-(methoxyacetyl)-1H-indazol-4-yl]urea;

4-{4-[({[(1R)-5-tert-butyl-2,3-dihydro-1H-inden-1-yl]amino}carbonyl)amino]-1H-indazol-1-yl}-4-oxobutanoic acid;

N-[(1R)-5-tert-butyl-2,3-dihydro-1H-inden-1-yl]-N'-[1-(N,N-dimethylglycyl)-1H-indazol-4-yl]urea trifluoroacetic acid salt;

N-[(1R)-5-tert-butyl-2,3-dihydro-1H-inden-1-yl]-N'-(1-glycoloyl-1H-indazol-4-yl)urea;

5-{4-[({[(1R)-5-tert-butyl-2,3-dihydro-1H-inden-1-yl]amino}carbonyl)amino]-1H-indazol-1-yl}-5-oxopentanoic acid;

2-(phosphonooxy)ethyl 4-[({[(1R)-5-tert-butyl-2,3-dihydro-1H-inden-1-yl]amino}carbonyl)amino]-1H-indazole-1-carboxylate;

2-(benzyloxy)ethyl 4-[({[(1R)-5-tert-butyl-2,3-dihydro-1H-inden-1-yl]amino}carbonyl)amino]-1H-indazole-1-carboxylate;

2-hydroxyethyl 4-[({[(1R)-5-tert-butyl-2,3-dihydro-1H-inden-1-yl]amino}carbonyl)amino]-1H-indazole-1-carboxylate;

2-[(di-tert-butoxyphosphoryl)oxy]ethyl 4-[({[(1R)-5-tert-butyl-2,3-dihydro-1H-inden-1-yl]amino}carbonyl)amino]-1H-indazole-1-carboxylate;

3-(benzyloxy)propyl 4-[({[(1R)-5-tert-butyl-2,3-dihydro-1H-inden-1-yl]amino}carbonyl)amino]-1H-indazole-1-carboxylate;

3-hydroxypropyl 4-[({[(1R)-5-tert-butyl-2,3-dihydro-1H-inden-1-yl]amino}carbonyl)amino]-1H-indazole-1-carboxylate;

3-[(di-tert-butoxyphosphoryl)oxy]propyl 4-[({[(1R)-5-tert-butyl-2,3-dihydro-1H-inden-1-yl]amino}carbonyl)amino]-1H-indazole-1-carboxylate;

3-(phosphonooxy)propyl 4-[({[(1R)-5-tert-butyl-2,3-dihydro-1H-inden-1-yl]amino}carbonyl)amino]-1H-indazole-1-carboxylate;

N-[(1R)-5-tert-butyl-2,3-dihydro-1H-inden-1-yl]-N'-[1-(hydroxymethyl)-1H-indazol-4-yl]urea;

{4-[({[(1R)-5-tert-butyl-2,3-dihydro-1H-inden-1-yl]amino}carbonyl)amino]-1H-indazol-1-yl}methyl acetate;

{4-[({[(1R)-5-tert-butyl-2,3-dihydro-1H-inden-1-yl]amino}carbonyl)amino]-1H-indazol-1-yl}methyl 3-hydroxypropanoate;

{[bis(benzyloxy)phosphoryl]oxy}methyl 4-[({[(1R)-5-tert-butyl-2,3-dihydro-1H-inden-1-yl]amino}carbonyl)amino]-1H-indazole-1-carboxylate;

(phosphonooxy)methyl 4-[({[(1R)-5-tert-butyl-2,3-dihydro-1H-inden-1-yl]amino}carbonyl)amino]-1H-indazole-1-carboxylate;

dibenzyl 3-{4-[({[(1R)-5-tert-butyl-2,3-dihydro-1H-inden-1-yl]amino}carbonyl)amino]-1H-indazol-1-yl}-3-oxopropyl phosphate;

3-{4-[({[(1R)-5-tert-butyl-2,3-dihydro-1H-inden-1-yl]amino}carbonyl)amino]-1H-indazol-1-yl}-3-oxopropyl dihydrogen phosphate;

[bis(benzyloxy)phosphoryl]methyl 4-[({[(1R)-5-tert-butyl-2,3-dihydro-1H-inden-1-yl]amino}carbonyl)amino]-1H-indazole-1-carboxylate;

[({4-[({[(1R)-5-tert-butyl-2,3-dihydro-1H-inden-1-yl]amino}carbonyl)amino]-1H-indazol-1-yl}carbonyl)oxy]methylphosphonic acid;

[({4-[({[(1R)-5-tert-butyl-2,3-dihydro-1H-inden-1-yl]amino}carbonyl)amino]-1H-indazol-1-yl}carbonyl)oxy]methylphosphonic acid triethylamine salt;

2-methoxyethyl 4-[({[(1R)-5-tert-butyl-2,3-dihydro-1H-inden-1-yl]amino}carbonyl)amino]-1H-indazole-1-carboxylate;

(2,2-dimethyl-1,3-dioxolan-4-yl)methyl 4-[({[(1R)-5-tert-butyl-2,3-dihydro-1H-inden-1-yl]amino}carbonyl)amino]-1H-indazole-1-carboxylate;

(2-oxo-1,3-dioxolan-4-yl)methyl 4-[({[(1R)-5-tert-butyl-2,3-dihydro-1H-inden-1-yl]amino}carbonyl)amino]-1H-indazole-1-carboxylate;

2-(benzyloxy)ethyl 4-[({[(1R)-5-tert-butyl-2,3-dihydro-1H-inden-1-yl]amino}carbonyl)amino]-1H-indazole-1-carboxylate;

2-hydroxyethyl 4-[({[(1R)-5-tert-butyl-2,3-dihydro-1H-inden-1-yl]amino}carbonyl)amino]-1H-indazole-1-carboxylate;

2-(benzyloxy)-2-oxoethyl 4-[({[(1R)-5-tert-butyl-2,3-dihydro-1H-inden-1-yl]amino}carbonyl)amino]-1H-indazole-1-carboxylate;

2-{[(benzyloxy)carbonyl]amino}ethyl 4-[({[(1R)-5-tert-butyl-2,3-dihydro-1H-inden-1-yl]amino}carbonyl)amino]-1H-indazole-1-carboxylate;

[({4-[({[(1R)-5-tert-butyl-2,3-dihydro-1H-inden-1-yl]amino}carbonyl)amino]-1H-indazol-1-yl}carbonyl)oxy]acetic acid;

2-aminoethyl 4-[({[(1R)-5-tert-butyl-2,3-dihydro-1H-inden-1-yl]amino}carbonyl)amino]-1H-indazole-1-carboxylate hydrochloride;

2-ethoxy-2-oxoethyl 4-[({[(1R)-5-tert-butyl-2,3-dihydro-1H-inden-1-yl]amino}carbonyl)amino]-1H-indazole-1-carboxylate;

(diethoxyphosphoryl)methyl 4-[({[(1R)-5-tert-butyl-2,3-dihydro-1H-inden-1-yl]amino}carbonyl)amino]-1H-indazole-1-carboxylate;

2-(diethylamino)-2-oxoethyl 4-[({[(1R)-5-tert-butyl-2,3-dihydro-1H-inden-1-yl]amino}carbonyl)amino]-1H-indazole-1-carboxylate;

2-oxopropyl 4-[({[(1R)-5-tert-butyl-2,3-dihydro-1H-inden-1-yl]amino}carbonyl)amino]-1H-indazole-1-carboxylate;

2-(acetyloxy)ethyl 4-[({[(1R)-5-tert-butyl-2,3-dihydro-1H-inden-1-yl]amino}carbonyl)amino]-1H-indazole-1-carboxylate;

2-(dimethoxyphosphoryl)ethyl 4-[({[(1R)-5-tert-butyl-2,3-dihydro-1H-inden-1-yl]amino}carbonyl)amino]-1H-indazole-1-carboxylate;

[({4-[({[(1R)-5-tert-butyl-2,3-dihydro-1H-inden-1-yl]amino}carbonyl)amino]-1H-indazol-1-yl}carbonyl)oxy]methylphosphonic acid, diethylaminoethanol salt;

[({4-[({[(1R)-5-tert-butyl-2,3-dihydro-1H-inden-1-yl]amino}carbonyl)amino]-1H-indazol-1-yl}carbonyl)oxy]methylphosphonic acid, triethanolamine salt;

[({4-[({[(1R)-5-tert-butyl-2,3-dihydro-1H-inden-1-yl]amino}carbonyl)amino]-1H-indazol-1-yl}carbonyl)oxy]methylphosphonic acid, piperazine salt;

[({4-[({[(1R)-5-tert-butyl-2,3-dihydro-1H-inden-1-yl]amino}carbonyl)amino]-1H-indazol-1-yl}carbonyl)oxy]methylphosphonic acid, N-methyl-D-glucamine salt;

N-[(1R)-5-tert-butyl-2,3-dihydro-1H-inden-1-yl]-N'-[1-(2-hydroxy-3-methoxypropyl)-1H-indazol-4-yl]urea;

N-[(1R)-5-tert-butyl-2,3-dihydro-1H-inden-1-yl]-N'-[2-(2-hydroxy-3-methoxypropyl)-2H-indazol-4-yl]urea;

methyl 3-{4-[({[(1R)-5-tert-butyl-2,3-dihydro-1H-inden-1-yl]amino}carbonyl)amino]-1H-indazol-1-yl}-2-hydroxypropanoate;

methyl 3-{4-[({[(1R)-5-tert-butyl-2,3-dihydro-1H-inden-1-yl]amino}carbonyl)amino]-2H-indazol-2-yl}-2-hydroxypropanoate;

tert-butyl 3-{4-[({[(1R)-5-tert-butyl-2,3-dihydro-1H-inden-1-yl]amino}carbonyl)amino]-1H-indazol-1-yl}-2-hydroxypropylcarbamate;

3-{4-[({[(1R)-5-tert-butyl-2,3-dihydro-1H-inden-1-yl]amino}carbonyl)amino]-1H-indazol-1-yl}-2-hydroxypropanoic acid;

3-{4-[({[(1R)-5-tert-butyl-2,3-dihydro-1H-inden-1-yl]amino}carbonyl)amino]-2H-indazol-2-yl}-2-hydroxypropanoic acid;

N-[(1R)-5-tert-butyl-2,3-dihydro-1H-inden-1-yl]-N'-[2-(2-hydroxy-3-morpholin-4-ylpropyl)-2H-indazol-4-yl]urea;

N-[(1R)-5-tert-butyl-2,3-dihydro-1H-inden-1-yl]-N'-[1-(2-hydroxy-3-morpholin-4-ylpropyl)-1H-indazol-4-yl]urea;

N-[(1R)-5-tert-butyl-2,3-dihydro-1H-inden-1-yl]-N'-{1-[(4-methylpiperazin-1-yl)carbonyl]-1H-indazol-4-yl}urea;

N-[(1R)-5-tert-butyl-2,3-dihydro-1H-inden-1-yl]-N'-{2-[(4-methylpiperazin-1-yl)carbonyl]-2H-indazol-4-yl}urea;

N-[(1R)-5-tert-butyl-2,3-dihydro-1H-inden-1-yl]-N'-[1-(N,N-dimethylglycyl)-1H-indazol-4-yl]urea;

N-[(1R)-5-tert-butyl-2,3-dihydro-1H-inden-1-yl]-N'-[1-(N,N-dimethylglycyl)-1H-indazol-4-yl]urea, hydrochloride salt;

((R)-1-(5-tert-butyl-2,3-dihydro-1H-inden-1-yl)-3-(1-(2-(2-methoxyethoxy)acetyl)-1H-indazol-4-yl)urea;

1-((R)-5-tert-butyl-2,3-dihydro-1H-inden-1-yl)-3-(1-(3,5,5-trimethylhexanoyl)-1H-indazol-4-yl)urea;

2-ethylhexyl 4-(3-((R)-5-tert-butyl-2,3-dihydro-1H-inden-1-yl)ureido)-1H-indazole-1-carboxylate;

(R)-1-(1-(2-(2-butoxyethoxy)acetyl)-1H-indazol-4-yl)-3-(5-tert-butyl-2,3-dihydro-1H-inden-1-yl)urea;

3-(dimethylamino)propyl 4-(3-(4-cyclopropyl-5-fluoro-2,3-dihydro-1H-inden-1-yl)ureido)-1H-indazole-1-carboxylate;

1-(4-cyclopropyl-2,3-dihydro-1H-inden-1-yl)-3-(1-(2-(dimethylamino)acetyl)-1H-indazol-4-yl)urea trifluoroacetate;

1-(5-cyclopropyl-2,3-dihydro-1H-inden-1-yl)-3-(1-(2-(dimethylamino)acetyl)-1H-indazol-4-yl)urea hydrochloride;

1-(1-(2-(dimethylamino)acetyl)-1H-indazol-4-yl)-3-(4-(3,3-dimethylbutyl)-5-fluoro-2,3-dihydro-1H-inden-1-yl)urea;

(R)-1-(4-cyclopropyl-5-fluoro-2,3-dihydro-1H-inden-1-yl)-3-(1-(2-(dimethylamino)acetyl)-1H-indazol-4-yl)urea; and (R)-1-(5-tert-butyl-2,3-dihydro-1H-inden-1-yl)-3-(1-(2-(methylamino)acetyl)-1H-indazol-4-yl)urea hydrochloride;

18. A pharmaceutical composition comprising a therapeutically effective amount of one or more compound of formula (I) as described in claim 1, or a therapeutically acceptable salt thereof, or combination thereof, and a pharmaceutically acceptable carrier.

19. A method of treating neuropathic pain, inflammatory pain, the method comprising administering to a subject in need thereof a therapeutically effective amount of a compound of formula (I) according to claim 1 or a pharmaceutically acceptable salt thereof.

20. A method of treating thermal hyperalgesia, bladder overactivity or urinary incontinence, the method comprising administering to a subject in need thereof a therapeutically effective amount of a compound of formula (I) according to claim 1 or a pharmaceutically acceptable salt thereof.

21. The compound of claim 1 of formula (II),

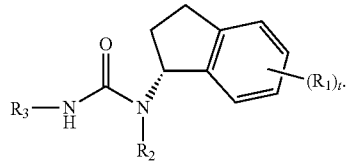

(II)

22. The compound of claim 1 of formula (III),

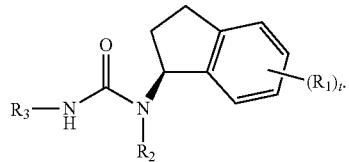

(III)

* * * * *